(12) United States Patent
Rafferty et al.

(10) Patent No.: US 7,049,312 B1
(45) Date of Patent: May 23, 2006

(54) BENZOTHIAZINONE AND BENZOXAZINONE COMPOUNDS

(75) Inventors: Paul Rafferty, Nottingham (GB); David Calderwood, Nottingham (GB); Lee Arnold, Westborough, MA (US); Beatriz Gonzalez Pascual, Madrid (ES); Jose L. Ortego Martinez, Madrid (ES); Maria J. Perez de Vega, Madrid (ES); Isabel Fernandez, Madrid (ES)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/585,925

(22) Filed: Jun. 2, 2000

Related U.S. Application Data

(60) Provisional application No. 60/137,410, filed on Jun. 3, 1999.

(51) Int. Cl.
| | |
|---|---|
| *C07D 513/04* | (2006.01) |
| *C07D 417/12* | (2006.01) |
| *C07D 417/14* | (2006.01) |
| *A61K 31/5415* | (2006.01) |
| *A61K 31/542* | (2006.01) |

(52) U.S. Cl. .................. 514/224.2; 544/48; 544/51; 544/52

(58) Field of Classification Search ................ 544/48, 544/51, 52; 514/224.2
See application file for complete search history.

(56) References Cited

U.S. PATENT DOCUMENTS

| | | | |
|---|---|---|---|
| 3,635,956 A | 1/1972 | Krapcho | 260/240 K |
| 3,812,114 A | 5/1974 | Krapcho | 260/243 R |
| 3,865,818 A | 2/1975 | Krapcho et al. | 260/240 F |
| 3,923,709 A | 12/1975 | Worley | 260/240 K |
| 4,490,292 A | 12/1984 | Maki et al. | 260/239.3 B |

FOREIGN PATENT DOCUMENTS

| | | |
|---|---|---|
| DE | 2051474 | 5/1971 |
| JP | 61229874 | * 10/1986 |
| WO | WO 94/05647 | 3/1994 |
| WO | WO 95/13269 | 5/1995 |

OTHER PUBLICATIONS

English Abstract of JP 61229874 from STN search printout.*
Belezheva, et al.; *CHCCAL; Chem. Heterocycl. Compd.* (Engl. Transl.); 14; 1978; 1088, 1092; KGSSAQ; Khim. Geterotsikl. Soedin.; 14; 1978; 1343.
Worley, J.W., et al., "2-Dialkylphosphonyl- and 2-Alkylidene-3,4-dihydro-3-oxo-2H-1,4-benzothiazines", *J. Org. Chem.*, 40(12):1731-1734 (1975).
Kugita, H., et al., "Synthesis of 1,5-Benzothiazepine Derivatives", *Chem. Pharm. Bull.*, 18(10):2028-2037 (1970).
Kaupp, G., et al., "Umlagerungen and komplexe Eliminierungen mit 1,5-Benzothiazepin-4-onen", *Chem. Ber.*, 119:3109-3120 (1986).
Eiden, F., et al., "Uber 2,3-Dihydro-1,4-benzothiazin-3-one", *Arch. Pharm.*, 312:302-312 (1979).
Krapcho, J., et al., "4-[3-(Dimethylamino)propyl]-3,4-dihydro-2-(1-hydroxyethyl)-3-phenyl-2H-1,4-benzothiazine and Related Compounds. A New Class of Antiinflammatory Agents", *J. Med. Chem.*, 16(7):776-779 (1973).
McCarthy, E.T., et al., "A New Synthesis of Pyrido [3,2-*b*] [1,4] Benzothiazines", *J. Chem. Research (M)*, Paper E/271/87, 1328-1336 (1988).
Reddy Sastry, C.V., et al., "Synthesis & Biological Activity of Some New 6-Isothiocyanato-, 6-N- [N,N-Bis (methoxycarbonyl) guanidino]-, & 6-(2-Aryl/2-arylaminothiazol-4-yl)-2H-1, 4-benzoxazin-3 (4H) -ones", *Indian Journal of Chemistry*, 26B:662-665 (1987).

(Continued)

*Primary Examiner*—James O. Wilson
*Assistant Examiner*—Kahsay Habte
(74) *Attorney, Agent, or Firm*—Gayle B. O'Brien

(57) ABSTRACT

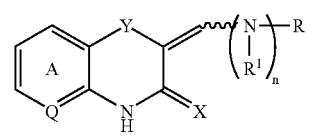

Q is —N=or $CR^2$
X is S, O or $NOR^3$
Y is —O—, —S—, —SO— or —$SO_2$—
R and $R^1$ are each, independently, H, a substituted or unsubstituted aliphatic, aromatic, heteroaromatic or aralkyl group
$R^2$ is H or a substituent
$R^3$ is H, or —$C(O)R^4$
$R^4$ is a substituted or unsubstituted aliphatic or aromatic group
n is an integer from 0 to 1

Chemical compounds having structural formula I and physiologically acceptable salts thereof, are inhibitors of serine/threonine and tyrosine kinase activity. Several of the tyrosine kinases, whose activity is inhibited by these chemical compounds, are involved in angiogenic processes. Thus, these chemical compounds can ameliorate disease states where angiogenesis or endothelial cell hyperproliferation is a factor. These compounds can be used to treat cancer and hyperproliferative disorders.

10 Claims, No Drawings

OTHER PUBLICATIONS

Reddy Sastry, C.V., et al., "Synthesis of Some 2-Thenylidene-3-N, N-Heterocyclyl-2H-1, 4-Benzoxazines as Potential Anthelmintic Agents", *Indian Drugs,* 26(8):400-403 (1988).

Turk, C.F., et al., "Synthesis and Central Nervous System Activity of 2-Arylidene-4-aminoalkyl-2H, 1,4-benzoxazin-3 (4H)-ones and Related Compounds", *J. Med. Chem.,* 20(5):729-732 (1977).

Gezginci, H., et al., "Synthesis of New 2-Arylidene-2H-1,4-Benzoxazin-3(4H)-Ones", *Il Farmaco,* 52(4):255-256 (1997).

Baliah, V., et al., "Preparation of Some 2-Arylidene-3,4-dihydro-3-oxobenzo-1,4-thiazines", *J. Chem. Soc.,* 4703-4704 (1960).

Shah, S.R., et al., "Reaction of the Vilsmeier Product, 3-Chloro-2-dimethylaminomethylene-I,4-benzothiazene with Aromatic Amines & Active Methylene Compounds", *Indian J. of Chem.,* 10:977-981 (1972).

Talukdar, P.B., et al., "Studies of the Blue Color of Some Mesoionic 1,3-thiazolo(3,2-a)-4-quinazolones," *Indian J. Chem.,* Sect. B, 16B(8):678-682 (1978). (From *Chem. Abstracts,* 1979, 90(7), Abstract No. 54901w.

Teitei, T., "The Synthesis of (3-oxo-3,4-dihydro-2H-1,4-benzoxazin-2-y1)acetuc acud abd (3-oxo-3,4-dihydro-2H-1,4-benzoxazin-2-y1)-acetic acid derivatives," *Aust. J. Chem.,* 39(3): 503-510 (1987). From *Chem. Abstracts,* 1987, 106(13) Abstract No. 102191n.

Coutts, R.T., et al.; "Organic sulfur compounds. VII. Reactions of benzothiazine acids," *Can. J. Chem.,* 48(23): 3727-3732 (1970). (From *Chem. Abstracts,* 1971, 74(9), Abstract No. 42325t.

Nicolaus, R.A., "Structure and biogenesis of phaeomelanins. VII. Structure of trichosiderins," *Gazz. Chim. Ital.* 99(4):323-350 (1969). From *Chem. Abstracts,* 1969, 71(11), Abstract No. 49871q.

Gasparova, R., et al., "Study of microwave irradiation effect on condensation of 6-R-3-formylchromones with active methylene compounds," *Collect. Czech. Chem. Commun.,* 60(7):1178-1185 (1995). (From *Chem. Abstracts,* 1996, 124(5), Abstract No. 55745f.

Anzai, N., et al., "2-Arylmethylene-1,4-benzothiazin-3(4H)-ones," *Japan. Kokai,* 74,101,389 (1974). (From *Chem. Abstracts,* 1975, 82(21), Abstract No. 140162x.

Hamari Yakuhin Kogyo Co., Ltd., "1,5-Benzothiazepine derivatives," *Jpn. Kokai Tokkyo Koho,* 60 72, 875 (1985). (From *Chem. Abstracts,* 1985, 103(17), Abstract No. 142032f.

Varano, F., et al., "Synthesis of 2-substituted 6,8-dichloro-3,4-dihydro-3-oxo-2H-1,4-benzothiazine 1,1-dioxides and 1-oxides as glycine-NMDA receptor antagonists," *Farmaco,* 53(12) (1998). (From *Chem. Abstracts,* 1999, 131(4), Abstract No. 44782j.

* cited by examiner

BENZOTHIAZINONE AND BENZOXAZINONE COMPOUNDS

RELATED APPLICATION(S)

This application claims the benefit of U.S. Provisional Application No. 60/137,410, filed Jun. 3, 1999, the entire teachings of which are incorporated herein by reference.

This invention relates to certain benzothiazinones and benzoxazinones which are inhibitors of protein kinases, particularly tyrosine kinases and serine/threonine kinases, of which some are novel compounds, to pharmaceutical compositions containing these benzothiazinones or benzoxazinones, and to processes for preparing these benzothiazinones and benzoxazinones.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383–391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203–212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1–20.

Proteins with SH2 (src homology −2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413–423; Songyang et al., 1994, *Mol. Cell. Biol.* 14:2777–2785; Songyang et al., 1993, *Cell* 72:767–778; and Koch et al., 1991, *Science* 252:668–678; Shoelson, *Curr. Opin. Chem. Biol.* (1997), 1(2), 227–234; Cowburn, *Curr. Opin. Struct. Biol.* (1997), 7(6), 835–838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767–778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767–778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases, and growth factors that bind thereto, have been suggested to play a role in angiogenesis, although some may promote angiogenesis indirectly (Mustonen and Alitalo, *J. Cell Biol.* 129:895–898, 1995). One such receptor tyrosine kinase, known as "fetal liver kinase 1" (FLK-1), is a member of the type III subclass of RTKs. An alternative designation for human FLK-1 is "kinase insert domain-containing receptor" (KDR) (Terman et al., *Oncogene* 6:1677–83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs et al, *Oncogene* 8(1): 11–15, 1993). DNAs encoding mouse, rat and human FLK-1 have been isolated, and the nucleotide and encoded amino acid sequences reported (Matthews et al., *Proc. Natl. Acad. Sci. USA*, 88:9026–30, 1991; Terman et al., 1991, supra; Terman et al., *Biochem. Biophys. Res. Comm.* 187:1579–86, 1992; Sarzani et al., supra; and Millauer et al., *Cell* 72:835–846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fms-like tyrosine kinase-1" (Flt-1) is related to FLK-1/KDR (DeVries et al. *Science* 255;989–991, 1992; Shibuya et al., *Oncogene* 5:519–524, 1990). An alternative designation for Flt-1 is "vascular endothelial cell growth factor receptor 1" (VEGFR-1). To date, members of the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine& Growth Factor Reviews* 7: 259–270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in adult organs such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., *Endocrinology* 133: 848–859, 1993; Kolch et al., *Breast Cancer Research and Treatment* 36: 139–155, 1995; Ferrara et al., *Endocrine Reviews* 18(1); 4–25, 1997; Ferrara et al., *Regulation of Angiogenesis* (ed. L. D. Goldberg and E. M. Rosen), 209–232, 1997). In addition, VEGF has been implicated in the control and enhancement of vascular permeability (Connolly, et al., *J. Biol. Chem.* 264: 20017–20024, 1989; Brown et al., *Regulation of Angiogenesis* (ed. L. D. Goldberg and E. M. Rosen), 233–269, 1997).

Different forms of VEGF arising from alternative splicing of mRNA have been reported, including the four species described by Ferrara et al. (*J. Cell. Biochem.* 47:211–218, 1991). Both secreted and predominantly cell-associated species of VEGF have been identified by Ferrara et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.*, 159–164, 1998 and references cited therein).

Placenta growth factor (PlGF) has an amino acid sequence that exhibits significant homology to the VEGF sequence (Park et al., *J. Biol. Chem.* 269:25646–54, 1994; Maglione et al. *Oncogene* 8:925–31, 1993). As with VEGF, different species of PlGF arise from alternative splicing of mRNA, and the protein exists in dimeric form (Park et al., supra). PlGF-1 and PlGF-2 bind to Flt-4 with high affinity, and PlGF-2 also avidly binds to neuropilin-1 (Migdal et al, *J. Biol. Chem.* 273 (35): 22272–22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper et al, *Proc. Natl. Acad. Sci. U.S.A.* (1998), 95(20): 11709–11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki et al, *Am. J. Pathol.* (1998), 153(2): 395–403; Witzenbichler et al, *Am. J. Pathol.* (1998), 153(2), 381–394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14), 8413–8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S.A.* (1998), 95(2), 548–553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Williams, *Diabetelogia* 40: S118–120

(1997)). Until now, no direct evidence for the essential role of KDR in VEGF-mediated vascular hyperpermeability has been disclosed.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, *Oncogene* 8:2025–2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Application No. 4,966,849), soluble receptors and antibodies (Application No. WO 94/10202; Kendall & Thomas, 1994, *Proc. Natl. Acad. Sci* 90:10705–09; Kim et al., 1993, *Nature* 362:841–844), RNA ligands (Jellinek, et al., *Biochemistry* 33:10450–56; Takano, et al., 1993, *Mol. Bio. Cell* 4:358A; Kinsella, et al. 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475–478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is also known as cdk1)

Cdc2/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors could suppress proliferation and may restore the normal control of cell cycle progression.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

This invention is directed to compounds of the formula

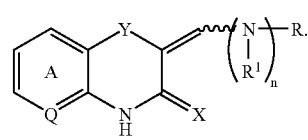

I and physiologically acceptable salts thereof, wherein, ring A is substituted or unsubstituted; Q is —N= or —CR$^2$=; X is S, O, or NOR$^3$; Y is —O—, —S—, —SO— or —SO$_2$—; R and R$^1$ are each, independently, hydrogen, a substituted or unsubstituted aliphatic, aromatic, heteroaromatic or aralkyl group; R$^2$ is hydrogen or a substitutent; R$^3$ is hydrogen or —C(O)R$^4$; R$^4$ is a substituted or unsubstituted aliphatic or aromatic group; and n is an integer from 0 to 1.

Aliphatic groups include straight chained or branched C$_1$–C$_{18}$ hydrocarbons, or cyclic C$_3$–C$_{18}$ hydrocarbons which are completely saturated or which contain one or more units of unsaturation. Lower alkyl groups are straight chained or branched C$_1$–C$_6$ hydrocarbons or C$_3$–C$_6$ cyclic hydrocarbons, which are completely saturated.

Aromatic groups include carbocyclic ring systems (e.g. benzyl and cinnamyl) and fused polycyclic aromatic ring systems (e.g. naphthyl and 1,2,3,4-tetrahydronaphthyl). In addition, aromatic groups includes heteroaryl ring systems (e.g. pyridines, thiophenes, furans, pyrroles, imidazoles, pyrazoles, triazoles, pyrimidines, pyrazines, pyridazines, oxazoles, thiazoles, isoxazoles, isothiazoles, tetrazoles, oxadiazoles, or thiadiazoles) and heteroaryl ring systems in which a carbocyclic aromatic ring, carbocyclic non-aromatic ring or heteroaryl ring is fused to one or more other heteroaryl rings (e.g. benzimidazole, indole, tetrahydroindole, azaindole, indazole, quinoline, imidazopyridine, purine, pyrrolo[2,3-d]pyrimidine, pyrazolo[3,4-d]pyrimidine) and their N-oxides. An aryl group, as used herein, refer to an aromatic group having five or six atoms. An aralkyl group is an aryl substituent that is linked to a compound by an aliphatic group having from one to about six carbon atoms. Similarly, a heteroaralkyl group is a heteroaryl moiety that is linked to a compound by an aliphatic group having from one to about six carbon atoms; and a heterocycloalkyl group is a heteroaryl moiety that is linked to a compound by an aliphatic group having from one to about six carbon atoms.

Suitable substituents include halogens, trihalomethyl, cyano, hydroxy, nitro, —NR$^5$, R$^6$, carbamoyl, carboxy, carboxamidoxime, —SO$_2$NR$^5$R$^6$, —NHSO$_2$R$^5$, R$^7$—O—R$^8$— or R$^7$—O—R$^8$—O—R$^9$—, wherein R$^5$ and R$^6$ are each, independently, hydrogen, a lower alkyl, benzyl, heteroarylmethyl or aryl group optionally substituted with a halogen, cyano or hydroxy group; R$^7$ is hydrogen, R$^{10}$C(O)—, or a lower alkyl or aryl group which is optionally substituted with one or more halogens, cyano, hydroxy or —NR$^5$R$^6$; R$^8$ and R$^9$ are each, independently, —C(O)— or a lower alkyl or aryl group which is optionally substituted with one or more halogens, cyano, hydroxy or —NR$^5$R$^6$; and R$^{10}$ is a lower alkyl or an aryl group. Other suitable substitutents include R$^{11}$—, R$^{10}$—, R$^{11}$OC(O)—, R$^{11}$NHC(O)—, R$^{11}$C(O)—, R$^{11}$C(O)O—, R$^{11}$S—, R$^{11}$S(O)—, R$^{11}$S(O)$_2$—, R$^5$R$^6$NC(O)—, R$^{11}$HNC(O)NH—, R$^{11}$C(O)NH—, R$^{12}$(CH$_2$)$_m$—, R$^{12}$(CH$_2$)$_n$C(O)NH—, R$^{12}$(CH$_2$)$_m$O—, R$^{12}$(CH$_2$)$_m$NH—, [R$^{12}$(CH$_2$)$_m$]$_2$CH—O—(CH$_2$)$_m$—, R$^{12}$(CH$_2$)$_m$OC(O)—, R$^{12}$(CH$_2$)$_m$NHC(O)—, R$^{12}$(CH$_2$)$_m$CH(R$^{12}$)(CH$_2$)$_m$—, R$^{12}$(CH$_2$)$_m$C(O)O—, R$^{12}$(CH$_2$)$_m$NHC(O)O—, R$^{12}$(CH$_2$)$_m$OC(O)NH—, R$^{12}$(CH$_2$)$_m$OC(O)O—, R$^{12}$(CH$_2$)$_m$NHC(O)(CH$_2$)$_m$—, R$^{12}$(CH$_2$)$_m$OC(O)(CH$_2$)$_m$—, R$^{12}$(CH$_2$)$_m$(CR$^5$R$^6$)$_m$(CH$_2$)$_m$N(R$^5$)(CH$_2$)$_m$—, R$^{12}$C(O)(CH$_2$)$_m$—, R$^2$(CH$_2$)$_m$(CR$^5$R$^6$)$_m$(CH$_2$)$_m$N(R$^5$)C(O)(CH$_2$)$_m$—, R$^{12}$(CH$_2$)$_m$(CR$^5$R$^6$)$_m$(CH$_2$)$_m$N(R$^5$)(CH$_2$)$_m$C(O)—, [R$^{12}$(CH$_2$)$_m$]$_2$NC(O)(CH$_2$)$_m$—, R$^{12}$(CH$_2$)$_m$C(O)—,, R$^{12}$(CH$_2$)$_m$(CR$^5$R$^6$)$_m$(CH$_2$)$_m$N(R$^5$)SO$_2$—, R$^{12}$(CH$_2$)$_m$(CR$^5$R$^6$)$_m$(CH$_2$)$_m$O(CH$_2$)$_m$—, wherein R$^{11}$ is hydrogen, a lower alkyl group, a saturated or unsaturated heterocyclic ring, an aryl group or an aralkyl group where these groups are optionally substituted with one or more halogens, cyano, hydroxy or —NR$^5$R$^6$; R$^{12}$ is halogen, carboxy, carbamoyl, lower alkyloxycarbonyl, lower alkenyl, hydroxy, a lower alkyloxy, a lower alcanoyloxy, —NR$^5$R$^6$ or is selected from the group consisting of morpholine, piperazine, piperidine, pyrrolidine, homopiperazine, pyridine, triazole, tetrazole, imidazole and tetrahydropyrane optionally substituted with an hydroxy, lower alkyl, lower alkyloxy, lower hydroxyalkyl, lower aminoalkyl, lower alkyloxyalkyl, a saturated or unsaturated heterocyclic ring, cycloalkyl or —NR$^5$R$^6$ group; and m is independently an integer from 0 to 4. Specific compounds of formula I are given in List I.

In one embodiment, the compounds of the invention are represented by the formula

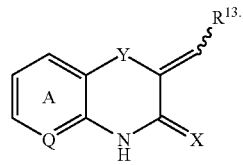

II and physiologically acceptable salts thereof, wherein ring A is substituted or unsubstituted, and Q, X, and Y are defined as above. R$^{13}$ is hydrogen, a substituted or unsubstituted aliphatic group, a substituted or unsubstituted heteroaryl or a group represented by the following structure:

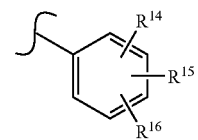

wherein, R$^{14}$, R$^{15}$ and R$^{16}$ are, independently, an alkyl, hydrogen, halogen, hydroxyl, thiol, thioether, —NR$^5$R$^6$, aldehyde, carboxylic acid or amide, with the proviso that R$^{13}$ is not 3-furanyl, thiophenyl or 3-pyridinyl.

In another embodiment, the compounds of the invention are represented by the formula

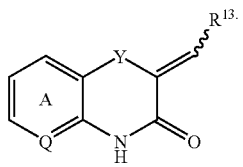

III and physiologically acceptable salts thereof, wherein ring A is substituted or unsubstituted, and Q, Y and R$^{13}$ are defined as above.

In a preferred embodiment the compounds of the invention are represented by the following formula;

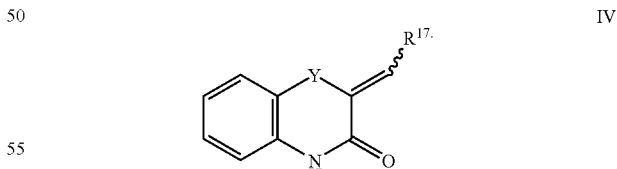

IV and physiologically acceptable salts thereof, wherein Y is —O— or —S— and R$^{17}$ is substituted or unsubstituted pyrrole, pyrazole, imidazole, oxazole, isoxazole, thiazole, isothiazole, triazole, tetrazole, indole, 7-azaindole, indazole, purine, pyrrolo[2,3-d]pyrimidine, pyrazolo[3,4-d]pyrimidine, imidazo[4,5-b]pyridine, imidazo[1,2-a]pyrimidine, imidazo[1,2-a]pyridine, pyrrolo[3,2-b]pyridine, pyrrolo[3,2-c]pyridine, pyrrolo[3,2-b]quinoline or pyrrolo[2,3-b]pyrazine.

In another aspect, the present invention is directed to a method of inhibiting one or more protein kinase activity comprising the administration of a compound represented by the formula:

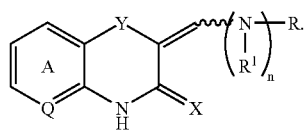

Ia and physiologically acceptable salts thereof, wherein:
A is substituted or unsubstituted;
Q is —N= or —CR$^2$=;
X is S, O, or NOR$^3$;
Y is —O—, —S—, —SO— or —SO$_2$—;
R and R$^1$ are each, independently, hydrogen or a substituted or unsubstituted aliphatic, aromatic, or aralkyl group;
R$^2$ is —H or a substitutent;
R$^3$ is —H or —C(O)R$^4$;
R$^4$ is a substituted or unsubstituted aliphatic, aromatic, or aralkyl group; and
n is an integer from 0 to 1.

A preferred method of the immediately foregoing method is where the compound is a mixture of stereoisomers.

A preferred method of the immediately foregoing method is where the stereoisomers are enantiomers.

A preferred method of the immediately foregoing method is where the stereoisomers are E and Z isomers.

A preferred method of any of the foregoing methods is where the compound is a mixture of structural isomers.

A preferred method of the immediately foregoing method is where the structural isomers are tautomers.

A preferred method of any of the foregoing methods is where said protein kinase is either a receptor tyrosine kinase or a non-receptor tyrosine kinase.

A preferred method of the immediately foregoing method is where said tyrosine kinase is selected from the group consisting of KDR, flt-1, TIE-2, Lck, Src, fyn, Lyn, Blk, and yes.

In another aspect the present invention is directed to a method of treating a hyperproliferative disorder in a recipient which comprises administering to said recipient an effective amount of a compound of formula Ia or a physiologically acceptable salt thereof.

In another aspect the present invention is directed to a method of affecting angiogenesis in a recipient which comprises administering to said recipient an effective amount of a compound of formula Ia or a physiologically acceptable salt thereof. Preferred is where the angiogenesis affect in said recipient is an anti-angiogenic affect.

In another aspect, the present invention is directed to a method of treating a disease in a mammal in need thereof, wherein said disease is selected from the group consisting of cancer, arthritis, atherosclerosis, psoriasis, hemangioma, myocardial angiogenesis, coronary and cerebral collateral vascularization, ischemic limb angiogenesis, corneal disease, rubeosis, neovascular glaucoma, macular degeneration, retinopathy of prematurity, wound healing, ulcers, *Helicobacter* related diseases, fractures, endometriosis, diabetic retinopathy, cat scratch fever, thyroid hyperplasia, burns, trauma, acute lung injury, chronic lung disease, stroke, polyps, cysts, synovitis, chronic and allergic inflammation, ovarian hyperstimulation syndrome, pulmonary and cerebral edema, keloid, fibrosis, cirrhosis, carpal tunnel syndrome, sepsis, adult respiratory distress syndrome, multiple-organ dysfunction syndrome, ascites and tumor-associated effusions and edema, comprising the step of administering a compound of formula Ia as described hereinabove or a physiologically acceptable salt thereof.

In another aspect, the present invention is directed to a method of inhibiting vascular hyperpermeability or the production of edema in a recipient which comprises administering to said recipient an effective amount of a compound of formula Ia or physiologically acceptable salts thereof.

A preferred method of any of the foregoing methods is where said protein kinase is a serine kinase.

A preferred method of any of the foregoing methods is where said protein kinase is a threonine kinase.

In yet another aspect, the present invention provides a compound represented by following structural formula:

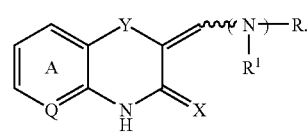

Ib and physiologically acceptable salts thereof, wherein:
ring A is substituted or unsubstituted;
Q is —N= or —CR$^2$=;
X is S, O, or NOR$^3$;
Y is —O—, —S—, —SO— or —SO$_2$—;
R$^2$ is —H or a substituent;
R$^3$ is —H or —C(O)R$^4$;
R$^4$ is a substituted or unsubstituted aliphatic or aromatic group;
n is 0 or 1;
when X is S or NOR$^3$, R is a substituted or unsubstituted aromatic or aralkyl group and R$^1$ is hydrogen or a substituted or unsubstituted aliphatic group;
when X is O and n is 0, R$^1$ is hydrogen or a substituted or unsubstituted aliphatic group and R is a substituted or unsubstituted aromatic or aralkyl group, provided that R is not thiophenyl, benzoxadiazolyl, 3-furanyl, 3-pyridinyl or

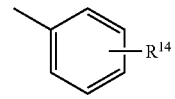

where R$^{14}$ is H, CF$_3$, phenyl, —OCH$_3$, —O-phenyl, NO$_2$ or —OC(O)CH$_3$; and
when X is O and n is 1, R$^1$ is H or a substituted or unsubstituted aliphatic group and R is a substituted or unsubstituted aromatic or aralkyl group, provided that R is not

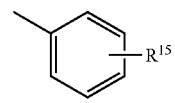

where R$^{15}$ is H, Cl, CH$_3$ or CF$_3$

A preferred compound of formula Ib is where the aromatic group and the aromatic portion of the aralkyl group defined for R is a heteroaryl group.

A preferred compound of formula Ib is where n is 0 and R is selected from the group consisting of substituted or unsubstituted indole, pyrrole, 7-azaindole, pyrazole, imidazole and indazole.

A preferred compound of formula Ib is where n is 1 and R is selected from the group consisting of substituted or unsubstituted indole, pyrazolyl, phenyl, triazolyl, pyridyl and indazolyl.

A preferred compound of any of the foregoing compounds is where Q is $CH_2$; Y is O or S; and R is selected from the group consisting of substituted or unsubstituted pyrrole, pyrazole, imidazole, oxazole, isoxazole, thiazole, isothiazole, triazole, tetrazole, indole, 7-azaindole, indazole, purine, pyrrolo-pyrimidine, pyrazolo-pyrimidine, imidazo-pyridine, imidazo-pyrimidine, imidazo-pyridine, pyrrolo-pyridine, pyrrolo-pyridine, pyrrolo-quinoline, pyrrolo-pyrazine, 6,7,8,9-tetrahydropyrido-indole and tetrahydrofuran.

A preferred compound of any of the foegoing compounds is wherein R is selected from the group consisting of substituted or unsubstituted pyrrole, pyrazole, imidazole, oxazole, isoxazole, thiazole, isothiazole, triazole, tetrazole, indole, 7-azaindole, indazole, purine, pyrrolo[2,3-d]pyrimidine, pyrazolo[3,4-d]pyrimidine, imidazo[4,5-b]pyridine, imidazo[1,2-a]pyrimidine, imidazo[1,2-a]pyridine, pyrrolo[3,2-b]pyridine, pyrrolo[3,2-c]pyridine, pyrrolo[2,3-c]pyridine, pyrrolo[3,2-b]quinoline, pyrrolo[2,3-b]pyrazine, 6,7,8,9-tetrahydropyrido[1,2-a]indole, and tetrahydrofuran.

A preferred compound of any of the foregoing compounds is where R is optionally substituted with one or more moieties selected from the group consisting of halogens, trihalomethyl, cyano, hydroxy, nitro, $-NR^5R^6$, carbamoyl, carboxy carboxamidoxime, $-SO_2NR^5R^6$, $-NHSO_2R^5$, $R^7-O-R^8-$, $R^7-O-R^8-O-R^9-$, $R^{11}-$, $R^{11}O-$, $R^{11}OC(O)-$, $R^{11}N(R^5)C(O)-$, $R^{11}C(O)-$, $R^{11}C(O)O-$, $R^{11}S-$, $R^{11}S(O)-$, $R^{11}S(O)_2-$, $(R^5R^6)NC(O)-$, $R^{11}(R^5)NC(O)N(R^5)-$, $R^{11}C(O)N(R^5)-$, $R^{12}(CH_2)_m-$, $R^{12}(CH_2)_mC(O)N(R^5)-$, $R^{12}(CH_2)_mO-$, $R^{12}(CH_2)_mN(R^5)-$, $[R^{12}(CH_2)_m]_2CH-O-(CH_2)_m-$, $R^{12}(CH_2)_mOC(O)-$, $R^{12}(CH_2)_mN(R^5)C(O)-$, $R^{12}(CH_2)_mCH(R^{12})(CH_2)_m-$, $R^{12}(CH_2)_mC(O)O-$, $R^{12}(CH_2)_mN(R^5)C(O)O-$, $R^{12}(CH_2)_mOC(O)N(R^5)-$, $R^{12}(CH_2)_mOC(O)O-$, $R^{12}(CH_2)_mN(R^5)C(O)(CH_2)_m-$, $R^{12}(CH_2)_mOC(O)(CH_2)_m-$, $R^{12}(CH_2)_m(CR^5R^6)_m(CH_2)_mN(R^5)(CH_2)_m-$, $R^{12}(CH_2)_mC(O)-$, $R^{12}C(O)(CH_2)_m-$, $R^{12}(CH_2)_m(CR^5R^6)_m(CH_2)_mN(R^5)C(O)(CH_2)_m-$, $R^{12}(CH_2)_m(CR^5R^6)_m(CH_2)_mN(R^5)(CH_2)_mC(O)-$, $[R^{12}(CH_2)_m]_2NC(O)(CH_2)_m-$, $R^{12}(CH_2)_mC(O)-$, $R^{12}(CH_2)_m(CR^5R^6)_m(CH_2)_mN(R^5)SO_2-$, $R^{12}(CH_2)_m(CR^5R^6)_m(CH_2)_mO(CH_2)_m-$, wherein:

$R^5$ and $R^6$ for each occurrence are each independently selected from the group consisting of hydrogen, a lower alkyl, benzyl, heteroarylmethyl and aryl group optionally substituted with a halogen, cyano or hydroxy group;

$R^7$ for each occurrence is independently selected from the group consisting of hydrogen, $R^{10}C(O)-$, a lower alkyl and an aryl group optionally substituted with one or more halogens, cyano, hydroxy or $-NR^5R^6$;

$R^8$ and $R^9$ for each occurrence are each independently selected from the group consisting of $-C(O)-$, a lower alkyl or an aryl group optionally substituted with one or more halogens, cyano, hydroxy or $-NR^5R^6$;

$R^{10}$ for each occurrence is independently selected from a group consisting of a lower alkyl and an aryl group optionally substituted with one or more halogens, cyano, hydroxy or $-NR^5R^6$;

$R^{11}$ for each occurrence is independently hydrogen or selected from an optionally substituted group consisting of a lower alkyl group, a saturated or unsaturated heterocyclic ring, an aryl group and an aralkyl group, where said groups are optionally substituted with one or more halogens, cyano, hydroxy or $-NR^5R^6$;

$R^{12}$ for each occurrence is independently selected from the group consisting of halogen, carboxy, carbamoyl, lower alkyloxycarbonyl, lower alkenyl, hydroxy, a lower alkyloxy, a lower alcanoyloxy, and $-NR^5R^6$; or is selected from an optionally substituted group consisting of morpholine, piperazine, piperidine, pyrrolidine, homopiperazine, pyridine, triazole, tetrazole, imidazole and tetrahydropyrane, where said groups are optionally substituted with one or more hydroxy, lower alkyl, lower alkyloxy, lower hydroxyalkyl, lower aminoalkyl, lower alkyloxyalkyl, a saturated or unsaturated heterocyclic ring, cycloalkyl or $-NR^5R^6$ group; and m for each occurrence is independently an integer from 0 to 4.

A preferred compound of any of the foregoing compounds is where X is O and n is 0.

A preferred compound of any of the foregoing compounds is where X is S.

A preferred compound of any of the foregoing compounds is where X is $NOR_3$.

In a particularly preferred embodiment, a preferred compound of any of the foregoing compounds is where R (or $R^{13}$ or $R^{17}$) is selected from the following substituents:

List I pyrrol-2-yl
5-methylpyrrol-2-yl
3,5-dimethylpyrrol-2-yl
4,5-dimethylpyrrol-2-yl
4-ethyl-3,5-dimethylpyrrol-2-yl
4-ethoxycarbonyl-3,5-dimethylpyrrol-2-yl
1-methylpyrrol-2-yl
1-(4-hydroxybutyl)pyrrol-2-yl
1-(2-hydroxyethyl)pyrrol-2-yl
1-(3-dimethylaminopropyl)pyrrol-2-yl
4-bromopyrrol-2-yl
1-[N-(2-morpholinoethyl)carbamoylmethyl]pyrrol-2-yl
1-(ethoxycarbonylmethyl)pyrrol-2-yl
1-(carboxymethyl)pyrrol-2-yl
1-[N-(3-dimethylaminopropyl)carbamoylmethyl]pyrrol-2-yl
1-[(4-methylpiperazin-1-yl)carbonylmethyl]pyrrol-2-yl
indol-3-yl
1-(4-hydroxybutyl)indol-3-yl
5-methoxyindol-3-yl
1-(2-hydroxyethyloxymethyl)indol-3-yl
1-(3-dimethylaminopropyl)indol-3-yl
6-methoxycarbonylindol-3-yl
2-methylindol-3-yl
1-methylindol-3-yl
1-isopropylindol-3-yl
1-(2-hydroxy-3-dimethylaminopropyl)indol-3-yl
5-hydroxyindol-3-yl
6-carboxyindol-3-yl
5-amino-2-methylindol-3-yl
6-(2-dimethylaminoethyloxycarbonyl)indol-3-yl
6-(2-morpholinoethyloxycarbonyl)indol-3-yl
6-(3-dimethylaminopropylcarbamoyl)indol-3-yl 1-(carbamoylmethyl)indol-3-yl
8-hydroxymethyl-6,7,8,9-tetrahydropyrido[1,2-a]indol-10-yl
1-(ethoxycarbonylmethyl)indol-3-yl
4-methoxycarbonylindol-3-yl
1-(2-ethoxycarbonylethyl)indol-3-yl
7-methoxycarbonylindol-3-yl
2-ethoxycarbonylindol-3-yl
1-cyclopentylindol-3-yl
1-(3-tetrahydrofuranyl)indol-3-yl
6-(N,N-dimethylaminosulfonyl)indol-3-yl
5-(acetylaminomethyl)indol-3-yl
1-(diethylcarbamoyl)indol-3-yl
5-hydroxy-1-methylindol-3-yl
6-methoxyindol-3-yl
6-hydroxyindol-3-yl
6-[2-(pyrrolidin-1-yl)ethyloxycarbonyl]indol-3-yl
6-(2-dimethylaminoethylxycarbonyl)-1-methylindol-3-yl
6-(3-dimethylaminopropyloxycarbonyl)indol-3-yl
6-carboxy-1-(2-hydroxyethyl)indol-3-yl
6-{N-[2-(pyrrolidin-1-yl)ethyl]carbamoyl}indol-3-yl
6-[N-(2-morpholinoethyl) carbamoyl]indol-3-yl
6-[N-(2-dimethylaminoethyl)carbamoyl]indol-3-yl
6-{N-[3-(4-methylpiperazin-1-yl)propyl]carbamoyl}indol-3-yl
6-{N-[2-(piperidin-1-yl)ethyl]carbamoyl}indol-3-yl
6-[N-(2-dimethylaminopropyl)carbamoyl]indol-3-yl
6-{[N-(2-dimethylaminoethyl)-N-methyl]carbamoyl}indol-3-yl
6-[(4-methylpiperazin-1-yl)carbonyl]indol-3-yl
5-[2-(piperidin-1-yl)ethyloxy]indol-3-yl
5-(3-dimethylaminopropyloxy)indol-3-yl
5-(2-morpholinoethyloxy)indol-3-yl
5-(3-dimethylaminopropyloxy)-1-(isopropyloxycarbonyl)indol-3-yl
5-(3-dimethylaminopropyloxy)-1-methylindol-3-yl
5-(2-morpholinoethyloxy)-1-methylindol-3-yl
5-[2-(pyrrolidin-1-yl)ethyloxy]indol-3-yl
5-(2-dimethylaminoethyloxy)indol-3-yl
6-(3-dimethylaminopropyloxy)indol-3-yl
6-(2-morpholinoethyloxy)indol-3-yl
6-[2-(piperidin-1-yl)ethyloxy]indol-3-yl
6-[2-(pyrrolidin-1-yl)ethyloxy]indol-3-yl
6-(2-dimethylaminoethyloxy)indol-3-yl
6-[(2-dimethylamino-2-methyl)propyloxy]indol-3-yl
6-[2-(1-methylpyrrolidin-2-yl)ethyloxy]indol-3-yl
6-[2-(1-methylpiperidin-3-yl)methyloxy]indol-3-yl
7-(dimethylaminomethyl)-6-hydroxyindol-3-yl
7-(dimethylaminomethyl)-6-(2-morpholinoethyloxy)indol-3-yl
2-methyl-5-(N'-ethylureido)indol-3-yl
2-methyl-5-(p-toluensulfonylamino)indol-3-yl
6-[(3-dimethylaminopropyl)aminomethyl]indol-3-yl
6-[(2-methoxyethyl)aminomethyl]indol-3-yl
1-(carboxymethyl)indol-3-yl
1-[N-(2-morpholinoethyl)carbamoylmethyl]indol-3-yl
1-[N-(2-methoxyethyl)carbamoylmethyl]indol-3-yl
1-[N-(3-dimethylaminopropyl)carbamoylmethyl]indol-3-yl
1-{N-(2-(2-pyridyl)ethyl) carbamoylmethyl}indol-3-yl
1-{N-[2-(pyrrolidin-1-yl)ethyl]carbamoylmethyl}indol-3-yl
7-[N-(3-dimethylaminopropyl)carbamoyl]indol-3-yl
1-[(4-methylpiperazin-1-yl)carbonylmethyl]indol-3-yl
1-[N,N-bis(2-N',N'-diethylaminoethyl)carbamoylmethyl]indol-3-yl
1-[(4-piperidinopiperidin-1-yl)carbonylmethyl]indol-3-yl
1-{[N-(2-N',N'-diethylaminoethyl)-N-methyl]carbamoylmethyl}indol-3-yl
7-carboxyindol-3-yl
7-[(4-methylpiperazin-1-yl)carbonyl]indol-3-yl
7-{[4-(2-hydroxyethyl)piperazin-1-yl]carbonyl}indol-3-yl
7-azaindol-3-yl
1-(4-hydroxybutyl)-7-azaindol-3-yl
1-(2-hydroxyethyloxymethyl)-7-azaindol-3-yl
1-(3-dimethylaminopropyl)-7-azaindol-3-yl
1-(2-morpholinoethyl)-7-azaindol-3-yl
1-(4-acetoxybutyl)-7-azaindol-3-yl
1-(2-hydroxyethyl)-7-azaindol-3-yl
1-methyl-7-azaindol-3-yl
1-methoxymethyl-7-azaindol-3-yl
1-(2-dimethylaminomethyl)-7-azaindol-3-yl
1-(ethoxycarbonylmethyl)-7-azaindol-3-yl
1-[N-(2-morpholinoethyl)carbamoylmethyl]-7-azaindol-3-yl
1-carboxymethyl-7-azaindol-3-yl
1-{N-[3-(4-methylpiperazin-1-yl)propyl]carbamoylmethyl}-7-azaindol-3-yl
1-[(4-methylpiperazin-1-yl)carbamoylmethyl]-7-azaindol-3-yl
1-{[N-(2-N',N'-diethylaminoethyl)-N-methyl]carbamoylmethyl}-7-azaindol-3-yl
1-{[N-(1-ethylpyrrolidin-2-yl)methyl]carbamoylmethyl}-7-azaindol-3-yl
1-[(4-methylhomopiperazin-1-yl)carbonylmethyl]-7-azaindol-3-yl
1-[(4-ethylpiperazin-1-yl)carbonylmethyl]-7-azaindol-3-yl
1-[(4-piperidinopiperidin-1-yl)carbonylmethyl]-7-azaindol-3-yl
1-[N,N-bis(2-N',N'-diethylaminoethyl)carbamoylmethyl]-7-azaindol-3-yl
7-benzyloxy pyrrolo[2,3-c]pyridin-5-yl
7-hydroxy pyrrolo[2,3-c]pyridin-5-yl
1-(2-dimethylaminoethyl)-7-hydroxy pyrrolo[2,3-c]pyridin-5-yl
imidazol-2-yl
4-trifluoromethylimidazol-2-yl
4-cyanoimidazol-2-yl
1-methyl-1H-benzo[d]imidazol-2-yl imidazol-5-yl
4(5)-methylimidazol-5(4)-yl
2-methylimidazol-5-yl
2-ethyl-4(5)-methylimidazol-5(4)-yl
3-(2-diethylaminoethyl)-4-methylimidazol-5-yl
1-(2-diethylaminoethyl)-4-methylimidazol-5-yl
1-(2-morpholinoethyl)-4-methylimidazol-5-yl
3-(2-morpholinoethyl)-4-methylimidazol-5-yl
1-methyl-2-methylthioimidazol-5-yl
4(5)-methoxycarbonylimidazol-5(4)-yl
4(5)-hydroxymethylimidazol-5(4)-yl
furan-3-yl
3-methylpyrazol-4-yl
3-phenylpyrazol-4-yl
1-(2-diethylaminoethyl)-3-methylpyrazol-4-yl
1-(2-diethylaminoethyl)-5-methylpyrazol-4-yl
1-(2-morpholinoethyl)-3-methylpyrazol-4-yl
1-(2-morpholinoethyl)-5-methylpyrazol-4-yl
1-methylpyrazol-4-yl
1-tert-butylpyrazol-4-yl
1-ethoxycarbonylmethyl-3-methylpyrazol-4-yl
1-ethoxycarbonylmethyl-5-methylpyrazol-4-yl
1-carboxymethyl-3-methylpyrazol-4-yl
1-carboxymethyl-5-methylpyrazol-4-yl
1-[N-(2-dimethylaminoethyl)carbamoylmethyl]-3-methylpyrazol-4-yl
1-{N-[3-(4-methylpiperazin-1-yl)propyl]carbamoylmethyl}-3-methylpyrazol-4-yl 1-[N-(2-dimethylaminoethyl)carbamoylmethyl]-5-methylpyrazol-4-yl
1-[N-(2-morpholinoethyl)carbamoylmethyl]-3-methylpyrazol-4-yl
1-[(4-piperidinopiperidin-1-yl)carbonylmethyl]-3-methylpyrazol-4-yl
1-{[N-(2-N',N'-diethylaminoethyl)-N-methyl]carbamoylmethyl}-3-methylpyrazol-4-yl
1-[(4-methylpiperazin-1-yl)carbonylmethyl]-5-methylpyrazol-4-yl
1-[(4-methylpiperazin-1-yl)carbonylmethyl]-3-methylpyrazol-4-yl
1-{N-[3-(imidazol-1-yl)propyl]carbamoylmethyl}-3-methylpyrazol-4-yl
1-{[4-(2-hydroxyethyl)piperazin-1-yl]carbonylmethyl}-5-methylpyrazol-4-yl
1-{[4-(2-(2-hydroxyethoxy)ethyl)piperazin-1-yl]carbonylmethyl}-5-methylpyrazol-4-yl
indol-2-yl
pyrrol-3-yl
indazol-3-yl
thiazol-2-yl
pyrazol-3-yl
5(3)-ethoxycarbonylpyrazol-3(5)-yl
5(3)-[N-(2-morpholinoethyl)carbamoyl]pyrazol-3(5)-yl
5(3)-[N-(2-methoxyethyl)carbamoyl]pyrazol-3(5)-yl
5(3)-{N-[2-(pyrrolidin-1-yl)ethyl]carbamoyl}pyrazol-3(5)-yl
5(3)-[N-(3-dimethylaminopropyl)carbamoyl]pyrazol-3(5)-yl
2-(dimethylamino)thiazol-5-yl indol-4-yl
3-(morpholinomethyl)indol-4-yl indol-7-yl
3-(dimethylaminomethyl)indol-7-yl
3-(morpholinomethyl)indol-7-yl
3-(piperidinomethyl)indol-7-yl
3-[(4-methylpiperazin-1-yl)methyl]indol-7-yl
3,5-dimethyl-4-dimethylaminomethylpyrrol-2-yl
4-carboxyimidazol-2-yl
7-{N-[3-(imidazol-1-yl)propyl]carbamoyl}indol-3-yl
7-{N-[3-(4-methylpiperazin-1-yl)propyl]carbamoyl}indol-3-yl
7-[N-(2-dimethylaminopropyl)carbamoyl]indol-3-yl
7-{N-[2-(pyrolidin-1-yl)ethyl]carbamoyl}indol-3-yl
7-[(4-ethylpiperazin-1-yl)carbonyl]indol-3-yl
7-[(4-methylhomopiperazin-1-yl)carbonyl]indol-3-yl
3-{[4-(2-hydroxyethyl)piperazin-1-yl]methyl}indol-7-yl
3-[(4-hydroxypiperidin-1-yl)methyl]indol-7-yl
1-[(piperazin-1-yl)carbonylmethyl]-7-azaindol-3-yl
1-[(piperazin-1-yl)carbonylmethyl]indol-3-yl
1-[(piperazin-1-yl)carbonylmethyl]-3-methyl-1H-pyrazol-4-yl
1-{N-[2-(pyrrolidin-1-yl)ethyl]carbamoylmethyl]-3-methyl-1H-pyrazol-4-yl
1-[N-(2-dimethylaminopropyl)carbamoylmethyl]-3-methyl-1H-pyrazol-4-yl
3-(2-dimethylaminoacetyl)indol-7-yl
6-[(2-morpholinoethyl)aminomethyl]indol-3-yl
6-{[2-(pyrrolidin-1-yl)ethyl]aminomethyl]}indol-3-yl
6-[(3-methoxycarbonylpropyl)oxy]indol-3-yl
6-{[(3-(4-methylpiperazin-1-yl)carbonyl]propyloxy}indol-3-yl
6-{3-[N-(2-dimethylaminoethyl)-N-methylcarbamoyl]propyloxy}indol-3-yl
6-[(2-hydroxyethyl)oxymethyloxy]indol-3-yl
6-{3-[(4-piperidinopiperidin-1-yl)carbonyl]propyloxy}indol-3-yl
6-{3-{[4-(2-hydroxyethyl)piperazin-1-yl]carbonyl}propyloxy}indol-3-yl
6-[(4-methylpiperazin-1-yl)methyl]indol-3-yl
6-{[N-(2-dimethylaminoethyl)-N-methyl]aminomethyl}indol-3-yl
7-(dimethylaminomethyl)-6-(2-methoxyethyloxy)indol-3-yl
7-(dimethylaminomethyl)-6-(3-methoxycarbonylpropyloxy)indol-3-yl
7-(dimethylaminomethyl)-6-{[3-(4-methylpiperazin-1-yl)carbonyl]propyloxy}indol-3-yl
7-(dimethylaminomethyl)-6-[(2-hydroxyethyl)oxymethyloxy]indol-3-yl
6-(2-methoxyethyloxy)-7-[(pyrrolidin-1-yl)methyl]indol-3-yl
6-{[3-(4-methylpiperazin-1-yl)carbonyl]propyloxy}-7-[(pyrrolidin-1-yl)methyl]indol-3-yl
6-[{2-(hydroxyethyl)oxymethyloxy]-7-[(pyrrolidin-1-yl)methyl]indol-3-yl
7-[[(pyrrolidin-1-yl)methyl]-6-{[2-(pyrrolidin-1-yl)ethyl]oxy}indol-3-yl
6-[2-(pyrrolidin-1-yl)ethyloxy]-7-azaindol-3-yl
6-(2-piperidinoethyloxy)-7-azaindol-3-yl
6-[(2-dimethylamino-2-methyl)propyloxy]-7-azaindol-3-yl
6[(2-hydroxyethyl)aminomethylcarbonyl]indol-3-yl
6-{[2-(pyrrolidin-1-yl)ethyl]aminomethylcarbonyl}indol-3-yl
6-[(2-diethylaminoethyl)aminomethylcarbonyl]indol-3-yl
4-carbamoylimidazol-2-yl
4(5)-methyl-2-(methylmercapto)imidazol-5(4)-yl
4(5)-methyl-2-(methylsulfonyl)imidazol-5(4)-yl
2-amino-4(5)-methylimidazol-5(4)-yl
4(5)-dimethylaminomethylimidazol-5(4)-yl
4(5)-methylaminomethylimidazol-5(4)-yl
4(5)-diethylaminomethylimidazol-5(4)-yl
6-(N-methylaminosulfonyl)indol-3-yl
6-[N-(3-dimethylaminopropyl)sulfonyl]indol-3-yl
6-{N-[2-(pyrrolidin-1-yl)ethyl]aminosulfonyl}indol-3-yl
6-{N-[2-piperidinoethyl]aminosulfonyl}indol-3-yl
6-{N-[2-morpholinoethyl]aminosulfonyl}indol-3-yl
6-{N-[2-(piperidinomethyl]aminosulfonyl}indol-3-yl
6-{N-[3-(4-methylpiperazin-1-yl)propyl]aminosulfonyl}indol-3-yl
7-[N-(2-morpholinoethyl)carbamoyl]indol-3-yl
7-[N-(2-piperidinoethyl)carbamoyl]indol-3-yl
7-{[N-(2-N',N'-diethylaminoethyl)-N-methyl]carbamoyl}indol-3-yl
7-[N-(2-methoxyethyl)carbamoyl]indol-3-yl
7-[(4-piperidinopiperidin-1-yl)carbonyl]indol-3-yl
7-[(piperazin-1-yl)carbonyl]indol-3-yl
7-{N-[(2,2,N',N'-tetramethyl)propyl]carbamoyl}indol-3-yl
7-{N-[(1-ethylpyrrolidin-2-yl)methyl]carbamoyl}indol-3-yl
7-{N-[2-(2-pyridyl)ethyl]carbamoyl}indol-3-yl
6-{N-[2-(2-pyridyl)ethyl]carbamoyl}indol-3-yl
6-[(4-piperidinopiperidin-1-yl)carbonyl]indol-3-yl
6-[(piperazin-1-yl)carbonyl]indol-3-yl
6-{N-[(2,2,N',N'-tetramethyl)propyl]carbamoyl}indol-3-yl
6-{N-[(1-ethylpyrrolidin-2-yl)methyl]carbamoyl}indol-3-yl
6-[(4-methylhomopiperazin-1-yl)carbonyl]indol-3-yl
6-[(4-butylpiperazin-1-yl)carbonyl]indol-3-yl
6-[(4-ethylpiperazin-1-yl)carbonyl]indol-3-yl
6-{[4-(2-(pyrrolidin-1-yl)ethyl)piperidin-1-yl]carbonyl}indol-3-yl
6-{[N-(3-dimethylamino)prop-2-yl]carbamoyl}indol-3-yl
6-[N-[3-(imidazol-1-yl)propyl]carbamoyl]indol-3-yl
6-{[4-(2-hydroxyethyl)piperazin-1-yl]carbonyl}indol-3-yl
3-[(4-ethylpiperazin-1-yl)methyl]indol-7-yl
3-[(pyrrolidin-1-yl)methyl]indol-7-yl 3-[(4-methylhomopiperazin-1-yl)methyl]indol-7-yl
3-(diethylaminomethyl)indol-7-yl
3-{[N-(2-N'N'-dimethylaminoethyl)-N-methyl]aminomethyl}indol-7-yl
3-[(4-piperidinopiperidin-1-yl)methyl]indol-7-yl
3-(2-piperidinoacetyl)indol-7-yl
3-[2-(pyrrolidin-1-yl)acetyl]indol-7-yl
3-(2-diethylaminoacetyl)indol-7-yl
3-[2-(4-methylpiperazin-1-yl)acetyl]indol-7-yl
3-[2-(4-methylhomopiperazin-1-yl)acetyl]indol-7-yl
3-(2-morpholinoacetyl)indol-7-yl
3-{2-[(2-methoxyethyl)amino]acetyl}indol-7-yl
3-{2-[(2-piperidinoethyl)amino]acetyl}indol-7-yl
3-{2-{[3-(imidazol-1-yl)propyl]amino}acetyl}indol-7-yl
6-[3-(carboxypropyl)oxy]indol-3-yl
6-{3-[(4-methylhomopiperazin-1-yl)carbonyl]propyloxy}indol-3-yl
6-[(2-homopiperidin-1-yl)ethyloxy]indol-3-yl
6-[(2-diethylamino-1-methyl)ethyloxy]indol-3-yl
6-{2-[(tetrahydropyran-2-yl)oxy]ethyloxy}indol-3-yl
6-[(2-hydroxyethyl)oxy]indol-3-yl
6-[2-(isopropyloxyl)ethyloxy]indol-3-yl
6-[2-(methoxyethyl)oxy]indol-3-yl
6-[(3-methoxypropyl)oxy]indol-3-yl
6-[(3-methoxybutyl)oxy]indol-3-yl
6-{[(N,N-diethylcarbamoyl)methyl]oxy}indol-3-yl
7-[2-(piperidin-1-yl)ethyloxy]indol-3-yl
7-[(2-homopiperidin-1-yl)ethyloxy]indol-3-yl
7-[(2-diethylamino-1-methyl)ethyloxy]indol-3-yl
7-{2-[(tetrahydropyran-2-yl)oxy]ethyloxy}indol-3-yl
7-[(2-hydroxyethyl)oxy]indol-3-yl
7-[2-(isopropyloxyl)ethyloxy]indol-3-yl
7-[2-(methoxyethyl)oxy]indol-3-yl
7-[(3-methoxypropyl)oxy]indol-3-yl
7-[(3-methoxybutyl)oxy]indol-3-yl
7-{[(N,N-diethylcarbamoyl)methyl]oxy}indol-3-yl
7-(dimethylaminomethyl)-6-[(2-piperidin-1-yl)ethyloxy]indol-3-yl
7-(dimethylaminomethyl)-6-[(2-homopiperidin-1-yl)ethyloxy]indol-3-yl
7-(dimethylaminomethyl)-6-{2-[(tetrahydropyran-2-yl)oxy]ethyloxy}indol-3-yl
7-(dimethylaminomethyl)-6-[(2-hydroxyethyl)oxy]indol-3-yl
7-(dimethylaminomethyl)-6-[2-(isopropyloxyl)ethyloxy]indol-3-yl
7-(dimethylaminomethyl)-6-[2-(methoxyethyl)oxy]indol-3-yl
7-(dimethylaminomethyl)-6-[(3-methoxypropyl)oxy]indol-3-yl
7-(dimethylaminomethyl)-6-[(3-methoxybutyl)oxy]indol-3-yl
7-[(pyrrolidin-1-yl)methyl]-6-[(2-piperidin-1-yl)ethyloxy]indol-3-yl
7-[(pyrrolidin-1-yl)methyl]-6-[(2-homopiperidin-1-yl)ethyloxy]indol-3-yl
7-[(pyrrolidin-1-yl)methyl]-6-{2-[(tetrahydropyran-2-yl)oxy]ethyloxy}indol-3-yl
7-[(pyrrolidin-1-yl)methyl]-6-[(2-hydroxyethyl)oxy]indol-3-yl
7-[(pyrrolidin-1-yl)methyl]-6-[2-(isopropyloxyl)ethyloxy]indol-3-yl
7-[(pyrrolidin-1-yl)methyl]-6-[2-(methoxyethyl)oxy]indol-3-yl
7-[(pyrrolidin-1-yl)methyl]-6-[(3-methoxypropyl)oxy]indol-3-yl
7-[(pyrrolidin-1-yl)methyl)]-6-[(3-methoxybutyl)oxy]indol-3-yl
6-[(2-homopiperidin-1-yl)ethyloxy]-7-azaindol-3-yl
6-[(2-diethylamino-1-methyl)ethyloxy]-7-azaindol-3-yl
6-{2-[(tetrahydropyran-2-yl)oxy]ethyloxy}-7-azaindol-3-yl
6-[(2-hydroxyethyl)oxy]-7-azaindol-3-yl
6-[2-(isopropyloxyl)ethyloxy]-7-azaindol-3-yl
6-[2-(methoxyethyl)oxy]-7-azaindol-3-yl
6-[(3-methoxypropyl)oxy]-7-azaindol-3-yl
6-[(3-methoxybutyl)oxy]-7-azaindol-3-yl
6-{[(N,N-diethylcarbamoyl)methyl]oxy}-7-azaindol-3-yl
6-{4-(2-hydroxyethyl)piperazin-1-yl]methyl}indol-3-yl
6-[(4-methylhomopiperazin-1-yl)]methylindol-3-yl
6-[(4-piperidinopiperidin-1-yl)methyl]indol-3-yl
6-{[3-(isopropyloxy)propyl]aminomethyl}indol-3-yl
6-{[3,3-bis(ethyloxy)propyl]aminomethyl}indol-3-yl
6-[(2,2-dimethyl-1,3-dioxolane-4-methane)aminomethyl]indol-3-yl
6-{3-[(2-methoxyethyl)oxypropyl]aminomethyl}indol-3-yl
6-{[3-(ethyloxy)propyl]aminomethyl}indol-3-yl
6-[3-(butyloxy)propyl]aminomethyl]indol-3-yl
6-[(3-methoxypropyl)aminomethyl]indol-3-yl
6-(chloromethylcarbonyl)indol-3-yl
6-[2-(isopropyloxyethyl)aminomethylcarbonyl]indol-3-yl
6-{[(2-piperidin-1-yl)ethyl]aminomethylcarbonyl}indol-3-yl
6-{[(2-homopiperidin-1-yl)ethyl]aminomethylcarbonyl}indol-3-yl
6-{4-(2-hydroxyethyl)piperazin-1-yl]methylcarbonyl}indol-3-yl
6-{[(4-methylhomopiperazin-1-yl)]methyl}carbonylindol-3-yl
6-[(4-piperidinopiperidin-1-yl)methylcarbonyl]indol-3-yl
6-{[3-(isopropyloxy)propyl]aminomethylcarbonyl}indol-3-yl
6-{[3,3-bis(ethyloxy)propyl]aminomethylcarbonyl}indol-3-yl
6-[(2,2-dimethyl-1,3-dioxolane-4-methane)aminomethylcarbonyl]indol-3-yl
6-{3-[(2-methoxyethyl)oxypropyl]aminomethylcarbonyl}indol-3-yl
6-{[3-(ethyloxy)propyl]aminomethylcarbonyl}indol-3-yl
6-[3-(butyloxy)propyl]aminomethylcarbonyl]indol-3-yl
6-[(3-methoxypropyl)aminomethylcarbonyl]indol-3-yl.

In another embodiment, the compounds of the invention are represented by the formula

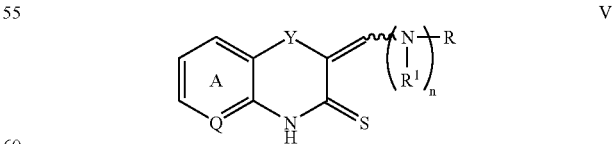

V and physiologically acceptable salts thereof, wherein ring A is substituted or unsubstituted. Q, Y, R, $R^1$, and n are defined as above.

In yet another embodiment, the compounds of the invention are represented by the formula

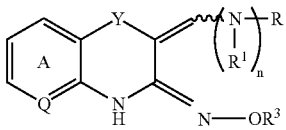

VI and physiologically acceptable salts thereof, wherein ring A is substituted or unsubstituted; Q, Y, R, $R^1$, $R^3$ and n are defined as above.

In another aspect, the present invention is directed to a method of inhibiting one or more protein kinase activity in a recipient which comprises administering to said recipient any of the foregoing compounds. Preferred is where the compound is a mixture of stereoisomers; even more preferred is where the stereoisomers are enantiomers and most preferred is where the stereoisomers are E and Z isomers. Also preferred is where the compound is a mixture of structural isomers; and more preferred is where the structural isomers are tautomers.

A preferred method of any of the foregoing methods is where said tyrosine kinase is selected from the group consisting of KDR, flt-1, TIE-2, Lck, Src, fyn, Lyn, Blk, and yes.

A preferred method of any of the foregoing methods is where the activity of said tyrosine kinase affects hyperproliferative disorders.

A preferred method of any of the foregoing methods is where the activity of said tyrosine kinase affects angiogenesis.

In another aspect, the present invention provides a pharmaceutical composition comprising any of the compounds described hereinabove or a physiologically acceptable salt thereof and a pharmaceutically acceptable diluent or carrier.

Compounds of formula I may exist as salts with pharmaceutically acceptable acids. The present invention includes such salts. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. These salts may be prepared by methods known to those skilled in the art.

Certain compounds of formula I which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centres, and exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

The compounds of this invention are useful as inhibitors of serine/threonine and tyrosine kinases. In particular, compounds of this invention are useful as inhibitors of tyrosine kinases that are important in hyperproliferative diseases, especially in the process of angiogenesis. Since these compounds are anti-angiogenic, they are important substances for inhibiting the progression disease states where angiogenesis is an important component. Certain compounds of the invention are effective as inhibitors of such serine/threonine kinases as erk, cdks, Plk-1 or Raf-1. These compounds are useful in the treatment of cancer and hyperproliferative disorders.

The present invention provides a method of inhibiting the kinase activity of tyrosine kinases and serine/threonine kinases comprising the administration of a compound represented by formula I to said kinase in sufficient concentration to inhibit the enzyme activity of said kinase.

The present invention further includes the use of these compounds in pharmaceutical compositions with a pharmaceutically effective amount of the above-described compounds and a pharmaceutically acceptable carrier or excipient. These pharmaceutical compositions can be administered to individuals to slow or halt the process of angiogenesis in angiogenesis-aided diseases, or to treat edema, effusions, exudates, or ascites and other conditions associated with vascular hyperpermeability. Certain pharmaceutical compositions can be administered to individuals to treat cancer and hyperproliferative disorders by inhibiting serine/threonine kinases such as cdk, Plk-1, erk, etc.

DETAILED DESCRIPTION OF THE INVENTION

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

It is envisaged that the disorders listed above are mediated to a significant extent by protein tyrosine kinase activity involving the KDR/VEGFR-2 and/or the Flt-1/VEGFR-1 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 tyrosine kinases. Certain compounds of this invention also inhibit the activity of additional tyrosine kinases such as Flt-1/VEGFR-1, Src-subfamily kinases such as Lck, Src, fyn, yes, etc. Additionally, some compounds of this invention significantly inhibit serine/threonine kinases such as CDKs, Plk-1, or Raf-1 which play an essential role in cell-cycle progression. The potency and specificity of the generic compounds of this invention towards a particular protein kinase can often be altered and optimized by variations in the nature, number and arrangement of the substituents (i.e., $R_1$, $R_2$, $R_3$, $R_4$, $R_5$ and $R_6$) of and conformational restrictions. In addition the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278–1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Since Flt-1 tyrosine kinase activity may mediate important events in endothelial maintenance and vascular function, an inhibition of this enzyme activity may lead to toxic or adverse effects. At the very least, such inhibition is unnecessary for blocking the angiogenic responses, induction of vascular hyperpermeability and the formation of edema, so it is wasteful and of no value to the individual. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. The preferred compounds of this invention are, therefore, selective in their tyrosine kinase inhibitory activity.

The compounds of the present invention are also useful in the treatment of ulcers bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, psoriasis, Kaposi's sarcoma, protozoan infections and toxoplasmosis, endometriosis, ovarian hyperstimulation syndrome, preeclampsia, menometrorrhagia, systemic lupus, sarcoidosis, synovitis, Crohn's disease, sickle cell anaemia, Lyme's disease, pemphigoid, Paget's disease, hyperviscosity syndrome, Osler-Weber-Rendu disease, chronic inflammation, chronic occlusive pulmonary disease, asthma, rheumatoid arthritis and osteoarthritis, and edema following trauma, radiation, or stroke.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

The compounds of the present invention are also useful in the treatment of Crow-Fukase (POEMS) syndrome and diabetic conditions such as glaucoma, diabetic retinopathy and microangiopathy.

It is envisaged that the disorders listed above are mediated to a significant extent by protein tyrosine kinase activity involving the VEGF receptors (e.g. KDR and Flt-1). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula I as defined initially above (including the provisos) for use as medicaments, particularly as inhibitors of protein kinase activity for example tyrosine kinase activity, serine kinase activity and threonine kinase activity. In yet another aspect the present invention provides the use of compounds of formula I as defined initially above (including the provisos) in the manufacture of a medicament for use in the inhibition of protein kinase activity.

In this invention, the following definitions are applicable:

"Physiologically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

Pharmaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g. bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered topically and by using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the organic molecule compounds of the invention may be provided as salts with pharmaceutically compatible counterions. Pharmaceutically compatible salts may be formed with many acids, including but not limited to hydrochloric, sulfuric, maleic, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the in vitro or cellular $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

C) Enteric Coated Tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF, attenuate intracellular responses to VEGF, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, PKC inhibitors and PI3 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formula I as a medicament.

Both the Src and Syk families of kinases play pivotal roles in the regulation of immune function. The Src family currently includes Fyn, Lck, Fgr, Fes, Lyn, Src, Yes, Hck, and Blk. The Syk family is currently understood to include only Zap and Syk. The Janus family of kinases is involved in the transduction of growth factor and pro-inflammatory cytokine signals through a number of receptors. Although BTK and ITK, members of the Tec family of kinases, play a less well understood role in immunobiology, their modulation by an inhibitor may prove therapeutically beneficial. The kinases RIP, IRAK-1, IRAK-2, NIK, IKK-1 and IKK-2 are involved in the signal transduction pathways for the key pro-inflammatory cytokines TNF and IL-1. By virtue of their ability to inhibit one or more of these kinases, compounds of formula I may function as immunomodulatory agents useful for the maintenance of allografts and the treatment of autoimmune disorders. Through their ability to regulate T cell activation or the potentiation of an inflammatory process, these compounds could be used to treat such autoimmune diseases. Transplants due to rejection phenomena, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the Itk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and themselves may become oncogenic by over expression or mutation. By inhibiting the protein kinase activity of these proteins the disease process may be disrupted. Vascular restenosis may involve process of FGF and/or PDGF—promoted smooth muscle and endothelial cell proliferation. Inhibition of FGFr or PDGFr kinase activity may be an efficacious strategy for inhibiting this phenomenon. Thus compounds of formula I which inhibit the kinase activity of normal or aberrant c-kit, c-met, c-fms, src-family members, EGFr, erbB2, erbB4, BCR-Abl, PDGFr, FGFr, and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie) are essential for the stimulation of endothelial cell growth, migration, organization, differentiation and the establishment of the requisite new functional vasculature. As a result of the "vascular permeability factor" activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and HIV-Tat protein can also cause a vascular hyperpermeability response through the stimulation of a VEGFR kinase. Tie-2 is expressed also in a select population of hematopoietic stem cells in which it may play a role in their recruitment, adhesion, regulation and differentiation (*Blood* 89, 4317–4326 (1997)); this Tie-2 expressing population may serve as circulating angiogenic endothelial progenitors. Certain agents according to formula I capable of blocking the kinase activity of endothelial cell specific kinases could therefore inhibit disease progression involving these situations.

The compounds of formula I or a salt thereof or pharmaceutical compositions containing a therapeutically effective amount thereof may be used in the treatment of benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, and adult respiratory distress syndrome (ARDS).

The compounds of the present invention may also be useful in the prophylaxis of the above diseases.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., Nature. 373:536–539) by a test compound relative to control.

KDR Tyrosine Kinase Production Using Baculovirus System:

The coding sequence for the human KDR intra-cellular domain (aa789–1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6$ KDR(aa789–1354) were lysed by adding 50 ml of Triton X-100 lysis buffer (20 mM Tris, pH 8.0, 137 mM NaCl, 10% glycerol, 1% Triton X-100, 1 mM PMSF, 10 μg/ml aprotinin, 1 μg/ml leupeptin) to the cell pellet from 1L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at 80° C.

Human Tie-2 Kinase Production and Purification

The coding sequence for the human Tie-2 intra-cellular domain (aa775–1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 μl) and the EGF ligand was acquired from Oncogene Research Products/Calbiochem (Cat # PF011–100).

Expression of ZAP70

The baculoviral expression vector used was pVL1393. (Pharmingen, Los Angeles, Calif.) The nucleotide sequence encoding amino acids $M(H)_6$ $LVPR_9S$ was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The $LVPR_9S$ bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of Zap70

SF-9 cells were lysed in a buffer consisting of 20 mM Tris, pH 8.0, 137 mM NaCl, 10% glycerol, 1% Triton X-100, 1 mM PMSF, 1 μg/ml leupeptin, 10 μg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Lck source

Lck or truncated forms of Lck may be commercially obtained (e.g. from Upstate Biotechnology Inc. (Saranac Lake, N.Y.) and Santa Cruz Biotechnology Inc. (Santa Cruz, Calif.)) or purified from known natural or recombinant sources using conventional methods.

Enzyme Linked Immunosorbent Assay (ELISA) For PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology, 2d ed.*, edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly($Glu_4$ Tyr), 20,000–50,000 MW) was employed together with ATP (typically 5 µM) at concentrations approximately twice the apparent Km in the assay.

The following procedure was used to assay the inhibitory effect of compounds of this invention on KDR, Flt-1, Flt-4/VEGFR-3, Tie-2, EGFR and ZAP70 tyrosine kinase activity:

Buffers and Solutions:

PGT: Poly (Glu,Tyr) 4:1

Store powder at −20° C. Dissolve powder in phosphate buffered saline (PBS) for 50 mg/ml solution. Store 1 ml aliquots at −20° C. When making plates dilute to 250 µg/ml in Gibco PBS.

Reaction Buffer: 100 mM Hepes, 20 mM $MgCl_2$, 4 mM $MnCl_2$, 5 mM DTT, 0.02% BSA, 200 µM $NaVO_4$, pH 7.10

ATP: Store aliquots of 100 mM at −20° C. Dilute to 20 µM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 µg/ml. Add 125 µl per well of Corning modified flat bottom high affinity ELISA plates (Corning # 25805–96). Add 125 µl PBS to blank wells. Cover with sealing tape and incubate overnight 37° C. Wash 1× with 250 µl washing buffer and dry for about 2 hrs in 37° C. dry incubator. Store coated plates in sealed bag at 4° C. until used.

2. Tyrosine Kinase Reaction:

Prepare inhibitor solutions at a 4× concentration in 20% DMSO in water.

Prepare reaction buffer

Prepare enzyme solution so that desired units are in 50 µl, e.g. for KDR make to 1 ng/µl for a total of 50 ng per well in the reactions. Store on ice.

Make 4×ATP solution to 20 µM from 100mM stock in water. Store on ice

Add 50 µl of the enzyme solution per well (typically 5–50 ng enzyme/well depending on the specific activity of the kinase)

Add 25 µl 4× inhibitor

Add 25 µl 4×ATP for inhibitor assay

Incubate for 10 minutes at room temperature

Stop reaction by adding 50 µl 0.05N HCl per well

Wash plate

**Final Concentrations for Reaction: 5 µM ATP, 5% DMSO

3. Antibody Binding

Dilute 1 mg/ml aliquot of PY20—HRP (Pierce) antibody (a phosphotyrosine antibody) to 50 ng/ml in 0.1% BSA in PBS by a 2 step dilution (100×, then 200×)

Add 100111 Ab per well. Incubate 1 hr at room temp. Incubate 1 hr at 4C.

Wash 4× plate

4. Color reaction

Prepare TMB substrate and add 100 µl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot. For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit KDR kinase at concentrations of 50 micromolar or below. Some compounds of this invention also significantly inhibit other PTKs such as lck at concentrations of 50 micromolar or below.

Cdc2/Cyclin B Source

The human recombinant enzyme and assay buffer may be obtained commercially (New England Biolabs, Beverly, Mass. USA) or purified from known natural or recombinant sources using conventional methods.

Cdc2/Cyclin B Assay

The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 mM $MgCl_2$ (commercial buffer) supplemented with fresh 300 µM ATP (31 µCi/ml) and 30 µg/ml histone type IIIss final concentrations. A reaction volume of 80 µL, containing units of enzyme, was run for 20 minutes at 25 degrees C. in the presence or absence of inhibitor. The reaction was terminated by the addition of 120 µL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant.

Certain compounds of this invention significantly inhibit cdc2 at concentrations below 50 uM.

Pkc Kinase Source

The catalytic subunit of PKC may be obtained commercially (Calbiochem).

Pkc Kinase Assay

A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions were performed in a kinase buffer consisting of 50 mM Tris-HCl pH7.5, 10mM MgCl$_2$, 2 mM DTT, 1 mM EGTA, 100 µM ATP, 8 µM peptide, 5% DMSO and $^{33}$P ATP (8Ci/mM). Compound and enzyme were mixed in the reaction vessel and the reaction initiated by addition of the ATP and substrate mixture. Following termination of the reaction by the addition of 10 µL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction was carried out in a buffer consisting of 50 mM Tris pH 7.5, 1mM EGTA, 2 mM DTT, 0.01% Brij, 5% DMSO and 10 mM MgCl$_2$ (commercial buffer) supplemented with fresh 100 µM ATP (31 µCi/ml) and 30 µM myelin basic protein under conditions recommended by the supplier. Reaction volumes and method of assaying incorporated radioactivity were as described for the PKC assay (vide supra).

In Vitro Models for T-cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically 10$^5$ responders are mixed with 5×10$^4$ stimulators and plated (200 µl volume) in a U bottom microtiter plate (Costar Scientific). The cells are cultured in RPMI 1640 supplemented with either heat inactivated fetal bovine serum (Hyclone Laboratories) or pooled human AB serum from male donors, 5×10$^{-5}$ M 2-mercaptoethanol and 0.5% DMSO, The cultures are pulsed with 0.5 µof $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 µg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α(TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 µg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at 6×10$^6$ per ml in tissue culture medium (RPMI 1640 supplemented with heat inactivated fetal bovine serum (Hyclone Laboratories) 5×10$^{-5}$M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model:J. Immunol 146 (4): 1163–8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol: 142(7):2237–2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should delay disease onset or reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333–58, 1992; Transplantation: 57(12): 1701–17D6, 1994) or heart (Am. J. Anat.: 113:273, 1963). Briefly, full thickness skin grafts are transplanted from C57BL/6 mice to BALB/c mice. The grafts are examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) were purchased from Clonetics (San Diego, Calif.) and cultured according to the manufacturer directions. Only early passages (3–8) were used for this assay. Cells were cultured in 100 mm dishes (Falcon for tissue culture; Becton Dickinson; Plymouth, England) using complete EBM media (Clonetics).
2. For evaluating a compound's inhibitory activity, cells were trypsinized and seeded at $0.5–1.0 \times 10^5$ cells/well in each well of 6-well cluster plates (Costar; Cambridge, Mass.).
3. 3–4 days after seeding, plates were 90–100% confluent. Medium was removed from all the wells, cells were rinsed with 5–10 ml of PBS and incubated 18–24h with 5 ml of EBM base media with no supplements added (i.e., serum starvation).
4. Serial dilutions of inhibitors were added in 1 ml of EBM media (25 μM, 5 μM, or 1 μM final concentration to cells and incubated for one hour at 37 C. Human recombinant $VEGF_{165}$ (R & D Systems) was then added to all the wells in 2 ml of EBM medium at a final concentration of 50 ng/ml and incubated at 37 C for 10 minutes. Control cells untreated or treated with VEGF only were used to assess background phosphorylation and phosphorylation induction by VEGF.

All wells were then rinsed with 5–10 ml of cold PBS containing 1 mM Sodium Orthovanadate (Sigma) and cells were lysed and scraped in 200 μl of RIPA buffer (50 mM Tris-HCl pH7, 150 mM NaCl, 1% NP-40, 0.25% sodium deoxycholate, 1 mM EDTA) containing protease inhibitors (PMSF 1 mM, aprotinin 1 μg/ml, pepstatin 1 μg/ml, leupeptin 1 μg/ml, Na vanadate 1 mM, Na fluoride 1 mM) and 1 μg/ml of Dnase (all chemicals from Sigma Chemical Company, St Louis, Mo.). The lysate was spun at 14,000 rpm for 30 min, to eliminate nuclei.

Equal amounts of proteins were then precipitated by addition of cold (−20 C) Ethanol (2 volumes) for a minimum of 1 hour or a maximum of overnight. Pellets were reconstituted in Laemli sample buffer containing 5%-mercaptoethanol (BioRad; Hercules, Calif.) and boiled for 5 min. The proteins were resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4 C. After washing and incubating for 1 hour with HRP conjugated $F(ab)_2$ of goat anti-rabbit or goat-anti-mouse IgG the bands were visualized using the emission chemiluminescence (ECL) system (Amersham Life Sciences, Arlington Height, Ill.). Certain examples of the present invention significantly inhibit cellular VEGF-induced KDR tyrosine kinase phosphorylation at concentrations of less than 50 μM.

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones were purchased from Sigma (St. Louis, Mo.) or Cal Biochem (La Jolla, Calif.) as lyophilized powders and prepared according to supplier instructions.

Vehicle components (DMSO, Cremaphor EL) were purchased from Sigma (St. Louis, Mo.).

Mice (Balb/c, 8–12 weeks old) were purchased from Taconic (Germantown, N.Y.) and housed in a pathogen-free animal facility in accordance with institutional Animal Care and Use Committee Guidelines.

Method:

Day 1: Balb/c mice were given an intraperitoneal (i.p.) injection of 15 units of pregnant mare's serum gonadotropin (PMSG).

Day 3: Mice received 15 units of human chorionic gonadotropin (hCG) i.p.

Day 4: Mice were randomized and divided into groups of 5–10. Test compounds were administered by i.p., i.v. or p.o. routes depending on solubility and vehicle at doses ranging from 1–100 mg/kg. Vehicle control group received vehicle only and two groups were left untreated.

Thirty minutes later, experimental, vehicle and 1 of the untreated groups were given an i.p. injection of 17-estradiol (500 μg/kg). After 2–3 hours, the animals were sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri were blotted to remove fluid by pressing between two sheets of filter paper with a one liter glass bottle filled with water. Uteri were weighed following blotting (blotted weight). The difference between wet and blotted weights was taken as the fluid content of the uterus. Mean fluid content of treated groups was compared to untreated or vehicle treated groups. Significance was determined by Student's test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear "marble" of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. Biol. (1995), 15(11), 1857–6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

EXEMPLIFICATIONS

The core structure of the compounds of the invention was synthesized via a base catalyzed aldol condensation followed by an elimination reaction. Scheme I is a general representation of this reaction.

Scheme I
General synthesis of common core structure

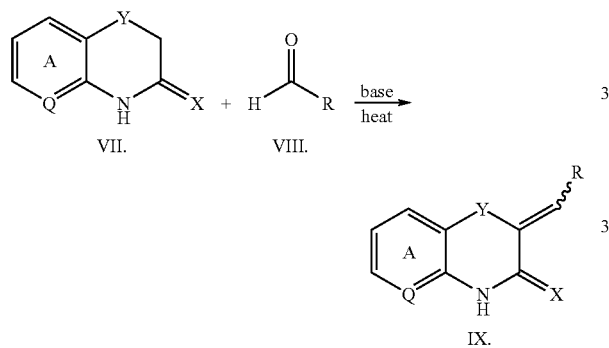

Alternatively, the core structure of the compound of the invention was synthesized via a Wadsworth-Emmons reaction, as represented in Scheme II.

Scheme II
General synthesis of common core structure

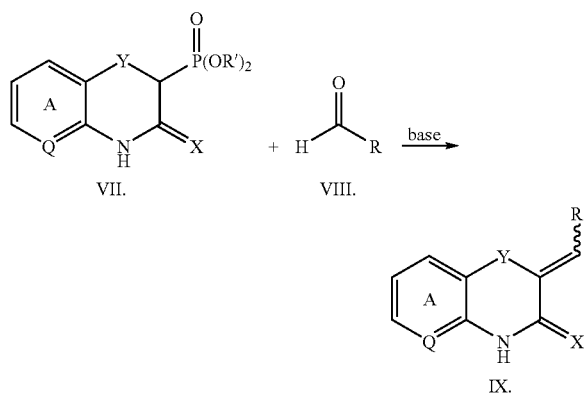

I. (Pyrrol-2-yl)methylene Benzothiazinones (XI).

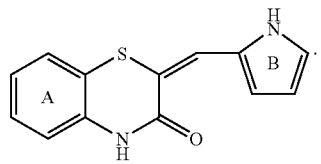

The following (pyrrol-2-yl)methylene benzothiazinones (Examples 1–25) were synthesized according to Schemes I and/or II.

Example 1

Synthesis of (Z)-2-[(Pyrrol-2-yl)methylene]-2H-1,4-benzothiazin-3(4H)-one

Sodium methoxide (0.28 g, 5.2 mmol) was added to a solution of 2H-1,4-benzothiazin-3(4H)-one (0.60 g, 4 mmol) and pyrrol-2-carboxaldehyde (0.49 g, 5.2 mmol) in dry N,N-dimethylformamide (3.5 ml) (hereinafter "DMF"). The mixture was heated at 120° C. for 6.5 h, allowed to cool and poured into water (60 ml). The precipitate was collected by filtration and washed with water. The precipitate was dissolved in ethyl acetate and the insoluble black residue was filtered out. The filtrate was concentrated, then chromatographed on a silica column using a gradient of 100% dichloromethane to (100:1) dichloromethane:ethanol as the mobile phase. The first eluted product was the (E)-isomer.

Example 12

Synthesis of (Z)-7-Amino-2-[(pyrrol-2-yl)methylene]-2H-1,4-benzothiazin-3(4H)one A catalytic amount of Raney nickel was added portionwise with stirring to a mixture of (Z)-7-nitro-2-[(pyrrol-2-yl)methylene]-2H-1,4-benzothiazin-3(4H)-one (Example 5) (0.43 g, 1.5 mmol) and hydrazine hydrate (98%) (0.8 ml) in ethanol (20 ml). The reaction mixture heated under reflux for 5.5 hours, then filtered and the solvent removed in vacuo. The product was purified by silica gel chromatography using a gradient of (98:2) to (95:5) toluene:ethanol as the mobile phase.

Example 13

Synthesis of 2-[(4,5-Dimethylpyrrol-2-yl)methylene]-2H-1,4-benzothiazin-3(4H)-one 4,5-Dimethylpyrrole-2-carboxaldehyde (0.27 g, 2.19 mmol) was added to a solution of 2H-1,4-benzothiazin-3(4H)-one (0.36 g, 2.19 mmol) and sodium methoxide (0.118 g, 2.19 mmol) in dry DMF (2 ml). The mixture was heated at 120° C. for 48 h, allowed to cool and poured into ice-water (50 ml). The precipitated solid was collected by filtration, washed with water, then dissolved in ethanol. The insoluble black residue was filtered out and the filtrate was concentrated to dryness under reduced pressure. The product was purified by silica gel chromatography using (98:2) dichloromethane:methanol as the mobile phase.

Example 17

Synthesis of (Z)-2-{[1-(4-hydroxybutyl)pyrrol-2-yl]methylene}-2H-1,4-benzothiazin-3(4H)-one Sodium methoxide (0.07 g, 1.3 mmol) was added to a solution of 2-diethylphosphonyl-2H-1,4-benzothiazin-3(4H)-one (0.30 g, 1.0 mmol) and 1-(4-hydroxybutyl)pyrrol-2-carboxaldehyde (0.17 g, 1.0 mmol) in methanol (4 ml). The mixture was stirred at room temperature for 48 h. The precipitate was collected by filtration and washed with cold methanol. Yield: 0.31 g (41%).

Example 24

Synthesis of 2-{[1-(N-(3-dimethylaminopropyl)carbamoylmethyl)pyrrol-2-yl]methylene}-2H-1,4-benzothiazin-3(4H)-one A mixture of 2-{[1-(ethoxycarbonylmethyl)pyrrol-2-yl]methylene}-2H-1,4-benzothiazin-3(4H)-one (example 21) (0.20 g, 0.6 mmol) and 3-dimethylamino propylamine (1.5 ml) was heated at 100° C. for 1 hour. After cooling, ethanol (5 ml) was added, the mixture was stirred and the precipitate was filtered off and washed with ethanol. Yield: 0.21 g.

Table 1 lists other compounds synthesized having structural formula XI. Examples 1–11 and 14–16 were synthesized as described in Example 1 using an appropriately substituted 2H-1,4-benzothiazin-3(4H)-one and an appropriately substituted pyrrole-2-carboxaldehyde. Example 12 required an additional hydrogenation step, which is described above. The reaction conditions in Example 13 differed slightly from those in Example 1, and therefore, they have also been described above. Examples 17–21 were synthesized as described in Example 17 using an appropriately substituted pyrrole-2-carboxaldehyde. Examples 23–25 were obtained from Example 21 and the appropriate amine as described in Example 24. Table 2 lists the physical data for compounds in Table 1.

TABLE 1

Compounds synthesized having structural formula XI.

| Example | Substituent on Ring A | Substituent on Ring B | Chromatographic Mobile Phase | % Yield (E)-Isomer | % Yield (Z)-Isomer |
|---|---|---|---|---|---|
| 1 | none | none | 100% CH$_2$Cl$_2$ to (100:1) CH$_2$Cl$_2$:EtOH | trace | 49 |
| 2 | 7-OCH$_3$ | none | 100% CH$_2$Cl$_2$ to (100:1) CH$_2$Cl$_2$:EtOH | 14 | 30 |
| 3 | 6-OCF$_3$ | none | 100% CH$_2$Cl$_2$ to (100:1) CH$_2$Cl$_2$:EtOH | 5 | 33 |
| 4 | 7-CH$_3$ | none | 100% CH$_2$Cl$_2$ to (100:1) CH$_2$Cl$_2$:EtOH | 5 | 42 |
| 5 | 7-NO$_2$ | none | 100% CH$_2$Cl$_2$ to (100:1) CH$_2$Cl$_2$:EtOH | 4 | 40 |
| 6 | 7-Cl | none | 100% CH$_2$Cl$_2$ to (100:1) CH$_2$Cl$_2$:EtOH | 4 | 60 |
| 7 | 6-Cl | none | 100% CH$_2$Cl$_2$ to (100:1) CH$_2$Cl$_2$:EtOH | 5 | 42 |
| 8 | 6-CH$_3$ | none | 100% CH$_2$Cl$_2$ to (100:1) CH$_2$Cl$_2$:EtOH | 6 | 24 |
| 9 | 7-OH | none | 100% CH$_2$Cl$_2$ to (100:1) CH$_2$Cl$_2$:EtOH | 1 | 23 |
| 10 | none | 5-CH$_3$ | (7:3) toluene:ethyl acetate | 3 | 62 |
| 11 | none | 3,5-dimethyl | (9:1) toluene:ethyl acetate | 3 | 10 |
| 12 | 7-NH$_2$ | none | (98:2) to (95:5) toluene:ethyl acetate | not applicable | 67 |
| 13 | none | 4,5-dimethyl | (98:2) CH$_2$Cl$_2$:CH$_3$OH | 9% as a mixture of isomers | 9% as a mixture of isomers |
| 14 | none | 4-ethyl-3,5-dimethyl | (95:5) Toluene:ethyl acetate | 40% as a mixture of isomers | 40% as a mixture of isomers |
| 15 | none | 4-ethoxy carbonyl-3,5-dimethyl | (9:1) to (8:2) Hexane:ethyl acetate | 11 | 32 |
| 16 | none | 1-methyl | NA | — | 88 |
| 17 | none | 1-(4-hydroxy-butyl) | NA | — | 41 |
| 18 | none | 1-(2-hydroxy-ethyl) | NA | — | 81 |
| 19 | none | 1-(3-dimethyl-amino-propyl) | NA | — | 71 |
| 20 | none | 4-bromo | NA | — | 92 |
| 21 | none | 1-ethoxy-carbonyl methyl | NA | — | 48 |
| 22 (potassium salt) | none | 1-carboxy-methyl | NA | — | 85 |
| 23 | none | 1-[N-(2-morpholino-ethyl)carbamoyl methyl] | NA | — | 88 |
| 24 | none | 1-[N-(3-dimethyl-amino-propyl)carbamoyl methyl] | NA | — | 91 |
| 25 | none | 1-[(4-methyl piperazin-1-yl)carbonyl-methyl] | NA | — | 52 |

TABLE 2

Physical data for compounds synthesized having structural formula XI.

| Example | Mp. (° C.) | Carbon calculated | Carbon found | Hydrogen calculated | Hydrogen found | Nitrogen calculated | Nitrogen found |
|---|---|---|---|---|---|---|---|
| 1 (E)-isomer | NA | NA | NA | NA | NA | NA | NA |
| 1 (Z)-isomer | 248–50 | 64.44 | 64.59 | 4.16 | 4.22 | 11.56 | 11.48 |
| 2 (E)-isomer | 190–2 | 61.75 | 61.52 | 4.44 | 4.48 | 10.29 | 10.13 |
| 2 (Z)-isomer | 258–60 | 61.75 | 62.02 | 4.44 | 4.48 | 10.29 | 10.04 |
| 3 (E)-isomer | 207–9 | 54.19 | 54.13 | 2.92 | 3.19 | 9.03 | 8.97 |
| 3 (Z)-isomer | 272–3 | 54.19 | 54.61 | 2.92 | 3.11 | 9.03 | 8.86 |
| 4 (E)-isomer | 211–2 | 65.60 | 65.30 | 4.72 | 4.43 | 10.93 | 10.82 |
| 4 (Z)-isomer | 248–9 | 65.60 | 65.68 | 4.72 | 4.80 | 10.93 | 10.86 |
| 5 (E)-isomer | 258–60 | 54.35 | 54.37 | 3.16 | 3.37 | 14.63 | 14.78 |
| 5 (Z)-isomer | 330–40 | 54.35 | 54.43 | 3.16 | 3.56 | 14.63 | 14.67 |
| 6 (E)-isomer | 243–6 | NA | NA | NA | NA | NA | NA |
| 6 (Z)-isomer | 244–5 | 56.42 | 56.47 | 3.28 | 3.13 | 10.12 | 9.92 |
| 7 (E)-isomer | 235–8 | NA | NA | NA | NA | NA | NA |
| 7 (Z)-isomer | 283–5 | 56.42 | 56.70 | 3.28 | 3.64 | 10.12 | 9.82 |
| 8 (E)-isomer | 220–2 | NA | NA | NA | NA | NA | NA |
| 8 (Z)-isomer | 275–7 | 65.60 | 65.97 | 4.72 | 4.72 | 10.93 | 10.65 |
| 9 (E)-isomer | 220–3 | NA | NA | NA | NA | NA | NA |
| 9 (Z)-isomer | 247–9 | 60.45 | 60.17 | 3.90 | 3.88 | 10.85 | 10.51 |
| 10 (E)-isomer | 211–13 | 65.60 | 65.46 | 4.72 | 4.44 | 10.93 | 10.48 |
| 10 (Z)-isomer | 226–8 | 65.60 | 66.02 | 4.72 | 4.92 | 10.93 | 10.72 |
| 11 (E)-isomer | 210–15 | 66.64 | 66.23 | 5.22 | 4.90 | 10.36 | 10.29 |
| 11 (Z)-isomer | 218–20 | 66.64 | 67.09 | 5.22 | 5.17 | 10.36 | 10.19 |
| 12 (Z)-isomer (0.2 EtOH)[1] | 225–30 | 60.39 | 60.41 | 4.61 | 4.58 | 15.76 | 15.75 |
| 13 mixture of isomers (0.1 toluene)[1] | 246–48 | 67.45 | 67.01 | 5.34 | 5.04 | 10.02 | 9.80 |
| 14 mixture of isomers | 170–184 | 68.43 | 68.58 | 6.08 | 6.10 | 9.39 | 9.50 |
| 15 (E)-isomer | 221–3 | 63.14 | 63/16 | 5.30 | 5.27 | 8.18 | 8.14 |
| 15 (Z)-isomer | 230–2 | 63.14 | 63.17 | 5.30 | 5.27 | 8.18 | 8.14 |
| 16 (Z)-isomer | 222–4 | 65.60 | 65.69 | 4.72 | 4.60 | 10.93 | 10.93 |
| 17 (Z)-isomer | 140–5 | 64.94 | 65.12 | 5.77 | 5.47 | 8.91 | 8.84 |
| 18 (Z)-isomer | 182 | 62.92 | 62.78 | 4.93 | 5.23 | 9.78 | 9.76 |
| 19 (Z)-isomer | 139–41 | 66.03 | 65.94 | 6.46 | 6.21 | 12.83 | 12.75 |
| 20 (Z)-isomer | >340 | 46.81 | 48.80 | 2.82 | 2.64 | 8.72 | 8.64 |

TABLE 2-continued

Physical data for compounds synthesized having structural formula XI.

| Example | Mp. (° C.) | Elemental analysis | | | | | |
|---|---|---|---|---|---|---|---|
| | | Carbon | | Hydrogen | | Nitrogen | |
| | | calculated | found | calculated | found | calculated | found |
| 21 (Z)-isomer | 195–7 | 62.18 | 62.23 | 4.91 | 4.95 | 8.53 | 8.48 |
| 22 (Z)-isomer(1 $H_2O$)[1] | 225–7 | 50.55 | 50.92 | 3.68 | 3.66 | 7.86 | 7.86 |
| 23 (Z)-isomer | 245–8 | 61.15 | 61.06 | 5.86 | 5.90 | 13.58 | 13.35 |
| 24 (Z)-isomer | 229–30 | 62.48 | 62.42 | 6.29 | 6.34 | 14.57 | 14.34 |
| 25 (Z)-isomer | 237–9 | 62.81 | 62.43 | 5.80 | 5.82 | 14.65 | 14.38 |

[1]The molecular weight calculated for the elemental analysis includes the solvent in the amount indicated.

II. (Indol-3-yl)methylene Benzothiazinones (XII).

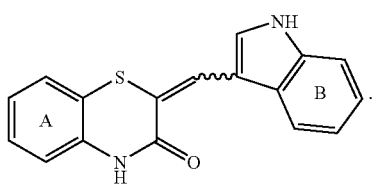

XII

The following (indol-3-yl)methylene benzothiazinones (Examples 26–122) were synthesized according to Schemes I and/or II.

Example 26

Synthesis of (Z)-2-[(Indol-3-yl)methylene]-2H-1,4-benzothiazin-3(4H)-one

A solution of 2H-1,4-benzothiazin-3(4H)-one (1.65 g, 10 mmol) and indole-3-carboxaldehyde (1.45 g, 10 mmol) in piperidine (30 ml) was heated under reflux for 5 days. The solvent was removed in vacuo, ethanol (20 ml) was added to the residue and the solid was filtered off. This solid was boiled in ethanol (20 ml) and filtered hot to give a yellow solid.

Example 28

2-[(indol-3-yl)methylene]-7-methyl-2H-1,4-benzothiazin-3(4H)-one

Sodium methoxide (0.28 g, 5.2 mmol) was added in one portion to a solution of 7-methyl-2H-1,4-benzothiazin-3 (4H)-one (0.72 g, 4.0 mmol) and indole-3-carboxaldehyde (0.88 g, 6.0 mmol) in dry DMF (4 mL). The mixture was heated for 48 h at 140° C., allowed to cool, then poured into water (60 ml). The precipitate was collected by filtration and washed with water. The precipitate was then refluxed with toluene (100 ml) and filtered hot to give a yellow solid which was purified by silica gel chromatography using a gradient of (100:1) to (100:20) toluene:ethanol as the mobile phase.

Example 39 (salt)

Synthesis of 2-{[1-(N,N-Dimethyl-3-aminopropyl) indol-3-yl]methylene}-2H-1,4-benzothiazin-3(4H)-one methanesulfonate Methanesulfonic acid (0.127 g, 1.3 mmol) was added to a suspension of 2-{[1N,N-dimethyl-3-aminopropyl)indol-3-yl]methylene}-2H-1,4-benzothiazin-3 (4H)-one (Example 36) (0.5 g, 1.3 mmol) in dry dichloromethane (40 ml). The mixture was stirred at room temperature overnight, and the precipitated solid was collected by filtration, washed with dichloromethane and diethylether, then dried under nitrogen to give the product.

Example 40

Synthesis of 7-Hydroxy-2-[(indol-3-yl)methylene]-2H-1,4-benzothiazin-3(4H)-one

Sodium methoxide (0.54 g, 10 mmol) was added in one portion to a solution of 7-hydroxy-2H-1,4-benzothiazin-3 (4H)-one (0.91 g, 5 mmol) and indole-3-carboxaldehyde (1.09 g, 7.5 mmol) in dry DMF (5 ml). The mixture was heated at 140° C. for 48 h, allowed to cool and poured into ice water (60 ml). The solid was collected by filtration. The filtrate was acidified to pH=2 with 10% hydrochloric acid and the precipitated solid was collected by filtration. Both precipitates were put together, boiled with toluene and filtered hot to give a solid which was purified by silica gel chromatography using a gradient of (9:1) to (8:2) n-hexane/ethanol as the mobile phase.

Example 41

Synthesis of 7-Amino-2-[(indol-3-yl)methylene]-2H-1,4-benzothiazin-3(4H)-one

A catalytic amount of Raney nickel was added portionwise with stirring to a mixture of 7-nitro-2-[(indol-3-yl) methylene]-2H-1,4-benzothiazin-3(4H)-one (see Example 31) (0.39 g, 1.16 mmol) and hydrazine hydrate (98%) (0.60 ml) in ethanol (15 ml). The reaction mixture was refluxed for 5 h, then filtered hot. The solid residue was boiled with ethanol (100 ml) and filtered hot. The combined filtrates were brought to dryness in vacuo and chromatographed on silica gel using a gradient of (9:1) to (8:2) dichloromethane: ethanol as the mobile phase to afford 0.17 g (35%) product.

Example 42

Synthesis of 1-{3-Oxo-2-[(indol-3-yl)methylene]-2H-1,4-benzothiazin-7-yl}-3-tert-butyl urea A mixture of 7-amino-2-[(indol-3-yl)methylene]-2H-1,4-benzothiazin-3(4H)-one (see Example 38) (0.17 g, 0.55 mmol) and tert-butyl isocyanate (0.17 g, 1.75 mmol) in dry DMF (1 ml) was stirred at room temperature for 4 days. The reaction was poured into water (25 ml) and the precipitated solid was collected by filtration. The precipitate was purified by silica gel chromatography using a gradient of (9:1) to (4:6) toluene:ethyl acetate as the mobile phase.

Example 60

Synthesis of 2-{[1-(Carbamoylmethyl)indol-3-yl]methylene}-2H-1,4-benzothiazin-3(4H)-one Sodium methoxide (0.12 g, 2.22 mmol) was added to a mixture of 2-diethylphosphonyl-2H-1,4-benzothiazin-3 (4H)-one (0.30 g, 1.0 mmol) and 1-carbamoylmethylindole-3-carboxaldehyde (0.20 g, 1.0 mmol) in methanol (20 ml). The reaction mixture was heated at reflux for 6 hours. After cooling, the precipitate was filtered and washed with methanol and water. Yield: 0.24 g (69%).

Example 75

Synthesis of (Z)-2-{{6-[2-(Pyrrolidin-1-yl)ethyloxycarbonyl]indol-3-yl}-3-yl}methylene}-2H-1,4-benzothiazin-3(4H)-one To a solution of (Z)-2-[(6-carboxyindol-3-yl)methylene]-2H-1,4-benzothiazin-3(4H)-one (0.5 g, 1.5 mmol) in dry N,N-dimethylformamide (30 ml), 1,1'-carbonyldiimidazol (0.24 g, 1.5 mmol) was added under nitrogen atmosphere, and the mixture was heated at 40° C. for 1 h. Then N-(2-hydroxyethyl)pyrrolidine (0.34 g, 2.95 mmol) and DBU (1,8-diazabicyclo[5,4,0]undec-7-ene (0.23 ml, 1.5 mmol) were added, and the resulting mixture heated at the same temperature for an additional time of 5 h. The reaction was allowed to cool to room temperature and poured into ice/water. The precipitated solid was filtered off, washed with water and cristallized from N,N-dimethylformamide/water to yield 0.44 g (68%) of the entitled product.

Example 79

Synthesis of (Z)-2-{{6-{N-[2-(Pyrrolidin-1-yl)ethyl]carbamoyl}indol-3-yl}methylene}-2H-1,4-benzothiazin-3 (4H)-one To a solution of (Z)-2-[(6-carboxyindol-3-yl)methylene]-2H-1,4-benzothiazin-3(4H)-one (0.5 g, 1.5 mmol) in dry N,N-dimethylformamide (30 ml), 1,1'-carbonyldiimidazol (0.24 g, 1.5 mmol) was added under nitrogen atmosphere, and the mixture was heated at 40° C. for 1 h. Then N-(2-aminoethyl)pyrrolidine (0.34 g, 2.98 mmol) was added and the mixture heated at the same temperature for an additional time of 20 h. The reaction was allowed to cool to room temperature and the solvent removed under reduced pressure. The residue was treated with water and the yellow precipitate was crystallized from N,N-dimethylformamide/water to yield 0.31 g (48%) of the entitled product.

Example 87

Synthesis of (Z)-2-{{5-[2-(Piperidin-1-yl)ethyloxy]indol-3-yl}methylene}-2H-1,4-benzothiazin-3(4H)-one To a solution of (Z)-2[(5-hydroxyindol-3-yl)methylene]-2H-1,4-benzothiazin-3(4H)-one (1.00 g, 3.24 mmol) and 1,1'-(azodicarbonyl)dipiperidine (1.23 g, 4.87 mmol) in dry tetrahydrofurane-(40 ml), tributylphosphine (0.98 g, 4.87 mmol) was added under nitrogen atmosphere keeping the mixture at 0–5° C. After 5 min N-(2-hydroxyethyl)piperidine (0.63 g, 4.88 mmol) was added at the same temperature. The cooling bath was removed and the mixture stirred at room temperature for 48 h. Then the solvent was removed under reduced pressure and the residue chromatographed (silica gel, eluent, ethyl acetate:ethanol (90:10) to (80:20)) to yield 0.2 g (22%) of the entitled product.

Table 3 lists other compounds synthesized having structural formula X. Examples described in Table 3 were synthesized by the method indicated therein. Table 4 lists the physical data for compounds in Table 3.

TABLE 3

Compounds synthesized having structural formula XII.

| Example | Substituent on Ring A | Substituent on Ring B | Chromatographic Mobile Phase | % Yield | Method |
|---|---|---|---|---|---|
| 26 | none | none | NA | 14 | see Example 26 |
| 27 | 7-Cl | none | NA | 18 | see Example 26 |
| 28 | 7-CH$_3$ | none | (100:1) to (100:20) toluene:ethanol | 44 | see Example 28 |
| 29 | 6-CF$_3$ | none | (100:1) to (100:20) toluene:ethanol | 83 | see Example 28 |
| 30 | 6-CH$_3$ | none | (100:1) to (100:20) toluene:ethanol | 36 | see Example 28 |
| 31 | 6-Cl | none | (100:1) to (100:20) toluene:ethanol | 42 | see Example 28 |
| 32 | 7-OCH$_3$ | none | (100:1) to (100:20) toluene:ethanol | 27 | see Example 28 |
| 33 | 6-acetylamino | none | (100:1) to (100:20) toluene:ethanol | 35 | see Example 28 |
| 34 | 7-NO$_2$ | none | (100:1) to (100:20) toluene:ethanol | 42 | see Example 28 |
| 35 | 7-acetylamino | none | 95:5 ethylacetate:ethanol | 21 | see Example 28 |
| 36 | none | 1-(4-hydroxybutyl) | 98:2 dichloromethane:ethanol | 34 | see Example 28 |
| 37 | none | 5-OCH$_3$ | (100:1) to (100:20) toluene:ethanol | 56 | see Example 28 |
| 38 | none | 1-(2-hydroxyethyloxymethyl) | 95:5 toluene:ethanol | 30 | see Example 28 |
| 39 | none | 1-(N,N-dimethyl-3-aminopropyl) | (100:1) to (100:20) toluene:ethanol | 77 | see Example 28 |

TABLE 3-continued

Compounds synthesized having structural formula XII.

| Example | Substituent on Ring A | Substituent on Ring B | Chromatographic Mobile Phase | % Yield | Method |
|---|---|---|---|---|---|
| 39 (salt) | none | 1-(N,N-dimethyl-3-aminopropyl) | NA | 81 | see Example 39 (salt) |
| 40 | 7-OH | none | (9:1) to (8:2) n-hexane:ethanol | 27 | see Example 40 |
| 41 | 7-NH$_2$ | none | (9:1) to (8:2) dichloromethane:ethanol | 35 | see Example 41 |
| 42 | 7-(3-tert-butyl) urea | none | (9:1) to (4:6) toluene:ethylacetate | 50 | see Example 42 |
| 43 | none | 6-methoxycarbonyl | (100:1) to (100:20) toluene:ethanol | 41 | see Example 28 |
| 44 | none | 2-CH$_3$ | (8:2) toluene:ethanol | 13 | see example 28 |
| 45 | 7-OH | 1-(2-hydroxyethyloxymethyl) | (2:8) toluene:ethyl acetate | 5 | see example 28 |
| 46 | none | 1-CH$_3$ | NA | 46 | see example 28 |
| 47 | none | 1-isopropyl | 100% CH$_2$Cl$_2$ to (95:5) CH$_2$Cl$_2$:ethyl acetate | 59 | see example 28 |
| 48 | none | 1-(2-hydroxy-N,N-dimethyl-3-aminopropyl) | (95:5) to (7:3) toluene-ethanol | 14 | see example 28 |
| 49 | 7-benzoyl amino | none | NA | 32 | * |
| 50 | 7-chloroacetyl amino | none | (7:3) to (7:2) CH$_2$Cl$_2$:ethyl acetate | 66 | * |
| 51 | 7-(morpholin-4-yl) acetylamino | none | NA | 67 | * |
| 52 | 7-propenoyl amino | none | (100:3) CH$_2$Cl$_2$:methanol | 53 | * |
| 53 | 7-[3-morpholin-4-yl) propionamido] | none | (100:3) to (100:5) CH$_2$Cl$_2$:ethanol | NA | * |
| 54 | none | 5-hydroxy | (95:5) to (7:3) toluene:ethanol | 80 | * |
| 55 | none | 6-carboxy | NA | 45 | * |
| 56 | none | 5-amino-2-methyl | (95:5) Cl$_2$CH$_2$:methanol | 73 | * |
| 57 | none | 6-(2-Dimethyl-aminoethyl oxycarbonyl) | (9:1) to (8:2) CH$_2$Cl$_2$:methanol | 12 | see example 75 |
| 58 | none | 6-(2-morpholino ethyloxy-carbonyl) | (9:1) CH$_2$Cl$_2$:ethanol | 25 | see example 75 |
| 59 | none | 6-(3-dimethyl-aminopropyl carbamoyl) | NA | 50 | see example 79 |
| 60 | none | 1-carbamoyl methyl | NA | 69 | see example 60 |
| 61 | none | 1,2-(3-hydroxy-methyl) tetra-methylene | NA | 39 | see example 60 |
| 62 | none | 1-ethoxy-carbonyl methyl | NA | 47 | see example 17 |
| 63 | none | 4-methoxy-carbonyl | NA | 78 | see example 60 |
| 64 | none | 1-(2-ethoxy-carbonyl ethyl) | NA | 49 | see example 17 |
| 65 | none | 7-methoxy carbonyl | NA | 61 | see example 17 |
| 66 | none | 2-ethoxy-carbonyl | NA | 66 | see example 17 |
| 67 | none | 1-cyclopentyl | NA | 52 | see example 60 |
| 68 | none | 1-(3-tetrahydro furanyl) | NA | 59 | see example 60 |
| 69 | none | 6-N,N-dimethyl amino-sulfonyl | NA | 72 | see example 17 |
| 70 | none | 5-acetyl aminomethyl | (95:5) to (80:20) dichloromethane:ethanol | 25 | see example 60 |
| 71 | none | 1-(diethyl carbamoyl) | (95:5) toluene:ethanol | 27 | see example 60 |
| 72 | none | 5-hydroxy-1-methyl | NA | 85 | see example 60 |
| 73 | none | 6-methoxy | NA | 86 | see example 60 |
| 74 | none | 6-hydroxy | NA | 78 | * |
| 75 | none | 6-[2-(pyrrolidin-1-yl) ethyloxy carbonyl] | NA | 68 | see example 75 |
| 76 | none | 6-(2-dimethyl-amino ethyloxy carbonyl)-1-methyl | (90:10) to (80:20) Cl$_2$CH$_2$:methanol | 3 | see example 75 |
| 77 | none | 6-(3-dimethyl-amino propyloxy carbonyl) | (40:60) Cl$_2$CH$_2$:methanol | 64 | see example 75 |
| 78 sodium salt | none | 6-carboxy-1-(2-hydroxy-ethyl) | NA | 46 | see example 75 |
| 79 | none | 6-{N-[2-(pyrrolidin-1-yl)ethyl] carbamoyl} | NA | 48 | see example 79 |
| 80 | none | 6-[N-(2-morpholino-ethyl) carbamoyl] | (95:5) Cl$_2$CH$_2$:methanol | 40 | see example 79 |
| 81 | none | 6-[N-(2-dimethyl-amino ethyl) carbamoyl] | (80:20) Cl$_2$CH$_2$:methanol | 10 | see example 79 |
| 82 | none | 6-{N-[3-(4-methylpiperazin-1-yl) propyl] carbamoyl} | NA | 73 | see example 79 |

TABLE 3-continued

Compounds synthesized having structural formula XII.

| Example | Substituent on Ring A | Substituent on Ring B | Chromatographic Mobile Phase | % Yield | Method |
|---|---|---|---|---|---|
| 83 | none | 6-{N-[2-(piperidin-1-yl)ethyl]carbamoyl} | NA | 64 | see example 79 |
| 84 | none | 6-[N-(2-dimethylaminopropyl)carbamoyl] | NA | 33 | see example 79 |
| 85 | none | 6-{N-[2-(dimethylaminoethyl)-N-methyl]carbamoyl} | NA | 38 | see example 79 |
| 86 | none | 6-[(4-methylpiperazin-1-yl)-carbonyl] | NA | 53 | see example 79 |
| 87 | none | 5-[2-(piperidin-1-yl)ethyloxy] | (90:10) to (80:20) ethyl acetate:ethanol | 22 | see example 87 |
| 88 | none | 5-(3-dimethylaminopropyloxy) | (90:10) Cl$_2$CH$_2$:methanol | 12 | see example 87 |
| 89 | none | 5-(2-morpholinoethyloxy) | (95:5) toluene:ethanol | 44 | see example 87 |
| 90 | none | 5-(3-dimethylaminopropyloxy)-1-(isopropyloxycarbonyl) | (90:10) Cl$_2$CH$_2$:methanol | 5 | see example 87 |
| 91 | none | 5-(3-dimethylaminopropyloxy)-1-methyl | (90:10) Cl$_2$CH$_2$:methanol | 28 | see example 87 |
| 92 | none | 5-(2-morpholinoethyloxy)-1-methyl | (80:20) to (0:100) hexane:ethylacetate | 28 | see example 87 |
| 93 | none | 5-[2-(pyrrolidin-1-yl)ethyloxy] | (100:0) to (0:100) ethyl acetate:methanol | 21 | see example 87 |
| 94 | none | 5-(2-dimethylaminoethyloxy) | (95:5) to (0:100) ethyl acetate:ethanol | 27 | see example 87 |
| 95 | none | 6-(3-dimethylaminopropyloxy) | (85:15) Cl$_2$CH$_2$:methanol | 28 | see example 87 |
| 96 | none | 6-(2-morpholinoethyloxy) | (100:0) to (95:5) ethyl acetate:ethanol | 43 | see example 87 |
| 97 | none | 6-[2-(piperidin-1-yl)ethyloxy] | (90:10) to (60:40) toluene:methanol | 28 | see example 87 |
| 98 | none | 6-(2-(pyrrolidin-1-yl)ethyloxy | (100:0) to 60:40 ethyl acetate:methanol | 22 | see example 87 |
| 99 | none | 6-(2-dimethylaminoethyloxy) | (100:0) to (50:50) ethyl acetate:ethanol | 45 | see example 87 |
| 100 | none | 6-[(2-dimethylamino-2-methyl)propyloxy] | (95:5) ethyl acetate:ethanol | 46 | see example 87 |
| 101 | none | 6-[2-(1-methylpyrrolidin-2-yl)ethyloxy] | (100:0) to (0:100) ethyl acetate:methanol | 30 | see example 87 |
| 102 | none | 6-[2-(1-methylpiperidin-3-yl)methyloxy | (100:0) to (80:20) ethyl acetate:ethanol | 39 | see example 87 |
| 103 | none | 7-(dimethylaminomethyl)-6-hydroxy | NA | 92 | * |
| 104 | none | 7-(dimethylaminomethyl)-6-(2-morpholinoethyloxy) | (90:10) to (70:30) Cl$_2$CH$_2$:methanol | 31 | * |
| 105 | none | 2-methyl-5-(N'-ethylureido) | NA | 74 | * |
| 106 | none | 2-methyl-5-(p-toluensulfonylamino) | (98:2) Cl$_2$CH$_2$:methanol | 18 | * |
| 107 | none | 6-[(3-dimethylaminopropyl)aminomethyl] | (40:60:10) Cl$_2$CH$_2$:methanol:NH$_4$OH | 23 | see example 60 |
| 108 | none | 6-[(2-methoxyethyl)aminomethyl] | NA | 6.5 | see example 60 |
| 109 | none | 1-carboxymethyl | NA | 58 | * |
| 110 | none | 1-[N-(2-morpholinoethyl)carbamoylmethyl] | NA | 59 | see example 24 |
| 111 | none | 1-[N-(2-methoxyethyl)carbamoylmethyl] | NA | 83 | see example 24 |
| 112 | none | 1-[N-(3-dimethylaminopropyl)carbamoylmethyl] | NA | 76 | see example 24 |
| 113 | none | 1-[N-(2-(2-pyridyl)ethyl)carbamoylmethyl] | NA | 83 | see example 24 |
| 114 | none | 1-{N-[2-(pyrrolidin-1-yl)ethyl]carbamoylmethyl} | NA | 67 | see example 24 |
| 115 | none | 7-[N-(3-dimethylaminopropyl)carbamoyl] | (1:1) dichloromethane:methanol | 55 | see example 79 |

TABLE 3-continued

Compounds synthesized having structural formula XII.

| Example | Substituent on Ring A | Substituent on Ring B | Chromatographic Mobile Phase | % Yield | Method |
|---|---|---|---|---|---|
| 116 | none | 1-(4-methylpiperazin-1-yl)carbonylmethyl | NA | 63 | see example 79 |
| 117 | none | 1-[N,N-bis(2-N',N'-diethylaminoethyl)carbamoylmethyl] | (60:40) to (40:60) ethyl acetate:methanol | 44 | see example 79 |
| 118 | none | 1-(4-piperidinopiperidin-1-yl)carbonylmethyl | (95:5) to (90:10) dichloromethane:methanol | 50 | see example 79 |
| 119 | none | 1-[N-(2-N'N'-diethylaminoethyl)-N-methyl]carbamoylmethyl | NA | 91 | see example 79 |
| 120 | none | 7-carboxy | NA | 85 | * |
| 121 | none | 7-(4-methylpiperazin-1-yl)carbonyl | (95:5) dichloromethane:methanol | 23 | see example 79 |
| 122 | none | 7-[4-(2-hydroxyethyl)piperazin-1-yl]carbonyl | (95:5) dichloromethane:methanol | 17 | see example 79 |

* These compounds were obtained from the corresponding (indol-3-yl)methylene benzothiazinones already described by methods well known for those skilled in the art.

TABLE 4

Physical data for compounds synthesized having structural formula XII.

| Example | Mp. (° C.) | Carbon calculated | Carbon found | Hydrogen calculated | Hydrogen found | Nitrogen calculated | Nitrogen found |
|---|---|---|---|---|---|---|---|
| 26 | >300 | 67.8 | 68.2 | 4.3 | 4.15 | 9.3 | 9.4 |
| 27 | >325 | 62.5 | 62.5 | 3.4 | 3.4 | 8.6 | 8.6 |
| 28 | 298–300 | 70.56 | 70.01 | 4.61 | 4.79 | 9.14 | 9.17 |
| 29 | 345–6 | 60.00 | 59.99 | 3.08 | 3.21 | 7.77 | 7.57 |
| 30 (0.25 H$_2$O)[1] | 303–5 | 69.54 | 69.43 | 4.70 | 4.49 | 9.01 | 8.99 |
| 31 (0.5 H$_2$O)[1] | >350 | 60.80 | 61.13 | 3.60 | 3.55 | 8.34 | 8.71 |
| 32 | 311–3 | 67.06 | 66.68 | 4.38 | 4.68 | 8.69 | 8.40 |
| 33 (1.0 H$_2$O)[1] | 330–4 | 62.11 | 62.31 | 4.66 | 4.55 | 11.44 | 11.27 |
| 34 | >350 | 60.53 | 59.89 | 3.29 | 3.63 | 12.46 | 12.38 |
| 35 | 275–7 | 65.31 | 65.06 | 4.33 | 4.50 | 12.03 | 12.01 |
| 36 (0.25 H$_2$O)[1] | 233–5 | 68.36 | 68.37 | 5.60 | 5.51 | 7.59 | 7.53 |
| 37 (0.2 DMF)[1] | 283–5 | 66.29 | 66.54 | 4.61 | 4.70 | 9.14 | 8.91 |
| 38 (0.5 H$_2$O)[1] | 210–2 | 63.98 | 64.34 | 5.10 | 5.01 | 7.46 | 7.31 |
| 39 | 185–7 | NA | NA | NA | NA | NA | NA |
| 39 (salt) (1.0 H$_2$O)[1] | 130–2 | 56.19 | 56.43 | 5.94 | 5.53 | 8.55 | 8.54 |
| 40 | 293–6 | 66.22 | 65.83 | 3.92 | 4.41 | 9.08 | 8.88 |
| 41 | 301–6 | 66.43 | 65.97 | 4.26 | 4.48 | 13.67 | 13.45 |
| 42 | >330 | 65.00 | 64.75 | 5.45 | 5.58 | 13.78 | 13.60 |
| 43 | 320–2 | 65.13 | 64.84 | 4.03 | 3.95 | 7.99 | 7.88 |
| 44 (0.2 ethyl acetate)[1] | 269–71 | 69.69 | 69.93 | 4.85 | 4.57 | 8.64 | 8.86 |
| 45 (0.25 H$_2$O)[1] | 230–2 | 62.08 | 62.05 | 4.82 | 4.66 | 7.24 | 7.16 |
| 46 | 264–6 | 70.56 | 70.83 | 4.61 | 4.78 | 9.14 | 8.97 |
| 47 | 182–4 | 71.83 | 71.46 | 5.43 | 5.64 | 8.38 | 8.16 |
| 48 (0.33 H$_2$O)[1] | 198–200 | 66.14 | 65.98 | 5.97 | 5.92 | 10.51 | 10.23 |
| 49 | >340 | 70.06 | 69.73 | 4.16 | 4.43 | 10.21 | 10.13 |
| 50 | 284–7 | 59.45 | 58.99 | 3.68 | 3.81 | 10.95 | 10.69 |
| 51 (0.8 H$_2$O)[1] | 260–2 | 61.54 | 61.55 | 5.30 | 5.29 | 12.48 | 12.31 |
| 52 | 262–75 | 66.47 | 66.02 | 4.18 | 4.09 | 11.63 | 11.50 |
| 53 (0.8 H$_2$O)[1] | 241–3 | 62.27 | 62.18 | 5.57 | 5.40 | 12.10 | 11.89 |

TABLE 4-continued

Physical data for compounds synthesized having structural formula XII.

| Example | Mp. (° C.) | Elemental analysis | | | | | |
|---|---|---|---|---|---|---|---|
| | | Carbon | | Hydrogen | | Nitrogen | |
| | | calculated | found | calculated | found | calculated | found |
| 54 | 306–8 | 66.21 | 65.92 | 3.92 | 4.21 | 9.08 | 8.86 |
| 55 (1.8 $H_2O$)[1] | >350 | 58.62 | 58.25 | 4.00 | 3.67 | 7.59 | 7.44 |
| 56 (0.5 $H_2O$)[1] | 242–4 | 65.43 | 65.88 | 4.88 | 4.88 | 12.71 | 13.05 |
| 57 | 255–6 | 64.85 | 64.92 | 5.19 | 5.27 | 10.31 | 9.94 |
| 58 | 310–1 | 64.12 | 63.78 | 5.15 | 5.44 | 9.35 | 9.47 |
| 59 | 279–81 | 65.69 | 65.28 | 5.75 | 5.62 | 13.32 | 13.16 |
| 60 | 330–3 | 65.31 | 64.95 | 4.33 | 4.53 | 12.03 | 11.91 |
| 61 (0.4 EtOH)[1] | 227–9 | 69.34 | 69.14 | 5.72 | 5.49 | 7.09 | 7.00 |
| 62 | 248–50 | 66.65 | 66.34 | 4.79 | 4.86 | 7.40 | 7.36 |
| 63 | 247–9 | 65.13 | 65.14 | 4.03 | 4.08 | 7.99 | 7.93 |
| 64 | 216–7 | 67.33 | 67.13 | 5.14 | 5.19 | 7.14 | 7.14 |
| 65 | 334–5 | 65.13 | 65.20 | 4.03 | 4.14 | 7.99 | 8.03 |
| 66 | 316–8 | 64.63 | 64.30 | 4.56 | 4.55 | 7.54 | 7.39 |
| 67 | 229–31 | 73.30 | 72.70 | 5.59 | 5.68 | 7.77 | 7.73 |
| 68 | 228–30 | 69.59 | 68.92 | 5.01 | 5.05 | 7.73 | 7.68 |
| 69 (0.3 $H_2O$)[1] | >320 | 56.36 | 56.29 | 4.45 | 4.35 | 10.37 | 10.28 |
| 70 | 262–3 | 66.10 | 65.63 | 4.71 | 4.86 | 11.56 | 11.39 |
| 71 (0.3 $H_2O$)[1] | 178–80 | 66.58 | 66.91 | 5.48 | 5.73 | 10.59 | 10.13 |
| 72 | 264–7 | 67.06 | 66.68 | 4.38 | 4.49 | 8.69 | 8.57 |
| 73 | 306–10 | 67.08 | 66.91 | 4.37 | 4.51 | 8.69 | 8.61 |
| 74 (0.1 $H_2O$)[1] | >335 | 66.21 | 65.67 | 3.92 | 4.27 | 9.08 | 9.38 |
| 75 | 278–80 | 65.81 | 65.80 | 5.41 | 5.52 | 9.59 | 9.66 |
| 76 (0.25 $H_2O$)[1] | 235–6 | 64.84 | 64.96 | 5.56 | 5.42 | 9.86 | 9.52 |
| 77 | 245–6 | 65.53 | 65.32 | 5.49 | 5.34 | 9.97 | 9.89 |
| 78 (2 $H_2O$)[1] | >350 | 54.79 | 55.05 | 4.36 | 3.99 | 6.38 | 6.28 |
| 79 (0.2 $H_2O$)[1] | 303–5 | 66.09 | 65.76 | 5.64 | 5.53 | 12.84 | 12.78 |
| 80 | 296–300 | 64.27 | 64.15 | 5.39 | 5.68 | 12.49 | 12.23 |
| 81 (1 $H_2O$)[1] | 285–7 | 62.24 | 62.17 | 5.69 | 5.55 | 13.19 | 12.80 |
| 82 | 270–2 | 64.44 | 64.10 | 6.24 | 6.15 | 14.45 | 14.63 |
| 83 | 314–5 | 67.24 | 66.81 | 5.87 | 5.98 | 12.54 | 12.61 |
| 84 (0.9 $H_2O$)[1] | 262–5 | 63.25 | 63.51 | 5.95 | 5.48 | 12.83 | 12.15 |
| 85 (0.2 $H_2O$)[1] | 162–5 | 65.13 | 64.87 | 5.80 | 5.93 | 13.21 | 13.38 |
| 86 (0.5 $H_2O$)[1] | 248–51 | 64.62 | 64.27 | 5.42 | 5.48 | 13.01 | 12.92 |
| 87 (0.1 $H_2O$)[1] | 261–3 | 68.41 | 68.17 | 6.03 | 6.03 | 9.97 | 10.02 |
| 88 (0.1 $H_2O$)[1] | 283–6 | 66.84 | 66.52 | 5.91 | 6.03 | 10.62 | 10.52 |
| 89 | 265–7 | 65.54 | 65.13 | 5.50 | 5.96 | 9.97 | 9.86 |
| 90 (0.25 $H_2O$)[1] | 197–9 | 64.51 | 64.21 | 6.14 | 6.13 | 8.68 | 8.64 |
| 91 (0.7 $H_2O$)[1] | 213–5 | 65.75 | 65.70 | 6.53 | 6.18 | 10.00 | 10.13 |
| 92 (0.25 $H_2O$)[1] | 211–3 | 65.51 | 65.71 | 5.84 | 5.88 | 9.55 | 9.39 |
| 93 (0.5 $H_2O$)[1] | 249–53 | 66.64 | 66.43 | 5.84 | 5.61 | 10.14 | 10.03 |
| 94 (1 $H_2O$)[1] | 236–8 | 63.45 | 63.23 | 5.83 | 5.66 | 10.57 | 10.48 |
| 95 (0.2 $H_2O$)[1] | 253–5 | 66.54 | 66.42 | 5.94 | 5.82 | 10.58 | 10.55 |
| 96 (0.25 $H_2O$)[1] | 232–5 | 64.84 | 64.72 | 5.56 | 5.69 | 9.86 | 9.72 |
| 97 | 249–50 | 68.71 | 68.35 | 6.01 | 6.12 | 10.01 | 9.97 |
| 98 (0.5 $H_2O$)[1] | 250–4 | 66.64 | 66.83 | 5.84 | 5.84 | 10.14 | 10.04 |
| 99 (0.5 $H_2O$)[1] | 266–8 | 64.93 | 64.71 | 5.71 | 5.61 | 10.82 | 10.63 |

TABLE 4-continued

Physical data for compounds synthesized having structural formula XII.

| Example | Mp. (° C.) | Elemental analysis | | | | | |
|---|---|---|---|---|---|---|---|
| | | Carbon | | Hydrogen | | Nitrogen | |
| | | calculated | found | calculated | found | calculated | found |
| 100 (0.25 H$_2$O)[1] | 244–6 | 67.04 | 66.67 | 6.24 | 6.37 | 10.20 | 10.10 |
| 101 (0.5 H$_2$O)[1] | 271–2 | 67.26 | 67.09 | 6.11 | 6.14 | 9.80 | 9.76 |
| 102 (0.25 H$_2$O)[1] | 250 (d) | 67.97 | 67.58 | 6.06 | 6.00 | 9.91 | 10.01 |
| 103 | 220 (d) | NA | NA | NA | NA | NA | NA |
| 104 (0.25 H$_2$O)[1] | 244–6 | 64.64 | 64.38 | 6.36 | 6.64 | 11.60 | 11.37 |
| 105 (1 H$_2$O)[1] | 230–5 | 61.44 | 61.72 | 5.40 | 5.07 | 13.65 | 13.46 |
| 106 (0.8 H$_2$O)[1] | 146–8 | 61.28 | 60.99 | 4.65 | 4.73 | 8.57 | 9.02 |
| 107 (0.5 H$_2$O)[1] | 190–4 | 66.48 | 66.54 | 6.55 | 6.49 | 13.48 | 13.27 |
| 108 | 220–4 | 66.47 | 66.27 | 5.58 | 5.70 | 11.07 | 10.90 |
| 109 | 290–4 | 65.13 | 64.59 | 4.03 | 4.28 | 7.99 | 8.18 |
| 110 | 259–60 | 64.91 | 64.72 | 5.67 | 5.69 | 12.11 | 12.01 |
| 111 | 289–91 | 64.85 | 64.70 | 5.19 | 5.27 | 10.31 | 10.34 |
| 112 | 260–1 | 66.33 | 66.21 | 6.03 | 6.10 | 12.89 | 12.71 |
| 113 | 282–5 | 68.70 | 68.42 | 4.88 | 5.00 | 12.33 | 12.39 |
| 114 | 255–65 | 67.24 | 67.45 | 5.87 | 5.94 | 12.55 | 12.40 |
| 115 (1 H$_2$O)[1] | 270–2 | 62.99 | 62.75 | 5.98 | 6.13 | 12.78 | 12.90 |
| 116 (0.25 H$_2$O)[1] | 246 | 65.96 | 65.71 | 5.65 | 5.60 | 12.82 | 12.70 |
| 117 | 180–2 | 67.98 | 67.59 | 7.55 | 7.51 | 12.79 | 12.70 |
| 118 (0.25 H$_2$O)[1] | 256–8 | 68.95 | 68.96 | 6.48 | 6.51 | 11.09 | 11.08 |
| 119 | 197–200 | 67.50 | 67.18 | 6.54 | 6.60 | 12.11 | 11.97 |
| 120 (0.1 DMF)[1] | >320 | 63.96 | 63.59 | 3.72 | 4.00 | 8.56 | 8.56 |
| 121 (0.5 H$_2$O)[1] | 233–7 | 64.62 | 64.85 | 5.42 | 5.36 | 13.10 | 13.05 |
| 122 (0.5 H$_2$O)[1] | 265–8 | 63.00 | 62.95 | 5.51 | 5.38 | 12.24 | 12.07 |

[1]The molecular weight calculated for the elemental analysis includes the solvent in the amount indicated.

III. (7-Azaindol-3-yl)methylene Benzothiazinones (XIII).

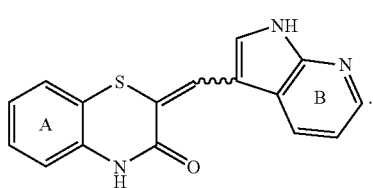

XIII

Example 131

Synthesis of 2-{[1-(4-Acetoxybutyl)-7-azaindol-3-yl]methylene}-2H-1,4-benzothiazine-3(4H)-one A mixture of 2-[(1-(4-hydroxybutyl)-7-azaindol-3-yl]methylene-2H-1,4-benzothiazin-3(4H)-one (0.58 g, 1.6 mmol) and acetic anhydride (20 ml) was heated at 100° C. for 10 min. After cooling, the reaction mixture was poured into ice water (75 ml) with stirring. The precipitate was collected by filtration and purified by silica gel chromatography using (8:2) ethyl acetate:hexane as the mobile phase.

Examples 123–209 from Tables 5–36 were synthesized by the method indicated therein, using an appropriately substituted 2H-1,4-benzothiazin-3(4H)-one and an appropriately substituted 7-azaindole-3-carboxaldehyde, pyrrolo[2,3-c]pyridin-5-carboxaldehyde, imidazole-2-carboxaldehyde, imidazole-5-carboxaldehyde, furan-3-carboxaldehyde, thiophene-3-carboxaldehyde, pyrazole-4-carboxaldehyde, indole-2-carboxaldehyde, pyrrole-3-carboxaldehyde, indazole-3-carboxaldehyde, thiazole-2-carboxaldehyde, pyrazole-3-carboxaldehyde, thiazole-5-carboxaldehyde, indole-4-carboxaldehyde or indole-7-carboxaldehyde. Methanesulfonic acid salts were formed as described in Example 39 (salt).

TABLE 5

Compounds synthesized having structural formula XIII.

| Example | Substituent on Ring A | Substituent on Ring B | Chromatographic Mobile Phase | % Yield | Method |
|---|---|---|---|---|---|
| 123 | none | 1-(4-hydroxybutyl) | (100:1) to (100:20) toluene:ethanol | 52 | see Example 28 |

TABLE 5-continued

Compounds synthesized having structural formula XIII.

| Example | Substituent on Ring A | Substituent on Ring B | Chromatographic Mobile Phase | % Yield | Method |
|---|---|---|---|---|---|
| 124 | 7-NO₂ | none | (100:1) to (100:20) toluene:ethanol | 34 | see Example 28 |
| 125 | 7-OH | none | (100:1) to (100:20) toluene:ethanol | 17 | see Example 28 |
| 126 | none | none | (100:1) to (100:20) toluene:ethanol | 56 | see Example 28 |
| 126 (salt) | none | none | NA | 87 | see Example 39 (salt) |
| 127 | none | 1-(2-hydroxy-ethyl-oxymethyl) | (95:5) dichloromethane:methanol | 19 | see Example 28 |
| 127 (salt) | none | 1-(2-hydroxy-ethyl-oxymethyl) | NA | 40 | see Example 39 (salt) |
| 128 | none | 1-(N,N-dimethyl-3-amino-propyl) | (100:1) to (100:20) toluene:ethanol | 49 | see Example 28 |
| 128 (salt) | none | 1-(N,N-dimethyl-3-amino-propyl) | NA | 52 | see Example 39 (salt) |
| 129 | none | 1-(2-morpholino ethyl) | (100:1) to (100:20) toluene:ethanol | 26 | see Example 28 |
| 129 (salt) | none | 1-(2-morpholino ethyl) | NA | 59 | see Example 39 (salt) |
| 130 | 7-(N,N-dimethyl-3-amino-propyloxy) | none | (100:1) to (100:20) toluene:ethanol | 37 | see Example 28 |
| 130 (salt) | 7-(N,N-dimethyl-3-amino-propyloxy) | none | NA | 69 | see Example 39 (salt) |
| 131 | none | 1-(4-acetoxy-butyl) | (8:2) ethyl acetate:n-hexane | 63 | see Example 131 |
| 132 | none | 1-(2-hydroxy ethyl) | (98:2) to (7:3) CH₂Cl₂:EtOH | 29 | see example 28 |
| 133 | none | 1-methyl | NA | 69 | see example 28 |
| 134 | none | 1-methoxy methyl | (98:2) to (80:20) toluene:ethanol | 80 | see example 60 |
| 135 | none | 1-(2-dimethyl amino-methyl) | NA | 45 | see example 60 |
| 136 | none | 1-ethoxy-carbonyl methyl | NA | 66 | see example 17 |
| 137 | none | 1-[N-(2-morpholino ethyl) carbamoyl methyl] | NA | 65 | see example 24 |
| 138 | none | 1-carboxy-methyl | NA | 51 | * |
| 139 | none | 1-[N-(3-(4-methyl piperazin-1-yl) propyl) carbamoyl methyl] | NA | 50 | see example 24 |
| 140 | none | 1-(4-methyl piperazin-1-yl)carbonylmethyl | (9:1) to (8:2) CH₂Cl₂:EtOH | 45 | see example 24 |
| 141 | none | 1-[N-(2-N',N'-diethyl-amino ethyl)-N-methyl] carbamoyl methyl | (7:3) to (0:10) ethyl acetate:methanol | 19 | see example 24 |
| 142 | none | 1-[N-(1-ethyl-pyrrolidin-2-yl)methyl] carbamoyl methyl | NA | 85 | see example 79 |
| 143 | none | 1-(4-methyl-homopiperazin-1-yl)carbonylmethyl | NA | 74 | see example 79 |
| 144 | none | 1-(4-ethylpiperazin-1-yl)carbonyl methyl | (95:5) to (90:10) Cl₂CH₂:methanol | 74 | see example 79 |
| 145 | none | 1-(4-piperidino-piperidin-1-yl) carbonyl-methyl | (6:4) toluene:methanol | 81 | see example 79 |
| 146 | none | 1-[N,N-bis (2-N',N'-diethyl-aminoethyl) carbamoyl-methyl] | methanol | 19 | see example 79 |

* These compounds were obtained from the corresponding (7-azaindol-3-yl)methylene benzothiazinones already described, by methods well known for those skilled in the art.

TABLE 6

Physical data for compounds synthesized having structural formula XIII.

| | | Elemental analysis | | | | | |
|---|---|---|---|---|---|---|---|
| | | Carbon | | Hydrogen | | Nitrogen | |
| Example | Mp. (° C.) | calculated | found | calculated | found | calculated | found |
| 123 | 223–4 | 65.73 | 65.54 | 5.24 | 5.03 | 11.50 | 11.34 |
| 124 | >340 | 56.80 | 56.67 | 2.98 | 3.13 | 16.56 | 16.45 |
| 125 | >340 | 62.12 | 61.68 | 3.58 | 3.67 | 13.58 | 13.23 |
| 126 (0.15 H₂O)[1] | >340 | 64.86 | 64.91 | 4.14 | 3.85 | 14.02 | 14.19 |
| 126 (salt) | 341–4 | 52.43 | 52.20 | 3.88 | 3.67 | 10.79 | 10.67 |
| 127 | 218–20 | NA | NA | NA | NA | NA | NA |
| 127 (salt) (1.0 H₂O)[1] | 196–7 | 49.89 | 50.29 | 4.81 | 4.56 | 8.72 | 8.96 |

TABLE 6-continued

Physical data for compounds synthesized having structural formula XIII.

| | | Elemental analysis | | | | | |
|---|---|---|---|---|---|---|---|
| | | Carbon | | Hydrogen | | Nitrogen | |
| Example | Mp. (° C.) | cal-culated | found | cal-culated | found | cal-culated | found |
| 128 | 186–7 | NA | NA | NA | NA | NA | NA |
| 128 (salt) (1.0 $H_2O$)[1] | 255–7 | 46.92 | 46.59 | 5.48 | 5.41 | 9.52 | 9.40 |
| 129 | 243–5 | NA | NA | NA | NA | NA | NA |
| 129 (salt) (0.5 $H_2O$)[1] | 270–2 | 53.99 | 53.60 | 5.32 | 5.74 | 10.95 | 10.61 |
| 130 | 295–7 | NA | NA | NA | NA | NA | NA |
| 130 (salt) (1.0 $H_2O$)[1] | 178–9 | 45.68 | 45.95 | 5.33 | 5.04 | 9.26 | 9.22 |
| 131 | 158–60 | 64.85 | 64.84 | 5.19 | 5.23 | 10.31 | 10.29 |
| 132 (0.5 $H_2O$)[1] | 247–9 | 62.41 | 62.27 | 4.66 | 4.88 | 12.13 | 11.87 |
| 133 | 256–8 | 66.43 | 66.23 | 4.26 | 4.42 | 13.67 | 13.48 |
| 134 | 239–41 | 64.07 | 64.12 | 4.48 | 4.89 | 12.45 | 12.01 |
| 135 | 229–30 | 65.91 | 65.47 | 5.53 | 5.52 | 15.37 | 15.23 |
| 136 | 253–5 | 63.31 | 63.32 | 4.52 | 4.56 | 11.07 | 11.13 |
| 137 | 262–5 | 62.19 | 61.69 | 5.44 | 5.45 | 15.11 | 15.00 |
| 138 | 296–7 | 59.99 | 60.41 | 3.92 | 4.00 | 11.66 | 11.65 |
| 139 (0.5 $H_2O$)[1] | 230–1 | 63.18 | 62.96 | 6.20 | 6.31 | 17.00 | 16.72 |
| 140 (0.2 $H_2O$)[1] | 251–3 | 63.07 | 62.91 | 5.41 | 5.39 | 15.99 | 15.53 |
| 141 (0.25 $H_2O$)[1] | 152–7 | 64.15 | 64.15 | 6.35 | 6.41 | 14.96 | 14.88 |
| 142 (0.2 $H_2O$)[1] | 228–30 | 64.55 | 64.54 | 5.94 | 6.06 | 15.05 | 15.00 |
| 143 (0.5 $H_2O$)[1] | 222–4 | 63.14 | 63.07 | 5.74 | 5.77 | 15.34 | 15.08 |
| 144 (0.25 toluene)[1] | 224–6 | 65.72 | 65.86 | 5.78 | 6.04 | 14.88 | 14.81 |
| 145 | 237–40 | 67.04 | 66.61 | 6.23 | 6.29 | 13.96 | 13.92 |
| 146 (0.5 $H_2O$)[1] | 144–54 | 64.60 | 64.80 | 7.41 | 7.02 | 15.07 | 14.79 |

[1]The molecular weight calculated for the elemental analysis includes the solvent in the amount indicated.

IV. (Pyrrolo[2,3-c]pyridin-5-yl)methylene Benzothiazinones (XIV).

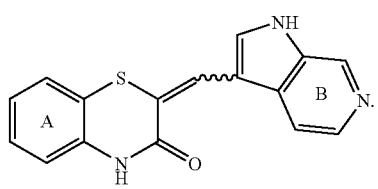

XIV

TABLE 7

Compounds synthesized having structural formula XIV.

| Example | Substituent on Ring A | Substituent on Ring B | Chromatographic Mobile Phase | % Yield | Method |
|---|---|---|---|---|---|
| 147 | none | 7-benzyloxy | (100:1) to (100:20) toluene:ethanol | 29 | see Example 28 |
| 148 | none | 7-hydroxy | NA | 72 | * |

TABLE 7-continued

Compounds synthesized having structural formula XIV.

| Example | Substituent on Ring A | Substituent on Ring B | Chromatographic Mobile Phase | % Yield | Method |
|---|---|---|---|---|---|
| 149 | none | 1-(2-diethyl-aminoethyl)-7-hydroxy | (40:60) to (30:70) $Cl_2CH_2$:methanol | 45 | * |

* These compounds were obtained from the corresponding (pyrrolo[2,3-c]pyridin-5-yl)methylenebenzothiazinones already described, by methods well known to those skilled in the art.

TABLE 8

Physical data for compounds synthesized having structural formula XIV.

| | | Elemental analysis | | | | | |
|---|---|---|---|---|---|---|---|
| | | Carbon | | Hydrogen | | Nitrogen | |
| Example | Mp. (° C.) | cal-culated | found | cal-culated | found | cal-culated | found |
| 147 (0.25 $H_2O$)[1] | 301–2 | 68.38 | 68.67 | 4.36 | 4.33 | 10.40 | 10.53 |
| 148 (0.75 $H_2O$)[1] | >350 | 59.52 | 59.58 | 3.90 | 4.32 | 13.01 | 13.14 |
| 149 (0.75 $H_2O$)[1] | >350 | 62.61 | 62.58 | 6.09 | 5.79 | 13.27 | 13.19 |

[1]The molecular weight calculated for the elemental analysis includes the solvent in the amount indicated.

V. (Imidazol-2-yl)methylene Benzothiazinones (XV).

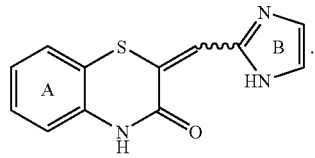

XV

TABLE 9

Compounds synthesized having structural formula XV.

| Example | Substituent on Ring A | Substituent on Ring B | Chromatographic Mobile Phase | % Yield | Method |
|---|---|---|---|---|---|
| 150 | None | none | (9:1) dichloro-methane:ethanol | 15 | see Example 28 |
| 151 (E)-isomer | none | 4-trifluoro-methyl | (95:5) to (97:3) dichloro-methane:ethyl acetate to di-chloromethane:ethanol | 20 | see Example 17 |
| 151 (Z)-isomer | none | 4-trifluoro-methyl | (95:5) to (97:3) dichloromethane:ethyl acetate to dichloromethane:ethanol | 65 | see Example 17 |

TABLE 9-continued

Compounds synthesized having structural formula XV.

| Example | Substituent on Ring A | Substituent on Ring B | Chromatographic Mobile Phase | % Yield | Method |
|---|---|---|---|---|---|
| 152 (Z)-isomer | none | 4-cyano | | 83 | * |

* This compound was obtained from the corresponding (imidazol-2-yl)methylenebenzoxazinone already described, by methods well known to those skilled in the art.

TABLE 10

Physical data for compounds synthesized having structural formula XV.

| | | Elemental analysis | | | | | |
|---|---|---|---|---|---|---|---|
| | | Carbon | | Hydrogen | | Nitrogen | |
| Example | Mp. (° C.) | calculated | found | calculated | found | calculated | found |
| 150 | 321–3 | 59.24 | 59.18 | 3.73 | 3.82 | 17.27 | 16.79 |
| 151 (E)-isomer | 270–2 | 50.16 | 50.43 | 2.59 | 2.54 | 13.50 | 13.49 |
| 151 (E)-isomer (0.8 EtOH)[1] | 271–4 | 50.37 | 50.59 | 3.70 | 3.64 | 12.07 | 12.04 |
| 152 (Z)-isomer (0.9 EtOH)[1] | >350 | 57.39 | 57.10 | 4.36 | 4.53 | 18.08 | 17.72 |

[1] The molecular weight calculated for the elemental analysis includes the solvent in the amount indicated.

VI. (1-Methyl-1H-benzo[d]imidazol-2-yl)methylene Benzothiazinones (XVI).

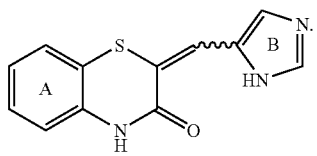

XVI

TABLE 11

Compounds synthesized having structural formula XVI.

| Example | Substituent on Ring A | Substituent on 3-azaindole ring | Chromatographic Mobile Phase | % Yield | Method |
|---|---|---|---|---|---|
| 153 | none | 1-CH$_3$ | (100:1) to (100:20) Toluene:Ethanol | 89 | See Example 28 |

TABLE 12

Physical data for compounds synthesized having structural formula XVI.

| | | Elemental analysis | | | | | |
|---|---|---|---|---|---|---|---|
| | | Carbon | | Hydrogen | | Nitrogen | |
| Example | Mp. (° C.) | calculated | found | calculated | found | calculated | found |
| 153 | 332–3 | 66.43 | 66.40 | 4.26 | 4.23 | 13.67 | 13.65 |

VII. (Imidazol-5-yl)methylene Benzothiazinones (XVII).

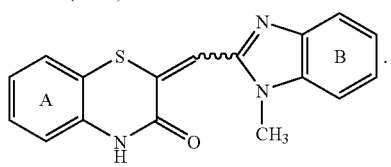

XVII

Compounds synthesized having structural formula XVII.

| Example | Substituent on Ring A | Substituent on Ring B | Chromatographic Mobile Phase | % Yield | Method |
|---|---|---|---|---|---|
| 154 | none | 4-CH$_3$ | (98:2) to (95:5) dichloromethane:ethanol | 31 | see Example 28 |
| 155 | none | none | (8:2) dichloromethane:methanol | 41 | see Example 28 |
| 156 | 7-NO$_2$ | 4-CH$_3$ | NA | 53 | see Example 28 |
| 157 | 7-NH$_2$ | 4-CH$_3$ | (95:5) dichloromethane:methanol | 16 | see Example 41 |
| 158 | none | 2-CH$_3$ | (95:5) ethyl acetate:ethanol | 26 | see Example 28 |
| 159 | none | 2-ethyl-4-methyl | (85:15) to (90:10) ethyl acetate:hexane | 44 | see Example 28 |
| 160 | none | 3-(2-diethylaminoethyl)-4-CH$_3$ | NA | 38 | see Example 60 |
| 161 | none | 1-(2-diethylaminoethyl)-4-CH$_3$ | NA | 21 | see Example 60 |
| 162 | none | 1-(2-morpholinoethyl)-4-CH$_3$ | NA | 6 | see Example 60 |
| 163 | none | 3-(2-morpholinoethyl)-4-CH$_3$ | NA | 30 | see Example 60 |
| 164 (Z)-isomer | none | 1-methyl-2-methylthio | NA | 85 | see Example 17 |
| 165 | none | 4-methoxycarbonyl | NA | 78 as a mixture of isomers | see Example 17 |
| 166 (Z)-isomer | none | 4-hydroxymethyl | NA | 29 | see Example 17 |

TABLE 14

Physical data for compounds synthesized having structural formula XVII.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 154 | 255–7 | 60.68 | 60.15 | 4.31 | 4.41 | 16.33 | 16.10 |
| 155 | 314–5 | 59.24 | 59.17 | 3.73 | 4.01 | 17.27 | 17.35 |
| 156 (0.5 H$_2$O)[1] | 325–7 | 50.16 | 50.20 | 3.56 | 3.82 | 18.00 | 18.05 |
| 157 | 281–4 | 57.34 | 57.04 | 4.44 | 4.65 | 20.57 | 20.15 |
| 158 | 282–4 | 60.68 | 60.53 | 4.31 | 4.15 | 16.33 | 16.09 |
| 159 | 280–2 | 63.13 | 63.11 | 5.30 | 5.46 | 14.72 | 14.54 |
| 160 | 198–9 | 64.01 | 64.01 | 6.78 | 6.81 | 15.72 | 15.65 |
| 161 | 150–2 | 64.01 | 63.83 | 6.78 | 6.77 | 15.72 | 15.53 |
| 162 | 245–7 | 61.60 | 61.59 | 5.98 | 6.04 | 15.12 | 14.97 |
| 163 (0.2 H$_2$O)[1] | 200–2 | 61.00 | 60.85 | 6.03 | 5.95 | 14.97 | 14.79 |
| 164 (Z)-isomer | 261–3 | 55.42 | 55.61 | 4.32 | 4.40 | 13.85 | 13.81 |
| 165 mixture of Z/E isomers | 262–6 | 55.81 | 55.83 | 3.68 | 3.84 | 13.95 | 13.90 |
| 166 (Z)-isomer | 252–4 | 57.13 | 57.24 | 4.06 | 4.19 | 15.37 | 15.24 |

[1]The molecular weight calculated for the elemental analysis includes the solvent in the amount indicated.

VIII. (Furan-3-yl)methylene Benzothiazinones (XVIII).

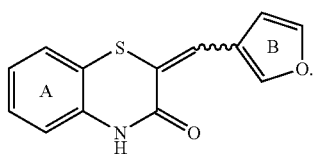

TABLE 15

Compounds synthesized having structural formula XVIII.

| Example | Substituent on Ring A | Substituent on Ring B | Chromatographic Mobile Phase | % Yield | Method |
|---|---|---|---|---|---|
| 167 | none | none | (100:1) to (100:20) toluene:ethanol | 81 | see Example 28 |

TABLE 16

Physical data for compounds synthesized having structural formula XVIII.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 167 | 193–5 | 64.18 | 64.06 | 3.73 | 3.95 | 5.76 | 5.74 |

IX. (Thien-3-yl)methylene Benzothiazinones (XIX).

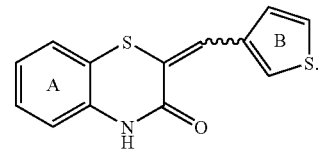

TABLE 17

Compounds synthesized having structural formula XIX.

| Example | Substituent on Ring A | Substituent on Ring B | Chromatographic Mobile Phase | % Yield | Method |
|---|---|---|---|---|---|
| 168 | none | none | (100:1) to (100:20) toluene:ethanol | 93 | see Example 28 |

TABLE 18

Physical data for compounds synthesized having structural formula XIX.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 168 | 229–31 | 60.21 | 60.07 | 3.49 | 3.72 | 5.40 | 5.40 |

X. (Pyrazol-4-yl)methylene Benzothiazinones (XX).

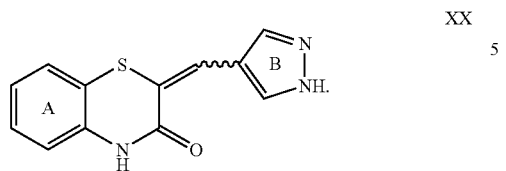

TABLE 19

Compounds synthesized having structural formula XX.

| Example | Substituent on Ring A | Substituent on Ring B | Chromatographic Mobile Phase | % Yield | Method |
|---|---|---|---|---|---|
| 169 | none | 3-CH₃ | (100:1) to (100:20) toluene:ethanol | 69 | see Example 28 |
| 170 | none | 3-Phenyl | NA | 89 | see Example 28 |
| 171 | none | 1-(2-diethyl aminoethyl)-3-methyl | NA | 24 | see Example 60 |
| 172 | none | 1-(2-diethyl aminoethyl)-5-methyl | NA | 19 | see Example 60 |
| 173 | none | 1-(2-morpholinoethyl)-3-methyl | (90:10) ethyl acetate:ethanol | 24 | see Example 60 |
| 174 | none | 1-(morpholinethyl)-5-methyl | (90:10) ethyl acetate:ethanol | 33 | see Example 60 |
| 175 | none | 1-CH₃ | NA | 86 | see Example 17 |
| 176 | none | 1-C(CH₃)₃ | NA | 83 | see Example 17 |
| 177 | none | 1-ethoxy carbonyl methyl-3-methyl | (100:0) to (95:5) CH₂Cl₂:CH₃OH | 66 as a mixture of isomers | see Example 17 |
| 178 | none | 1-ethoxy carbonyl methyl-5-methyl | (100:0) to (95:5) CH₂Cl₂:CH₃OH | 66 as a mixture of isomers | see Example 17 |
| 179 | none | 1-carboxy methyl-3-methyl | NA | 100 | * |
| 180 | none | 1-carboxy methyl-5-methyl | NA | 97 | * |
| 181 | none | 1-[N-(2-dimethyl aminoethyl) carbamoyl methyl]-3-methyl | NA | 65 | see Example 24 |
| 182 | none | 1-[N-(3-(4-methyl piperazin-1-yl)propyl) carbamoyl methyl]-3-methyl | NA | 85 | see Example 24 |
| 183 | none | 1-[N-(2-dimethyl aminoethyl) carbamoyl methyl]-5-methyl | NA | 59 | see Example 24 |
| 184 | none | 1-[N-(2-morpholinoethyl) carbamoyl methyl]-3-methyl | NA | 79 | see Example 24 |

TABLE 19-continued

Compounds synthesized having structural formula XX.

| Example | Substituent on Ring A | Substituent on Ring B | Chromatographic Mobile Phase | % Yield | Method |
|---|---|---|---|---|---|
| 185 | none | 1-[(4-piperidino piperidin-1-yl)carbonyl methyl]-3-methyl | NA | 86 | see Example 79 |
| 186 | none | 1-[N-(2-N',N'-diethyl aminoethyl)-N-methyl] carbamoyl methyl-3-methyl | (4:6) $CH_2Cl_2$:MeOH | 78 | see Example 79 |
| 187 | none | 1-(4-methyl piperazin-1-yl)carbonyl methyl-5-methyl | NA | 28 | see Example 79 |
| 188 | none | 1-(4-methyl piperazin-1-yl)carbonyl methyl-3-methyl | NA | 45 | see Example 79 |
| 189 | none | 1-[N-(3-(imidazol-1-yl)propyl) carbamoyl methyl]-3-methyl | NA | 90 | see Example 79 |
| 190 | none | 1-[4-(2-hydroxyethyl) piperazin-1-yl]carbonyl methyl-5-methyl | NA | 95 | see Example 79 |
| 191 | none | 1-{4-[2-(2-hydroxy ethoxy)ethyl] piperazin-1-yl}carbonyl methyl-5-methyl | (9:1) $CH_2Cl_2$:MeOH | 59 | see Example 79 |

\* These compounds were obtained from the corresponding (pyrazol-4-yl) methylene benzothiazinones already described, by methods well known to those skilled in the art.

TABLE 20

Physical data for compounds synthesized having structural formula XX.

| Example | Mp. (° C.) | Carbon calculated | Carbon found | Hydrogen calculated | Hydrogen found | Nitrogen calculated | Nitrogen found |
|---|---|---|---|---|---|---|---|
| 169 | 297–9 | 60.68 | 60.71 | 4.31 | 4.28 | 16.33 | 16.41 |
| 170 | 290–2 | 67.69 | 67.44 | 4.10 | 4.08 | 13.16 | 13.06 |
| 171 (0.25 $H_2O$)[1] | 160–2 | 63.21 | 63.09 | 6.84 | 6.95 | 15.52 | 15.27 |
| 172 (0.25 $H_2O$)[1] | 197–200 | 63.21 | 63.56 | 6.84 | 6.85 | 15.52 | 15.58 |
| 173 (0.25 $H_2O$)[1] | 190–1 | 60.86 | 61.12 | 6.05 | 6.04 | 14.94 | 14.99 |
| 174 | 195–6 | 61.59 | 61.24 | 5.98 | 6.03 | 15.12 | 14.96 |
| 175 | 255–6 | 60.68 | 60.83 | 4.31 | 4.53 | 16.33 | 16.29 |
| 176 | 228–30 | 64.19 | 64.30 | 5.72 | 5.32 | 14.03 | 14.07 |
| 177 | 226–7 | 59.46 | 59.63 | 4.99 | 4.94 | 12.24 | 12.20 |
| 178 | 231 | 59.46 | 59.47 | 4.99 | 4.94 | 12.24 | 12.16 |
| 179 (0.5 EtOH)[1] | 278–82 | 56.79 | 56.62 | 4.77 | 5.06 | 12.42 | 11.85 |
| 180 | 288–92 | 57.13 | 57.49 | 4.16 | 4.34 | 13.32 | 13.26 |

TABLE 20-continued

Physical data for compounds synthesized having structural formula XX.

| | | Elemental analysis | | | | | |
|---|---|---|---|---|---|---|---|
| | | Carbon | | Hydrogen | | Nitrogen | |
| | Mp. | | | | | | |
| Example | (° C.) | calculated | found | calculated | found | calculated | found |
| 181 | 253–5 | 59.20 | 58.86 | 6.01 | 5.86 | 18.17 | 17.85 |
| 182 (0.2 H$_2$O)[1] | 250–2 | 60.29 | 60.11 | 6.69 | 6.53 | 18.34 | 18.20 |
| 183 (0.2 H$_2$O)1 | 220–2 | 58.65 | 58.56 | 6.06 | 5.97 | 18.00 | 17.86 |
| 184 | 244–5 | 59.00 | 58.84 | 5.89 | 5.95 | 16.38 | 16.45 |
| 185 (0.25 H$_2$O)[1] | 244–8 | 63.87 | 63.74 | 6.75 | 6.67 | 14.90 | 14.74 |
| 186 | 160–70 | 61.80 | 61.60 | 6.84 | 6.82 | 16.38 | 16.17 |
| 187 (0.2 H$_2$O)[1] | 285–7 | 59.89 | 59.89 | 5.88 | 5.97 | 17.46 | 17.13 |
| 188 | 263–5 | 60.43 | 60.45 | 5.83 | 6.02 | 17.62 | 17.54 |
| 189 | 228–30 | 59.70 | 59.68 | 5.25 | 5.35 | 19.89 | 20.01 |
| 190 (0.25 EtOH)[1] | 267–70 | 58.82 | 58.65 | 6.08 | 5.88 | 15.95 | 15.78 |
| 191 (1.25 H$_2$O)[1] | 193–5 | 55.91 | 55.81 | 6.43 | 6.14 | 14.17 | 14.06 |

[1]The molecular weight calculated for the elemental analysis includes the solvent in the amount indicated.

XI. (Indol-2-yl)methylene Benzothiazinones (XXI).

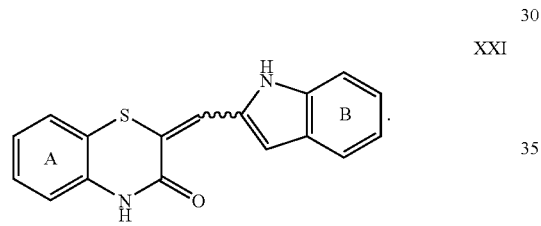

TABLE 21

Compounds synthesized having structural formula XXI.

| Example | Substituent on Ring A | Substituent on Ring B | Chromatographic Mobile Phase | % Yield | Method |
|---|---|---|---|---|---|
| 192 (E-isomer) | none | none | (95:5) to (80:20) toluene-ethyl acetate | <10 | see Example 28 |
| 192 (Z-isomer) | none | none | (95:5) to (80:20) toluene:ethyl acetate | <10 | see Example 28 |

TABLE 22

Physical data for compounds synthesized having structural formula XXI.

| | | Elemental analysis | | | | | |
|---|---|---|---|---|---|---|---|
| | | Carbon | | Hydrogen | | Nitrogen | |
| | Mp. | | | | | | |
| Example | (° C.) | calculated | found | calculated | found | calculated | found |
| 192 (E-isomer) | 270–2 | 69.84 | 69.81 | 4.14 | 4.32 | 9.58 | 9.24 |
| 192 (Z-isomer) (0.1 H$_2$O)[1] | 303–5 | 69.41 | 69.26 | 4.18 | 4.22 | 9.52 | 9.19 |

[1]The molecular weight calculated for the elemental analysis includes the solvent in the amount indicated.

XII. (Pyrrol-3-yl)methylene Benzothiazinones (XXII).

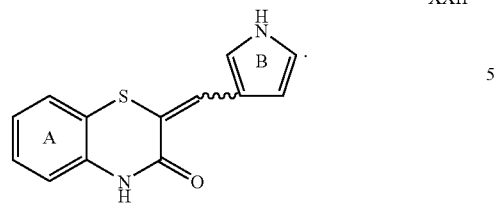

XXII

TABLE 23

Compounds synthesized having structural formula XXII.

| Example | Substituent on Ring A | Substituent on Ring B | Chromatographic Mobile Phase | % Yield | Method |
|---|---|---|---|---|---|
| 193 | none | none | (98:2) to (95:5) toluene:ethanol | 65 | see Example 28 |

TABLE 24

Physical data for compounds synthesized having structural formula XXII.

| | | Elemental analysis | | | | | |
|---|---|---|---|---|---|---|---|
| | Mp. | Carbon | | Hydrogen | | Nitrogen | |
| Example | (° C.) | calculated | found | calculated | found | calculated | found |
| 193 | 260–2 | 64.44 | 64.19 | 4.16 | 4.26 | 11.56 | 11.21 |

XIII. (Indazol-3-yl)methylene Benzothiazinones (XXIII).

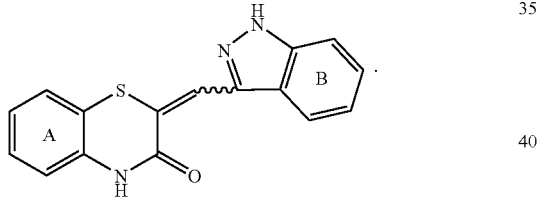

XXIII

TABLE 25

Compounds synthesized having structural formula XXIII.

| Example | Substituent on Ring A | Substituent on Ring B | Chromatographic Mobile Phase | % Yield | Method |
|---|---|---|---|---|---|
| 194 | none | none | NA | 65 | see Example 28 |

TABLE 26

Physical data for compounds synthesized having structural formula XXIII.

| | | Elemental analysis | | | | | |
|---|---|---|---|---|---|---|---|
| | Mp. | Carbon | | Hydrogen | | Nitrogen | |
| Example | (° C.) | calculated | found | calculated | found | calculated | found |
| 194 | 343–5 | 65.51 | 65.21 | 3.78 | 4.15 | 14.32 | 14.42 |

XIV. (Thiazol-2-yl)methylene Benzothiazinones (XXIV).

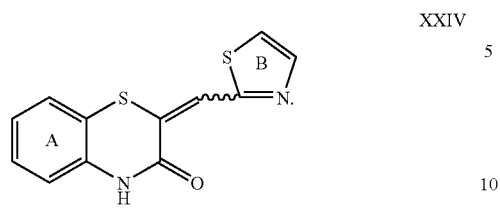

XXIV

TABLE 27

Compounds synthesized having structural formula XXIV.

| Example | Substituent on Ring A | Substituent on Ring B | Chromatographic Mobile Phase | % Yield | Method |
|---|---|---|---|---|---|
| 195 | None | none | (100:1) CH$_2$Cl$_2$:ethanol | 13 | see Example 28 |

TABLE 28

Physical data for compounds synthesized having structural formula XXIV.

| | | Elemental analysis | | | | | |
|---|---|---|---|---|---|---|---|
| | Mp. | Carbon | | Hydrogen | | Nitrogen | |
| Example | (° C.) | calculated | found | calculated | found | calculated | found |
| 195 | 272–4 | 55.36 | 55.31 | 3.10 | 3.22 | 10.76 | 10.69 |

XV. (Pyrazol-3-yl)methylene Benzothiazinones (XXV).

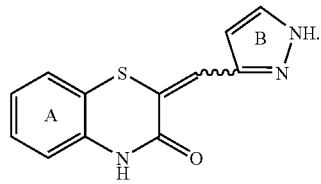

XXV

Example 196

Synthesis of 2-[(1H-pyrazol-3-yl)methylene]-2H-1, 4-benzothiazin-3(4H)-one

A solution of sodium methoxide (30 mg, 0.55 mmol) in anhydrous methanol (3 ml) was added to a stirred mixture of 2-diethylphosphonyl-2H-1,4-benzothiazin-3(4H)-one (150 mg, 0.5 mmol) and 1H-pyrazole-3-carboxaldehyde (50 mg, 0.5 mmol) in anhydrous methanol (20 ml). Stirring was continued for 19 hours at room temperature, then the precipitated solid was filtered off and washed with methanol.

TABLE 29

Compounds synthesized having structural formula XXV.

| Example | Substituent on Ring A | Substituent on Ring B | Chromatographic Mobile Phase | % Yield | Method |
|---|---|---|---|---|---|
| 196 | None | none | NA | 67 | see Example 196 |
| 197 | None | 5-ethoxy carbonyl | NA | 86 | see Example 196 |
| 198 | None | 5-[N-(2-morpholino ethyl) carbamoyl] | NA | 76 | see Example 24 |
| 199 | None | 5-[N-(2-methoxyethyl) carbamoyl] | NA | 82 | see Example 24 |
| 200 | None | 5-[N-(2-(pyrrolidin-1-yl) ethyl) carbamoyl] | NA | 47 | see Example 24 |

TABLE 29-continued

Compounds synthesized having structural formula XXV.

| Example | Substituent on Ring A | Substituent on Ring B | Chromatographic Mobile Phase | % Yield | Method |
|---|---|---|---|---|---|
| 201 | None | 5-[N-(3-dimethylaminopropyl)carbamoyl] | NA | 69 | see Example 24 |

TABLE 30

Physical data for compounds synthesized having structural formula XXV.

| | | Elemental analysis | | | | | |
|---|---|---|---|---|---|---|---|
| | Mp. | Carbon | | Hydrogen | | Nitrogen | |
| Example | (° C.) | calculated | found | calculated | found | calculated | found |
| 196 | 284–7 | 59.24 | 58.69 | 3.73 | 3.80 | 17.27 | 17.03 |
| 197 (0.7 H$_2$O)[1] | 260–2 | 54.94 | 54.96 | 4.43 | 4.55 | 12.81 | 12.73 |
| 198 | 284–6 | 57.13 | 57.44 | 5.30 | 5.37 | 17.53 | 17.42 |
| 199 | 276–80 | 55.80 | 56.26 | 4.68 | 4.82 | 16.27 | 16.28 |
| 200 | 273–5 | 59.51 | 59.40 | 5.52 | 5.64 | 18.26 | 18.20 |
| 201 (0.5 H$_2$O)[1] | 265 | 56.82 | 56.93 | 5.83 | 5.98 | 18.41 | 18.03 |

[1]The molecular weight calculated for the elemental analysis includes the solvent in the amount indicated.

XVI. (Thiazol-5-yl)methylene Benzothiazinones (XXVI).

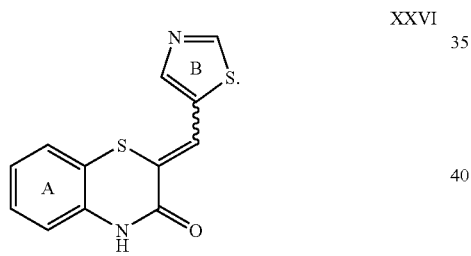

XXVI

TABLE 31

Compounds synthesized having structural formula XXVI.

| Example | Substituent on Ring A | Substituent on Ring B | Chromatographic Mobile Phase | % Yield | Method |
|---|---|---|---|---|---|
| 202 | none | 2-dimethylamino | NA | 83 | see Example 196 |

TABLE 32

Physical data for compounds synthesized having structural formula XXVI.

| | | Elemental analysis | | | | | |
|---|---|---|---|---|---|---|---|
| | Mp. | Carbon | | Hydrogen | | Nitrogen | |
| Example | (° C.) | calculated | found | calculated | found | calculated | found |
| 202 (0.5 EtOH)[1] | 258–60 | 55.19 | 55.33 | 4.94 | 4.88 | 12.87 | 12.92 |

[1]The molecular weight calculated for the elemental analysis includes the solvent in the amount indicated.

XVII. (Indol-4-yl)methylene Benzothiazinones (XXVII).

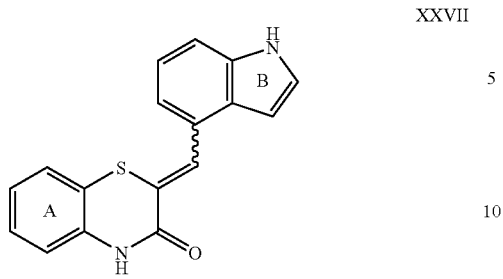

TABLE 33

Compounds synthesized having structural formula XXVII.

| Example | Substituent on Ring A | Substituent on Ring B | Chromatographic Mobile Phase | % Yield | Method |
|---|---|---|---|---|---|
| 203 | none | none | NA | 48 as a mixture of Z/E isomers | see Example 17 |
| 204 | none | 3-morpholino-methyl | (100:1) to (100:4) CH$_2$Cl$_2$:EtOH | 43 as a mixture of Z/E isomers | see Example 17 |

TABLE 34

Physical data for compounds synthesized having structural formula XXVII.

| | | Elemental analysis | | | | | |
|---|---|---|---|---|---|---|---|
| | Mp. | Carbon | | Hydrogen | | Nitrogen | |
| Example | (° C.) | calculated | found | calculated | found | calculated | found |
| 203 | 218–20 | 69.84 | 69.48 | 4.14 | 4.26 | 9.48 | 9.58 |
| 204 (0.25 H$_2$O)[1] | 137–40 | 66.73 | 66.66 | 5.47 | 5.58 | 10.61 | 10.56 |

[1]The molecular weight calculated for the elemental analysis includes the solvent in the amount indicated.

XVIII. (Indol-7-yl)methylene Benzothiazinones (XXVIII).

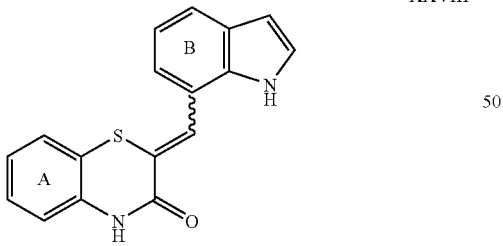

TABLE 35

Compounds synthesized having structural formula XXVIII.

| Example | Substituent on Ring A | Substituent on Ring B | Chromatographic Mobile Phase | % Yield | Method |
|---|---|---|---|---|---|
| 205 | none | none | NA | 64 | see Example 17 |
| 206 | none | 3-(dimethyl amino)methyl | NA | 79 | see Example 17 |

TABLE 35-continued

Compounds synthesized having structural formula XXVIII.

| Example | Substituent on Ring A | Substituent on Ring B | Chromatographic Mobile Phase | % Yield | Method |
|---|---|---|---|---|---|
| 207 | none | 3-morpholinomethyl | NA | 90 | see Example 17 |
| 208 | none | 3-piperidinomethyl | NA | 85 | see Example 17 |
| 209 | none | 3-(4-methylpiperazin-1-yl)methyl | NA | 74 | see Example 17 |

TABLE 36

Physical data for compounds synthesized having structural formula XXVIII.

| | | Elemental analysis | | | | | |
|---|---|---|---|---|---|---|---|
| | Mp. | Carbon | | Hydrogen | | Nitrogen | |
| Example | (° C.) | calculated | found | calculated | found | calculated | found |
| 205 | 235–7 | 69.84 | 69.73 | 4.14 | 4.27 | 9.58 | 9.48 |
| 206 (0.1 toluene)[1] | 185–92 | 69.32 | 69.44 | 5.56 | 5.66 | 11.72 | 11.82 |
| 207 | 219–24 | 67.50 | 67.50 | 5.41 | 5.57 | 10.73 | 10.72 |
| 208 (0.5 CH$_3$OH)[1] | 110–15 | 69.60 | 69.28 | 6.21 | 6.19 | 10.36 | 10.22 |
| 209 (0.1 AcOEt)[1] | 220–4 | 68.00 | 68.07 | 6.05 | 6.25 | 13.55 | 13.30 |

[1]The molecular weight calculated for the elemental analysis includes the solvent in the amount indicated.

XIX. (Pyrrol-2-yl)methylene Benzoxazinones (XXIX).

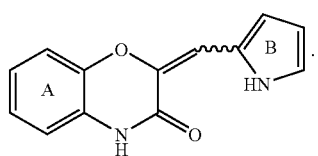

XXIX

Example 210

Synthesis of 2-[(Pyrrol-2-yl)methylene]-2H-1,4-benzoxazin-3(4H)-one

Sodium methoxide (0.65 g, 0.012 mol) was added in one portion to a mixture of 2H-1,4-benzoxazin-3(4H)-one (1.49 g, 0,01 mol) and pyrrole-2-carboxaldehyde (1.58 g, 0.016 mol) in dry DMF (10 ml). The reaction mixture was refluxed for 48 h, then cooled at room temperature and poured into crushed ice and left overnight at 4° C. The precipitated solid was collected by filtration, washed with water and dried. The precipitate was boiled with ethanol (150 ml) and filtered while hot to remove impurities. The filtrate was evaporated to dryness under reduced pressure, and the residue was chromatographed on a silica gel column using (95:5) toluene:ethyl acetate as the mobile phase.

Example 221

Synthesis of (Z) and (E)-2-[(1-Methylpyrrol-2-yl)methylene]-2H-1,4-benzoxazin-3(4H)-one Sodium methoxide (0.15 g, 0.0027 mol) was added in one portion to a mixture of 2-diethylphosphonyl-2H-1,4-benzoxazin-3(4H)-one (0.57 g, 0.002 mol) and 1-methylpyrrole-2-carboxaldehyde (0.22 g, 0.002 mol) in methanol (20 ml). The reaction mixture was stirred at room temperature for 48 h. The precipitated solid was collected by filtration and washed with cold methanol to give the corresponding (E)-isomer. The filtrate was evaporated to dryness, and the residue was chromatographed on a silica gel column using (97:3) dichloromethane:ethanol as the mobile phase to give the corresponding (Z)-isomer.

Table 37 lists the compounds that were synthesized having structural formula XXIX. Examples 210–220 in table 37 were synthesized as described in Example 210 using an appropriately substituted 2H-1,4-benzoxazin-3(4H)-one and an appropriately pyrrole-2-carboxaldehyde. Examples 221–222 in table 37 were synthesized as described in example 221 using an appropriately substituted 2H-1,4-benzoxazin-3(4H) and an appropriately pyrrole-2-carboxaldehyde.

TABLE 37

Compounds synthesized having structural formula XXIX.

| Example | Substituent on Ring A | Substituent on Ring B | Chromatographic Mobile Phase | % Yield (E)-isomer | % Yield (Z)-isomer | Method |
|---|---|---|---|---|---|---|
| 210 | none | none | (95:5) toluene:ethyl acetate | 3 | 20 | see Example 210 |
| 211 | 6-Cl | none | (95:5) toluene:ethyl acetate | 2 | 22 | see Example 210 |
| 212 | 6-$CH_3$ | none | (95:5) toluene:ethyl acetate | 2 | 17 | see Example 210 |
| 213 | 7-$CH_3$ | none | (95:5) toluene:ethyl acetate | 2 | 19 | see Example 210 |
| 214 | 6-$OCH_3$ | none | (95:5) toluene:ethyl acetate | 1 | 13 | see Example 210 |
| 215 | 7-Cl | none | (95:5) toluene:ethyl acetate | 2 | 23 | see Example 210 |
| 216 | 7-$OCH_3$ | none | (95:5) toluene:ethyl acetate | 1 | 19 | see Example 210 |
| 217 | 6-CN | none | (95:5) toluene:ethyl acetate | 0 | 15 | see Example 210 |
| 218 | 5-$CH_3$ | none | (95:5) toluene:ethyl acetate | 1 | 19 | see Example 210 |
| 219 | 6,7-Cl | none | (95:5) toluene:ethyl acetate | 1 | 20 | see Example 210 |
| 220 | none | 5-$CH_3$ | (90:10) toluene:ethylacetate | 0 | 9 | see Example 210 |
| 221 | none | 1-methyl | (97:3) dichloromethane:ethanol | 57 | 23 | see Example 221 |
| 222 | none | 3,5-dimethyl | toluene to (90:10) toluene:ethanol | 39 | 34 | see Example 221 |
| 223 salt | none | 3,5-dimethyl-4-amino methyl | NA | 43 | — | * |
| 224 | none | 3,5-dimethyl-4-amino methyl | NA | — | 74 | * |

*These compounds were obtained from the corresponding (pirrol-2-yl) methylene benzoxazinones already described by methods well known to those skilled in the art. Example 223 is hydroiodide.

TABLE 38

Physical data for compounds synthesized having structural formula XXIX.

| | | Elemental analysis | | | | |
|---|---|---|---|---|---|---|
| | Mp. | Carbon | | Hydrogen | | Nitrogen | |
| Example | (° C.) | calculated | found | calculated | found | calculated | found |
| 210 (E)-isomer | 233–5 | 69.02 | 69.04 | 4.46 | 4.45 | 12.38 | 12.18 |
| 210 (Z)-isomer | 263–5 | 69.02 | 68.91 | 4.46 | 4.59 | 12.38 | 12.21 |
| 211 (E)-isomer | 259–61 | 59.90 | 59.40 | 3.48 | 3.52 | 10.75 | 10.53 |
| 211 (Z)-isomer | 284–6 | 59.90 | 59.89 | 3.48 | 3.59 | 10.75 | 10.54 |
| 212 (E)-isomer | 243–6 | 69.99 | 69.70 | 5.03 | 5.28 | 11.66 | 11.62 |
| 212 (Z)-isomer | 299–300 | 69.99 | 69.86 | 5.03 | 5.09 | 11.66 | 11.52 |
| 213 (E)-isomer | 205–8 | 69.99 | 69.76 | 5.03 | 5.01 | 11.66 | 11.56 |

TABLE 38-continued

Physical data for compounds synthesized having structural formula XXIX.

| Example | Mp. (° C.) | Carbon calculated | Carbon found | Hydrogen calculated | Hydrogen found | Nitrogen calculated | Nitrogen found |
|---|---|---|---|---|---|---|---|
| 213 (Z)-isomer (0.25 H$_2$O)[1] | 250–2 | 68.64 | 68.91 | 5.10 | 4.80 | 11.46 | 11.32 |
| 214 (E)-isomer | 230–2 | 65.62 | 65.38 | 4.72 | 4.96 | 10.93 | 10.80 |
| 214 (Z)-isomer | 250–1 | 65.62 | 65.48 | 4.72 | 4.54 | 10.93 | 10.86 |
| 215 (E)-isomer | 240–2 | 59.90 | 60.03 | 3.48 | 3.71 | 10.75 | 10.67 |
| 215 (Z)-isomer | 278–80 | 59.90 | 60.11 | 3.48 | 3.70 | 10.75 | 10.51 |
| 216 (E)-isomer | 214–7 | 65.62 | 65.51 | 4.72 | 4.91 | 10.93 | 10.82 |
| 216 (Z)-isomer | 276–8 | 65.62 | 65.61 | 4.72 | 4.74 | 10.93 | 10.92 |
| 217 (Z)-isomer | 285–7 | 66.93 | 66.61 | 3.61 | 3.90 | 16.72 | 16.53 |
| 218 (E)-isomer | 220–2 | 69.99 | 69.75 | 5.03 | 5.10 | 11.66 | 11.58 |
| 218 (Z)-isomer | 256–8 | 69.99 | 70.13 | 5.03 | 5.24 | 11.66 | 11.88 |
| 219 (E)-isomer | 272–4 | 52.91 | 53.04 | 2.73 | 2.81 | 9.49 | 9.43 |
| 219 (Z)-isomer | 323–5 | 64.72 | 64.48 | 4.59 | 4.66 | 17.41 | 17.20 |
| 220 (Z)-isomer | 248–50 | 69.99 | 69.81 | 5.03 | 5.09 | 11.66 | 11.36 |
| 221 (E)-isomer | 218–20 | 69.76 | 69.99 | 4.94 | 5.03 | 11.57 | 11.66 |
| 221 (Z)-isomer | 263–5 | 59.76 | 69.30 | 4.94 | 5.23 | 11.57 | 11.41 |
| 222 (E)-isomer (0.2 H$_2$O)[1] | 224–6 | 69.86 | 69.56 | 5.63 | 5.65 | 10.86 | 10.69 |
| 222 (Z)-isomer (0.2 C$_2$H$_5$OH)[1] | 248–50 | 70.19 | 70.02 | 5.81 | 5.57 | 10.63 | 10.69 |
| 223 salt (E)-isomer | 223–5 | 49.21 | 49.41 | 5.05 | 5.02 | 9.56 | 9.99 |
| 224 (Z)-isomer (0.3 H$_2$O)[1] | 234–6 | 68.24 | 67.85 | 6.87 | 6.80 | 13.26 | 12.99 |

[1]The molecular weight calculated for the elemental analysis includes the solvent in the amount indicated.

XX. (Indol-3-yl)methylene Benzoxazinones (XXX).

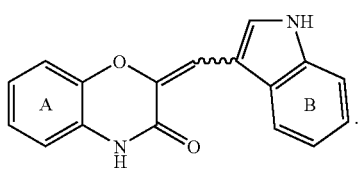

XXX

Example 225

Synthesis of 2-[(Indol-3-yl)methylene]-2H-1,4-benzoxazin-3(4H)-one

Sodium methoxide (0.65 g, 0.012 mol) was added in one portion to a mixture of 2H-1,4-benzoxazin-3(4H)-one (1.49 g, 0.01 mol) and indole-3-carboxaldehyde (2.32 g, 0.016 mol) in dry DMF (10 ml). The reaction mixture was refluxed for 24 h, then cooled at room temperature and poured into crushed ice and left overnight in the refrigerator. The precipitated solid was collected by filtration, washed with water and dried. The crude product was chromatographed on silica gel using (9:1) toluene:ethyl acetate.

Example 231

Synthesis of 2-[(6-Methoxycarbonylindol-3-yl)methylene]-2H-1,4-benzoxazin-3(4H)-one Sodium methoxide (1 g, 0.018 mol) was added in one portion to a mixture of 2-diethylphosphonyl-2H-1,4-benzoxazin-3(4H)-one (3.42 g, 0.012 mol) and 6-methoxycarbonylindol-3-carboxaldehyde (2.55 g, 0.012 mol) in methanol (60 ml). The reaction mixture was refluxed for 21 h, then cooled at room temperature and the precipitated solid was collected by filtration, washed with methanol and dried. Yield 2.78 g (87%) as a mixture of isomers.

Example 232

Synthesis of (Z)-2-[(6-carboxyindol-3-yl)methylene]-2H-1,4-benzoxazin-3(4H)-one

2-[(6-Methoxycarbonylindol-3-yl)methylene]-2H-1,4-benzoxazin-3(4H)-one (2.16 g, 0.008 mol) was heated at reflux in an aqueous sodium hydroxyde solution (6.5 g in 110 ml) for 2 h. The solution was cooled and acidified with concentrate HCl. The precipitated solid was filtered, washed with water and dried to yield 1.8 g, (69%) as (Z)-isomer.

Example 233

Synthesis of (Z)-2-{[6-(N,N-dimethyl-3-aminopropylcarbamoyl)indol-3-yl]methylene}-2H-1,4-benzoxazin-3 (4H)-one Carbonyldiimidazole (0.6 g, 0.0037 mol) was added in one portion under nitrogen atmosphere to a solution of (Z)-2-{[6-carboxyindol-3-yl)methylene]-2H-1,4-benzoxazin-3(4H)-one (0.9 g, 0.0028 mol) in dry N,N-dimethylformamide (45 ml). The reaction mixture was heated at 40° C. for 2 h. The N,N-dimethyl-3-aminopropylamine (0.92 g, 0.009 mol) was added and the mixture was heated at 40° C. for 20 hr. The solvent was evaporated to dryness under reduced pressure and the residue was stirred with dichloromethane. The precipitated solid was collected by filtration, washed with dichloromethane and dried. The crude product was purified by recrystallization from N,N-dimethylformamide:water.

Examples 225–230 Table 39 were synthesized as described in Example 225 using an appropriately substituted 2H-1,4-benzoxazin-3(4H)-one and an appropriately substituted indole-3-carboxaldehyde. Examples 231–233 were synthesized as described above. Example 234 in Table 39 was synthesized as described in Example 221 using an appropriately substituted 2H-1,4-benzoxazin-3(4H)-one and an appropriately substituted indole-3-carboxaldehyde.

TABLE 39

Compounds synthesized having structural formula XXX.

| Example | Substituent on Ring A | Substituent on Ring B | Chromatographic Mobile Phase | % Yield | Method |
|---|---|---|---|---|---|
| 225 | none | none | (9:1) toluene:ethyl acetate | 24 | see Example 225 |
| 226 | none | 1-(4-hydroxybutyl) | (9:1) toluene:ethyl acetate | 21 | see Example 225 |
| 227 | 6-CH₃ | none | (9:1) toluene:ethyl acetate | 19 | see Example 225 |
| 228 | 6-Cl | none | (9:1) toluene:ethyl acetate | 18 | see Example 225 |
| 229 | 7-CH₃ | none | (9:1) toluene:ethyl acetate | 15 | see Example 225 |
| 230 | 5-CH₃ | none | (9:1) toluene:ethyl acetate | 20 | see Example 225 |
| 231 | none | 6-methoxy carbonyl | NA | 87 as mixture of isomers | see Example 231 |
| 232 (Z)-isomer | none | 6-carboxy | NA | 69 | see Example 232 |
| 233 (Z)-isomer | none | 6-(N,N-dimethyl-3-aminopropyl carbamoyl | NA | 90 | see Example 233 |
| 234 (Z)-isomer | none | 6-N,N-dimethyl-aminosulfonyl | (8:2) Dichloromethane:ethylacetate | 15 | see Example 221 |
| 234 (E)-isomer | none | 6-N,N-dimethyl-aminosulfonyl | (8:2) dichloromethane:ethylacetate | 55 | see Example 221 |

TABLE 40

Physical data for compounds synthesized having structural formula XXX.

| | | Elemental analysis | | | | | |
|---|---|---|---|---|---|---|---|
| | Mp. | Carbon | | Hydrogen | | Nitrogen | |
| Example | (° C.) | calculated | found | calculated | found | calculated | found |
| 225 | >300 | 73.90 | 73.42 | 4.38 | 4.74 | 10.14 | 9.91 |
| 226 | 222–5 | 71.47 | 70.96 | 5.85 | 6.20 | 7.94 | 7.45 |

TABLE 40-continued

Physical data for compounds synthesized having structural formula XXX.

| Example | Mp. (° C.) | Elemental analysis | | | | | |
|---|---|---|---|---|---|---|---|
| | | Carbon | | Hydrogen | | Nitrogen | |
| | | calculated | found | calculated | found | calculated | found |
| 227 (0.1 H$_2$O)[1] | 235–7 | 74.01 | 73.61 | 4.89 | 4.90 | 9.59 | 9.29 |
| 228 | 315–8 | 65.71 | 65.33 | 3.57 | 3.61 | 9.02 | 8.96 |
| 229 | 309–12 | 74.47 | 74.50 | 4.86 | 4.92 | 9.65 | 9.46 |
| 230 | 310–12 | 74.47 | 74.15 | 4.86 | 5.03 | 9.65 | 9.70 |
| 231 (Z)-isomer | 215–20 | NA | NA | NA | NA | NA | NA |
| 232 (Z)-isomer | >350 | NA | NA | NA | NA | NA | NA |
| 233 (0.3 H$_2$O)[1] | 250–3 | 67.40 | 67.38 | 6.05 | 6.23 | 13.67 | 13.56 |
| 234 (Z)-isomer | 315–7 | 59.52 | 59.41 | 4.47 | 4.63 | 10.96 | 10.73 |
| 234 (E)-isomer | 248–50 | 59.52 | 59.58 | 4.47 | 4.58 | 10.96 | 10.87 |

[1]The molecular weight calculated for the elemental analysis includes the solvent in the amount indicated.

XXI. (7-Azaindol-3-yl)methylene Benzoxazinones (XXXI).

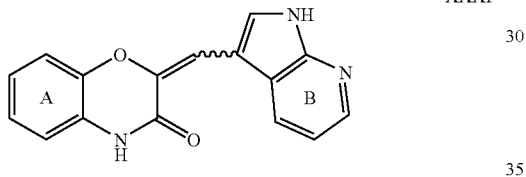

XXXI

Example 235 was synthesized as described in Example 221 using an appropriately substituted 2H-1,4-benzoxazin-3(4H)-one and an appropriately substituted 7-azaindole-3-carboxaldehyde.

TABLE 41

Compound synthesized having structural formula XXXI.

| Example | Substituent on Ring A | Substituent on Ring B | Chromatographic Mobile Phase | % Yield | Method |
|---|---|---|---|---|---|
| 235 | none | none | ethanol | 65 as a mixture of isomers | see Example 221 |

TABLE 42

Physical data for compounds synthesized having structural formula XXXI.

| Example | Mp. (° C.) | Elemental analysis | | | | | |
|---|---|---|---|---|---|---|---|
| | | Carbon | | Hydrogen | | Nitrogen | |
| | | calculated | found | calculated | found | calculated | found |
| 235 (0.2 C$_2$H$_5$OH)[1] | >350 | 68.75 | 68.44 | 4.29 | 4.19 | 14.67 | 14.87 |

[1]The molecular weight calculated for the elemental analysis includes the solvent in the amount indicated.

XXII. (Phenyl)methylene Benzoxazinones (XXXII).

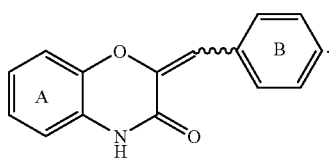

XXXII

Example 236

Synthesis of 2-[(4-Cyanophenyl)methylene]-2H-1,4-benzoxazin-3(4H)-one

4-Cyanobenzaldehyde (1.98 g, 0.015 mol) was added to a mixture of 2H-1,4-benzoxazin-3(4H)-one (1.49 g, 0.01 mol), acetic anhydride (4 ml) and triethylamine (2 ml). The reaction mixture was refluxed for 7 h, left overnight at room temperature and poured into crushed ice. The precipitated solid was collected by filtration and washed with acetonitrile. The crude product was purified by recrystalization from DMF:ethanol.

Example 237

Synthesis of 2-[(4-Dimethylaminophenyl)methylene]-2H-1,4-benzoxazin-3(4H)-one

Sodium methoxide (0.65 g, 0.012 mol) was added in one portion to a mixture of 2H-1,4-benzoxazin-3(4H)-one (1.49 g, 0.01 mol) and 4-dimethylamino benzaldehyde (2.38 g, 0.016 mol) in dry DMF (10 ml). The reaction mixture was refluxed overnight, then cooled to room temperature and poured into crushed ice. The precipitated solid was collected by filtration, washed with water and dried. The crude product was purified by recrystallization from ethanol.

Example 241

Synthesis of 2-[(4-Aminophenyl)methylene]-2H-1,4-benzoxazin-3(4H)-one

A catalytic amount of Raney nickel was added portionwise with stirring to a mixture of 2-[(4-nitrophenyl)methylene]-2H-1,4-benzoxazin-3(4H)-one (0.57 g, 0.002 mol) and hydrazine hydrate (1 ml) in ethanol (20 ml). The reaction mixture was refluxed for 3 h, then filtered. The filtrate was evaporated to dryness under reduced pressure. The crude product was purified by re crystallization from ethanol.

Example 242

Synthesis of 2-[(4-Hydroxyphenyl)methylene]-2H-1,4-benzoxazin-3(4H)-one

A mixture of 2-[(4-acetoxyphenyl)methylene]-2H-1,4-benzoxazin-3(4H)-one (0.49 g, 0.0016 mol) and NaOH 10% (30 ml) was refluxed for 1 h. The reaction mixture was cooled and acidified with 6N HCl. The precipitated was collected by filtration, then washed with water and dried. The crude product was purified by recrystalization from ethanol.

Example 245

2-[(4-Oxamidinophenyl)methylene]-2H-1,4-benzoxazin-3(4H)-one

A mixture of hydroxylamine hydrochloride (145 mg, 2 mmol), sodium carbonate (106 mg, 1 mmol), 2-[(4-cyanophenyl)methylene]-2H-1,4-benzoxazin-3(4H)-one (262 mg, 1 mmol in ethanol (25 ml) and water (3 ml) was refluxed for 25 h. The precipitated solid was filtered off and recristallized from ethanol to give 180 mg (61%).

Table 43 lists the compounds synthesized having structural formula XXXII. Examples 236, 241, 242 and 245 were synthesized as described above. Examples 237–240 were synthesized as described in Example 237. Examples 243 and 244 were synthesized as described in Example 241, and Example 246 was synthesized as described in Example 236 using an appropriately substituted 2H-1,4-benzoxazin-3(4H)-one and an appropriately substituted benzaldehyde.

TABLE 43

Compounds synthesized having structural formula XXXII.

| Example | Substituent on Ring A | Substituent on Ring B | Recrystallization Solvent | % Yield | Method |
|---|---|---|---|---|---|
| 236 | none | 4-CN | DMF-ethanol | 37 | see Example 236 |
| 237 | none | 4-N(CH$_3$)$_2$ | ethanol | 30 | see Example 237 |
| 238 | 6-Cl | 4-N(CH$_3$)$_2$ | DMIF-ethanol | 40 | see Example 237 |
| 239 | 6-CH$_3$ | 4-N(CH$_3$)$_2$ | DMF-ethanol | 45 | see Example 237 |
| 240 | 7-CH$_3$ | 4-N(CH$_3$)$_2$ | acetonitrile | 35 | see Example 237 |
| 241 | none | 4-NH$_2$ | ethanol | 64 | see Example 241 |
| 242 | none | 4-OH | NA | 97 | see Example 242 |
| 243 | 6-NH$_2$ | 4-NH$_2$ | ethanol | 74 | see Example 241 |
| 244 | 7-NH$_2$ | 4-NH$_2$ | ethanol-hexane | 20 | see Example 241 |
| 245 | none | 4-C(=NOH)NH$_2$ | ethanol | 61 | see Example 245 |
| 246 | none | 3,4-(OCOCH$_3$)$_2$ | ethylacetate | 10 | see Example 236 |

TABLE 44

Physical data for compounds synthesized having structural formula XXXII.

| Example | Mp. (° C.) | Carbon calculated | Carbon found | Hydrogen calculated | Hydrogen found | Nitrogen calculated | Nitrogen found |
|---|---|---|---|---|---|---|---|
| 236 | 330–2 | 73.27 | 73.20 | 3.84 | 4.09 | 10.68 | 10.61 |
| 237 | 245–7 | 72.84 | 72.83 | 5.75 | 5.78 | 9.99 | 9.89 |
| 238 | 307–9 | 64.87 | 64.71 | 4.80 | 4.69 | 8.90 | 9.17 |
| 239 | 290–2 | 73.45 | 73.24 | 6.16 | 6.21 | 9.52 | 9.51 |
| 240 | 240–3 | 72.56 | 72.51 | 6.22 | 6.20 | 9.40 | 9.37 |
| 241 | 297–299 | 71.42 | 71.30 | 4.79 | 4.84 | 11.10 | 11.02 |
| 242 | 275–7 | 70.47 | 70.19 | 4.68 | 4.78 | 5.34 | 5.28 |
| 243 | 285–7 | 67.41 | 67.07 | 4.90 | 5.07 | 15.72 | 15.56 |
| 244 | 277–9 | 65.76 | 65.12 | 5.78 | 5.52 | 14.03 | 14.59 |
| 245 | 276–8 | 65.08 | 65.18 | 4.44 | 4.71 | 14.23 | 13.87 |
| 246 | 223–5 | 64.59 | 64.50 | 4.28 | 4.53 | 3.96 | 3.86 |

XXIII. (Thien-3-yl)methylene Benzoxazinones (XXXIII).

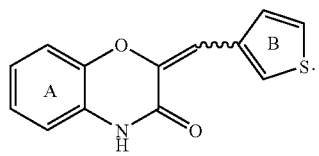

XXXIII

Table 45 lists the compounds synthesized having structural formula XXXIII. Examples 247–249 were synthesized as described in Example 236 using an appropriately substituted 2H-1,4-benzoxazin-3(4H)-one and an appropriately substituted thiophene-3-carboxaldehyde. Examples 248 and 249 were then hydrogenated using the method described in Example 241 to form Examples 250 and 251.

TABLE 45

Compounds synthesized having structural formula XXXIII.

| Example | Substituent on Ring A | Substituent on Ring B | Recrystalization Solvent | % Yield | Method |
|---|---|---|---|---|---|
| 247 | none | none | acetonitrile | 50 | see Example 236 |
| 248 | 6-$NO_2$ | none | DMF | 55 | see Example 236 |
| 249 | 7-$NO_2$ | none | DMF | 57 | see Example 236 |
| 250 | 6-$NH_2$ | none | ethanol | 68 | see Example 241 |
| 251 | 7-$NH_2$ | none | ethanol | 97 | see Example 241 |

TABLE 46

Physical data for compounds synthesized having structural formula XXXIII.

| Example | Mp. (° C.) | Carbon calculated | Carbon found | Hydrogen calculated | Hydrogen found | Nitrogen calculated | Nitrogen found |
|---|---|---|---|---|---|---|---|
| 247 | 256–7 | 64.18 | 63.97 | 3.73 | 3.77 | 5.76 | 5.71 |
| 248 | 284–7 | 54.16 | 53.99 | 2.80 | 2.97 | 9.72 | 9.50 |
| 249 | 335–8 | 54.16 | 54.09 | 2.80 | 2.95 | 9.72 | 9.62 |
| 250 | 295–7 | 60.45 | 60.39 | 3.90 | 3.90 | 10.85 | 10.60 |
| 251 | 243–5 | 60.45 | 60.66 | 3.90 | 4.11 | 10.85 | 10.85 |

XXIV. (Thien-2-yl)methylene Benzoxazinones (XXXIV).

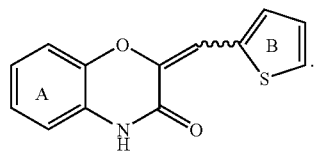

XXXIV

Examples 252, 256 and 257 in Tables 47–52 were synthesized as described in Example 236 using an appropriately substituted 2H-1,4-benzoxazin-3(4H)-one and an appropriately substituted thiophene-2-carboxaldehyde, pyridine-3-carboxaldehyde, or trans-cinnamaldehyde. Example 252 was hydrogenated to form Example 253 using the reaction conditions described in Example 250.

TABLE 47

Compounds synthesized having structural formula XXXIV.

| Example | Substituent on Ring A | Substituent on Ring B | Recrystalization Solvent | % Yield | Method |
|---|---|---|---|---|---|
| 252 | 7-NO$_2$ | none | DMF | 55 | see Example 236 |
| 253 | 7-NH$_2$ | none | ethanol | 81 | see Example 250 |
| 254 | 7-NH$_2$ | 3-CH$_3$ | ethanol | 90 | see Example 241 |
| 255 | 7-NH$_2$ | 5-CH$_3$ | ethanol | 74 | see Example 241 |

TABLE 48

Physical data for compounds synthesized having structural formula XXXIV.

| | | Elemental analysis | | | | |
|---|---|---|---|---|---|---|
| | | Carbon | | Hydrogen | | Nitrogen | |
| Example | Mp. (° C.) | calculated | found | calculated | found | calculated | found |
| 252 | 336–8 | 54.16 | 54.13 | 2.80 | 2.86 | 9.72 | 9.68 |
| 253 | 267–9 | 60.45 | 60.60 | 3.90 | 4.20 | 10.85 | 10.70 |
| 254 | 268–70 | 61.75 | 62.07 | 4.44 | 4.77 | 10.29 | 9.94 |
| 255 | 282–84 | 61.75 | 61.98 | 4.44 | 4.61 | 10.29 | 10.06 |

XXV. 2-[(Pyrid-3-yl)methylene]-2H-1,4-Benzoxazin-3 (4H)-ones (XXXV).

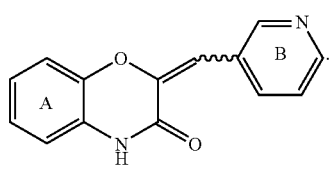

XXXV

TABLE 49

Compounds synthesized having structural formula XXXV.

| Example | Substituent on Ring A | Substituent on Ring B | Recrystalization Solvent | % Yield | Method |
|---|---|---|---|---|---|
| 256 | none | none | ethanol | 34 | see Example 236 |

TABLE 50

Physical data for compounds synthesized having structural formula XXXV.

| | | Elemental analysis | | | | |
|---|---|---|---|---|---|---|
| | | Carbon | | Hydrogen | | Nitrogen | |
| Example | Mp. (° C.) | calculated | found | calculated | found | calculated | found |
| 256 | 257–8 | 70.58 | 70.46 | 4.23 | 4.31 | 11.76 | 11.65 |

XXVI. 2-(Cinnamylidene)-2H-1,4-Benzoxazin-3 (4H)-ones (XXXVI).

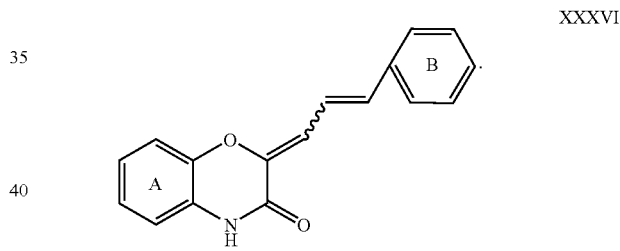

XXXVI

TABLE 51

Compounds synthesized having structural formula XXXVI.

| Example | Substituent on Ring A | Substituent on Ring B | Recrystalization Solvent | % Yield | Method |
|---|---|---|---|---|---|
| 257 | none | none | DMF-acetonitrile | 30 | see Example 236 |

TABLE 52

Physical data for compounds synthesized having structural formula XXXVI.

| | | Elemental analysis | | | | |
|---|---|---|---|---|---|---|
| | | Carbon | | Hydrogen | | Nitrogen | |
| Example | Mp. (° C.) | calculated | found | calculated | found | calculated | found |
| 257 | 295–7 | 77.55 | 77.39 | 4.98 | 5.26 | 5.32 | 5.15 |

XXVII. (Pyrrol-3-yl)methylene Benzoxazinones (XXXVII).

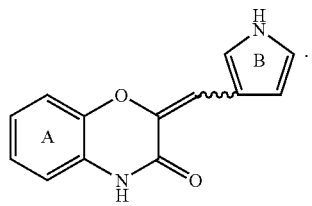

XXXVII

Example 258 was synthesized as described in Example 210 using an appropriately substituted 2H-1,4-benzoxazin-3(4H)-one and an appropriately substituted pyrrol-3-carboxaldehyde.

TABLE 53

Compounds synthesized having structural formula XXXVII.

| Example | Substituent on Ring A | Substituent on Ring B | Chromatographic Mobile Phase | % Yield | Method |
|---|---|---|---|---|---|
| 258 | none | none | (95:5) to (90:10) toluene-ethyl acetate | 15 | see Example 210 |

TABLE 54

Physical data for compounds synthesized having structural formula XXXVII.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 258 | 240 | 69.02 | 68.69 | 4.59 | 4.42 | 12.21 | 12.30 |

XXVIII. (Pyrazol-4-yl)methylene Benzoxazinones (XXXVIII).

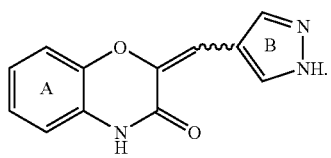

XXXVIII

Example 259 from Table 55 was synthesized as described in Example 210. Examples 260–266 from Tables 55–58 were synthesized as described in Example 221 using an appropriately substituted 2H-1,4-benzoxazin-3(4H)-one and an appropriately substituted pyrazole-4-carboxaldehyde, imidazole-5-carboxaldehyde or imidazole-2-carboxaldehyde.

TABLE 55

Compounds synthesized having structural formula XXXVIII.

| Example | Substituent on Ring A | Substituent on Ring B | Chromatographic Mobile Phase | % Yield (E)-isomer | % Yield (Z)-isomer | Method |
|---|---|---|---|---|---|---|
| 259 | none | 3-CH$_3$ | (50:50) ethyl acetate: dichlorometane | NA | 20 | see Example 210 |
| 260 | none | 3-CH$_3$ | (50:50) to (30:70) dichloromethane: ethylacetate | 66 | 12 | see Example 221 |

TABLE 56

Physical data for compounds synthesized having structural formula XXXVIII.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 259 (Z)-isomer | 323–5 | 64.72 | 64.48 | 4.59 | 4.66 | 17.41 | 17.20 |
| 260 (E)-isomer (0.5 C$_2$H$_5$OH)[1] | 271–3 | 63.62 | 63.04 | 5.33 | 5.04 | 15.90 | 16.07 |

TABLE 56-continued

Physical data for compounds synthesized having structural formula XXXVIII.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 260 (Z)-isomer (0.2 C$_2$H$_5$OH)[1] | 321–3 | 64.24 | 64.44 | 4.91 | 4.91 | 16.78 | 16.48 |

[1]The molecular weight calculated for the elemental analysis includes the solvent in the amount indicated.

XXVIX. (Imidazol-5-yl)methylene Benzoxazinones (XXXIX).

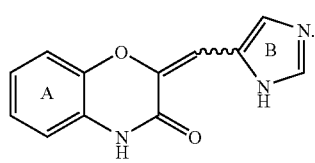

XXXIX

Example 261

Synthesis of (E)-2-[(Imidazol-5-yl)methylene]-2H-1,4-benzoxazin-3(4H)-one hydrochloride A solution 1 M of HCl in ethyl ether (7 ml) was dropwise to a mixture of (E)-2[(imidazol-5-yl)methylene]-2H-1,4-benzoxazinone (0.76 g, 0.0033 mol) in dichloromethane:ethanol 2:1 (120 ml). The reaction mixture was stirred at room temperature for 20 h. The precipitated solid was collected by filtration, washed with dichloromethane and dried. Yield 0.58 g (66%).

TABLE 57

Compounds synthesized having structural formula XXXIX.

| Example | Substituent on Ring A | Substituent on Ring B | Chromatographic Mobile Phase | % Yield (E)-isomer | % Yield (Z)-isomer | Method |
|---|---|---|---|---|---|---|
| 261 | none | none | (95:5) to (80:20) toluene:ethanol | 70 | 17 | see Example 221 |
| 261 (salt) | none | none | NA | 66 | — | see Example 261 (salt) |
| 262 | none | 4-CH$_3$ | (90:10) toluene:methanol | 63 | 16 | see Example 221 |
| 263 | none | 4-CH$_2$OH | NA | 70 | — | see Example 221 |
| 264 | none | 1-Methyl-2-methylthio | NA | 64 | — | see Example 221 |

TABLE 58

Physical data for compounds synthesized having structural formula XXXIX.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 261 (E)-isomer | 272–4 | 63.43 | 63.23 | 3.99 | 4.06 | 18.49 | 18.20 |
| 261 (salt) (E)-isomer (0.3 H$_2$O)[1] | 268–71 | 53.56 | 53.53 | 3.97 | 3.84 | 15.61 | 15.42 |
| 261 (Z)-isomer | >300 | 63.43 | 62.82 | 3.99 | 4.06 | 18.49 | 17.64 |
| 262 (E)-isomer (0.3 C$_2$H$_5$OH)[1] | 275–7 | 63.93 | 63.54 | 5.13 | 4.80 | 16.33 | 16.40 |
| 262 (Z)-isomer (0.2 C$_2$H$_5$OH)[1] | 297–300 | 64.26 | 63.79 | 4.91 | 4.98 | 16.78 | 16.55 |
| 263 (E)-isomer | 262–4 | 15.77 | 15.88 | 4.61 | 4.43 | 60.40 | 60.04 |
| 264 (E)-isomer | 247–9 | 58.52 | 58.57 | 4.56 | 4.80 | 14.62 | 14.64 |

[1]The molecular weight calculated for the elemental analysis includes the solvent in the amount indicated.

XXX. (Imidazol-2-yl)methylene Benzoxazinones (XL).

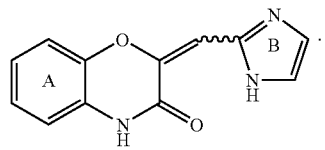

XL

TABLE 59

Compounds synthesized having structural formula XL.

| Example | Substituent on Ring A | Substituent on Ring B | Chromatographic Mobile Phase | % Yield (E)-isomer | % Yield (Z)-isomer | Method |
|---|---|---|---|---|---|---|
| 265 | none | none | (93:7) Toluene:ethanol | 63 | — | see Example 221 |
| 266 | none | 4-trifluoro methyl | (95:5) to (90:10) dichloromethane: ethylacetate to dichloromethane:ethanol | 65 | 16 | see Example 221 |
| 267 | none | 4-carboxy | NA | 71 | — | * |

*This compound was obtained from the corresponding (imidazol-2-yl)methylene benzoxazinone already described by methods well known for those skilled in the art.

TABLE 60

Physical data for compounds synthesized having structural formula XL.

| Example | Mp. (° C.) | Carbon calculated | Carbon found | Hydrogen calculated | Hydrogen found | Nitrogen calculated | Nitrogen found |
|---|---|---|---|---|---|---|---|
| 265 (E)-isomer | 304–6 | 63.43 | 63.03 | 3.99 | 4.01 | 18.49 | 18.28 |
| 266 (E)-isomer | 290–2 | 52.89 | 52.59 | 2.73 | 2.98 | 14.23 | 13.90 |
| 266 (Z)-isomer | 314–6 | 52.89 | 52.24 | 2.73 | 2.83 | 14.23 | 13.80 |
| 267 (Z)-isomer | >300 | 57.57 | 57.38 | 3.34 | 3.34 | 15.49 | 15.23 |

XXXI. Vinylidene Benzothiazine Thiones (XLI).

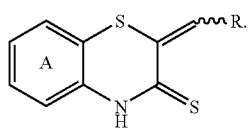

XLI

Example 268

Synthesis of 2-[(Indol-3-yl)methylene]-2H-1,4-benzothiazine-3(4H)-thione

A mixture of 2H-1,4-benzothiazin-3(4H)-thione (0.36 g, 2.0 mol), indole-3-carboxaldehyde (0.33 g, 2.3 mmol) and piperidine (3 drops) in dry ethanol (8 ml) was refluxed for 9 h. After cooling the precipitate was collected by filtration and the crude product was purified by recrystalization from toluene.

Examples 268–270 in Table 61 were synthesized as described in Example 268 using an appropriately substituted 2H-1,4-benzothiazin-3(4H)-thione and indole-3-carboxaldehyde, 7-azaindole-3-carboxaldehyde, or pyrrole-2-carboxaldehyde.

TABLE 61

Compounds synthesized having structural formula XLI.

| Example | R | Recrystalization Solvent | % Yield | Method |
|---|---|---|---|---|
| 268 | Indol-3-yl | toluene | 83 | see Example 268 |
| 269 | 7-azaindol-3-yl | DMF-acetonitrile | 87 | see Example 268 |
| 270 | Pyrrol-2-yl | ethyl acetate-hexane | 64 | see Example 268 |

TABLE 62

Physical data for compounds synthesized having structural formula XLI.

| Example | Mp. (° C.) | Carbon calculated | Carbon found | Hydrogen calculated | Hydrogen found | Nitrogen calculated | Nitrogen found |
|---|---|---|---|---|---|---|---|
| 268 | 253–6 | 66.20 | 66.16 | 3.92 | 4.01 | 9.08 | 8.96 |
| 269 | 287–90 | 62.11 | 61.88 | 3.58 | 3.91 | 13.58 | 13.57 |
| 270 | 205–6 | 60.44 | 60.23 | 3.90 | 3.92 | 10.84 | 10.71 |

XXXII. Vinylidene Benzoxazine Thiones (XLII).

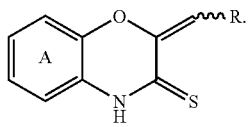

XLII

Example 271

Synthesis of 2-[(Pyrrol-2-yl)methylene]-2H-1,4-benzoxazin-3 (4H)-thione

A mixture of 2H-1,4-benxoxazin-3(4H)-thione (0.33 g, 0.002 mol), pyrrole-2-carboxaldehyde (0.2 g, 0.021 mol) and 3 drops of piperidine in ethanol (14 ml) was refluxed for 3 h. The reaction mixture was cooled to room temperature and the precipitated product was collected by filtration. The crude product was washed with ethanol, then purified by recrystalization from toluene.

Examples 271 and 272 in Table 63 were synthesized as described in Example 271 using 2H-1,4-benzothiazin-3(4H)-thione and indole-3-carboxaldehyde or pyrrole-2-carboxaldehyde.

TABLE 63

Compounds synthesized having structural formula XLII.

| Example | R | Recrystalization Solvent | % Yield | Method |
|---|---|---|---|---|
| 271 | Pyrrol-2-yl | Toluene | 64 | see Example 271 |
| 272 | indol-3-yl | Ethanol | 67 | see Example 271 |

TABLE 64

Physical data for compounds synthesized having structural formula XLII.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 271 | 241–3 | 64.44 | 64.61 | 4.16 | 4.10 | 11.56 | 11.30 |
| 272 | 275–7 | 69.84 | 69.65 | 4.14 | 4.18 | 9.58 | 9.34 |

XXXIII. Imino Vinylidene Benzothiazines (XLIII).

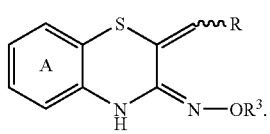

XLIII

Example 273

Synthesis of 3-Hydroxyimino-2-[(pyrrol-2-yl)methylene]-2H-1,4-benzothiazine

A mixture of 2-[(pyrrol-2-yl)methylene]-2H-1,4-benzothiazine-3(4H)-thione (1.70 g, 6.6 mmol) (Example 270), hydroxylamine hydrochloride (1.38 g, 20.0 mmol) and triethylamine (2.18 g, 20.0 mmol) in dry ethanol (50 ml) was refluxed for 24 h with stirring. The solvent was removed in vacuo and the residue was purified by silica gel chromatography using (9:1) hexane:ethanol as the mobile phase.

Example 276

Synthesis of 3-Acetyloxyimino-2-[(pyrrol-2-yl)methylene]-2H-1,4-benzothiazine

Acetic anhydride (1.3 ml, 13.78 mmol) was added to a solution of 3-hydroxyimino-2-[(pyrrol-2-yl)methylene]-2H-1,4-benzothiazine (0.27 g, 1.05 mmol) (Compound 273) in dry pyridine (1.5 ml). The reaction mixture was stirred for 30 minutes at room temperature, poured into ice water and extracted with ethyl acetate. The organic layer was washed with 10% HCl and brine, dried over magnesium sulfate and brought to dryness in vacuo. The residue was purified by silica gel chromatography using (9:1) dichloromethane:ethanol as the mobile phase.

Example 277

Synthesis of 3-Benzoyloxyimino-2-[(pyrrol-2-yl)methylene]-2H-1,4-benzothiazine

A mixture of 3-hydroxyimino-2-[(pyrrol-2-yl)methylene]-2H-1,4-benzothiazine (0.28 g, 1.09 mmol) (Compound 273), benzoyl chloride (0.15 g, 1.09 mmol) and dry pyridine (2 drops) in dry toluene (5 ml) was stirred at room temperature for 4 hours. The precipitate was collected by filtration, washed with toluene, then purified by silica gel chromatography using (25:1) dichloromethane:ethyl acetate as the mobile phase.

Compounds 274 and 275 in Table 65 were synthesized as described in Example 273 except that 2-[(indol-3-yl)methylene]-2H-1,4-benzothiazine-3(4H)-thione (Compound 268) or 2-[(7-azaindol-3-yl)methylene]-2H-1,4-benzothiazine-3(4H)-thione (Compound 269) was substituted for 2-[(pyrrol-2-yl)methylene]-2H-1,4-benzothiazine-3(4H)-thione.

TABLE 65

Compounds synthesized having structural formula XLIII.

| Example | R | R³ | Chromatographic Solvent | % Yield | Method |
|---|---|---|---|---|---|
| 273 | pyrrol-2-yl | H | (9:1) hexane:ethanol | 55 | see Example 273 |
| 274 | indol-3-yl | H | (9:1) hexane:ethanol | 18 | see Example 273 |
| 275 | 7-azaindol-3-yl | H | (9:1) hexane:ethanol | 10 | see Example 273 |
| 276 | pyrrol-2-yl | acetyl | (9:1) dichloromethane:ethanol | 71 | see Example 276 |
| 277 | pyrrol-2-yl | benzoyl | (25:1) dichloromethane:ethyl acetate | 46 | see Example 277 |

TABLE 66

Physical data for compounds synthesized having structural formula XLIII.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 273 | 204–5 | 60.68 | 60.84 | 4.31 | 4.48 | 16.33 | 16.28 |
| 274 | 295–8 | 66.43 | 66.49 | 4.26 | 4.28 | 13.67 | 13.73 |
| 275 | >330 | 62.32 | 62.09 | 3.92 | 4.10 | 18.17 | 17.81 |
| 276 | 182–5 | 60.19 | 60.22 | 4.38 | 4.45 | 14.04 | 13.98 |
| 277 | 188–9 | 66.47 | 66.38 | 4.18 | 4.21 | 11.63 | 11.56 |

XXXIV. Imino Vinylidene Benzoxazines (XLIV).

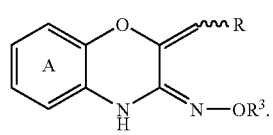

XLIV

Example 278

Synthesis of 3-Hydroxyimino-2-[(pyrrol-2-yl)methylene]-2H-1,4-benzoxazine

A mixture of 2-[(pyrrol-2-yl)methylene]-2H-1,4-benzoxazin-3(4H)-thione (0.17 g, 0.7 mmol) (Example 271), hydroxylamine hydrochloride (0.45 g, 6.0 mmol) and triethylamine (0.6 ml, 6.0 mmol) in ethanol (10 ml) was refluxed for 6 h. The solvent was evaporated under reduced pressure, and the residue was stirred with ethyl acetate (30 ml) and filtered. The filtrate was evaporated to dryness to give the crude product which was purified by recrystalization from ethyl acetate:hexane.

Compound 279 in Table 67 was synthesized as described in Example 278 except that 2-[(indol-3-yl)methylene]-2H-1,4-benzoxazin-3(4H)-thione was substituted for 2-[(pyrrol-2-yl)methylene]-2H-1,4-benzoxazin-3(4H)-thione.

TABLE 67

Compounds synthesized having structural formula XLIV.

| Example | R | $R^3$ | Recrystalization Solvent | % Yield | Method |
|---|---|---|---|---|---|
| 278 | pyrrol-2-yl | H | ethyl acetate:hexane | 65 | see Example 278 |
| 279 | indol-3-yl | H | ethyl acetate:hexane | 84 | see Example 278 |

TABLE 68

Physical data for compounds synthesized having structural formula XLIV.

| | | Elemental analysis | | | | |
|---|---|---|---|---|---|---|
| | | Carbon | | Hydrogen | | Nitrogen | |
| Example | Mp. (° C.) | calculated | found | calculated | found | calculated | found |
| 278 | 192–4 | 64.72 | 64.43 | 4.60 | 4.53 | 17.42 | 17.15 |
| 279 | 226–8 | 70.09 | 69.75 | 4.50 | 4.57 | 14.42 | 14.18 |

XXXV. 1,1-Dioxo Vinylidene Benzothiazinones (XLV).

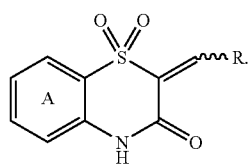

XLV

Example 280

Synthesis of 1,1-Dioxo-2-[(indol-3-yl)methylene]-2H-1,4-benzothiazin-3(4H)-one A mixture of 1,1-dioxo-2H-1,4-benzothiazin-3(4H)-one (0.59 g, 3.0 mmol), indole-3-carboxaldehyde (0.48 g, 3.3 mmol) and piperidine (3 drops) in anhydrous ethanol (6 ml) was refluxed for 17 h. After cooling to room temperature, the precipitate was collected by filtration and purified by recrystalization from ethyl acetate:hexane.

Compounds 281 and 282 in Table 69 were synthesized as described in Example 280 except that 7-azaindole-3-carboxaldehyde or pyrrole-2-carboxaldehyde was substituted for indole-3-carboxaldehyde.

TABLE 69

Compounds synthesized having structural formula XLV.

| Example | R | Recrystalization Solvent | % Yield | Method |
|---|---|---|---|---|
| 280 | indol-3-yl | ethyl acetate:hexane | 94 | see Example 280 |
| 281 | 7-azaindol-3-yl | DMF:H$_2$O | 88 | see Example 280 |
| 282 | pyrrol-2-yl | ethanol | 97 | see Example 280 |

TABLE 70

Physical data for compounds synthesized having structural formula XLV.

| | | Elemental analysis | | | | |
|---|---|---|---|---|---|---|
| | | Carbon | | Hydrogen | | Nitrogen | |
| Example | Mp. (° C.) | calculated | found | calculated | found | calculated | found |
| 280 | 318–20 | 62.95 | 62.73 | 3.73 | 3.78 | 8.64 | 8.64 |
| 281 | 330–2 | 59.07 | 58.70 | 3.41 | 3.68 | 12.92 | 13.03 |
| 282 | 225–7 | 56.92 | 56.92 | 3.67 | 3.62 | 10.21 | 10.10 |

XXXVI. 1-Oxo Vinylidene Benzothiazinones (XLVI)

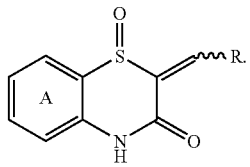

XLVI

Compound 283 in Table 71 was synthesized as described in Example 280 except that 1-oxo-2H-1,4-benzothiazin-3(4H)-one was used instead of 1,1]-dioxo-2H-1,4-benzothiazin-3(4H)-one and 7-azaindole-3-carboxaldehyde was used instead of indole-3-carboxaldehyde. Compound 284 was synthesized as described in Example 280 except that 1-oxo-2H-1,4-benzothiazin-3(4H)-one was used instead of 1,1-dioxo-2H-1,4-benzothiazin-3(4H)-one.

TABLE 71

Compounds synthesized having structural formula XLVI.

| Example | R | Recrystalization Solvent | % Yield | Method |
|---|---|---|---|---|
| 283 | 7-azaindol-3-yl | DMF:H$_2$O | 63 | see Example 280 |
| 284 | indol-3-yl | NA | 36 | see Example 280 |

TABLE 72

Physical data for compounds synthesized having structural formula XLVI.

| Example | Mp. (° C.) | Carbon calculated | Carbon found | Hydrogen calculated | Hydrogen found | Nitrogen calculated | Nitrogen found |
|---|---|---|---|---|---|---|---|
| 283 | 292–4 | 62.12 | 61.91 | 3.58 | 3.70 | 13.58 | 13.43 |
| 284 | 276–8 | 66.22 | 65.82 | 3.92 | 4.02 | 9.08 | 8.98 |

XXXVII. 1,1-Dioxo Aminomethylene Benzothiazinones (XLVII).

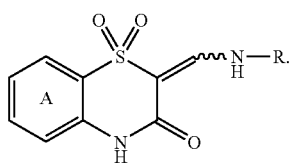

XLVII

Example 285

Synthesis of 1,1 Dioxo-2-[(4-methoxyphenylamino)methylene]-2H-1,4-benzothiazin-3(4H)-one A mixture of 1,1]-dioxo-2-dimethylaminomethylene-2H-1,4-benzothiazin-3 (4H)-one (0.25 g, 1.0 mmol) and 4-methoxyaniline (0.27 g, 2.2 mmol) in dry ethanol (20 ml) was refluxed for 1 h. After cooling to room temperature, the precipitate was collected by filtration, washed with ethanol and purified by recrystalization using DMF:water.

Compounds 286–294 in Table 73 were synthesized using the method of Example 285 except 4-methoxyaniline was replaced by the appropriate amine.

TABLE 73

Compounds synthesized having structural formula XLVII.

| Example | R | Recrystalization Solvent | % Yield | Method |
|---|---|---|---|---|
| 285 | 4-methoxyphenyl | DMF:H$_2$O | 94 | see Example 285 |
| 286 | 4-methylphenyl | DMF:H$_2$O | 94 | see Example 285 |
| 287 | 4-dimethylaminophenyl | DMF:H$_2$O | 94 | see Example 285 |
| 288 | phenyl | DMF:H$_2$O | 60 | see Example 285 |
| 289 | 4-chlorophenyl | DMF:H$_2$O | 78 | see Example 285 |
| 290 | pyrazol-3-yl | DMF:H$_2$O | 69 | see Example 285 |
| 291 | 1,2,4-triazol-3-yl | NA | 34 | see Example 285 |
| 292 | indazol-5-yl | DMF:H$_2$O | 82 | see Example 285 |
| 293 | pyrid-3-yl | NA | 24 | see Example 285 |
| 294 | indol-5-yl | DMF:H$_2$O | 82 | see Example 285 |

TABLE 74

Physical data for compounds synthesized having structural formula XLVII.

| Example | Mp. (° C.) | Carbon calculated | Carbon found | Hydrogen calculated | Hydrogen found | Nitrogen calculated | Nitrogen found |
|---|---|---|---|---|---|---|---|
| 285 | 250–1 | 58.17 | 58.14 | 4.27 | 4.34 | 8.48 | 8.51 |
| 286 | 264–6 | 61.13 | 61.12 | 4.49 | 4.37 | 8.91 | 9.02 |
| 287 | 278–80 | 59.46 | 59.48 | 4.99 | 4.78 | 12.24 | 12.34 |
| 288 | 255–6 | 59.99 | 59.96 | 4.03 | 4.03 | 9.33 | 9.44 |
| 289 | 299–300 | 53.82 | 53.72 | 3.31 | 3.12 | 8.37 | 8.36 |
| 290 | 298–300 | 49.65 | 49.83 | 3.47 | 3.60 | 19.30 | 19.23 |
| 291 | 307–9 | 45.36 | 45.51 | 3.11 | 3.17 | 24.04 | 23.90 |
| 292 | 320–3 | 56.46 | 56.09 | 3.55 | 3.62 | 16.46 | 16.30 |
| 293 | 285–6 (0.25 H$_2$O)[1] | 54.98 | 55.00 | 3.79 | 3.74 | 13.74 | 13.56 |
| 294 | 268–70 | 60.17 | 59.85 | 3.86 | 4.06 | 12.38 | 12.34 |

[1]The molecular weight calculated for the elemental analysis includes the solvent in the amount indicated.

XXXVIII. Vinylidene Pyridoxazinones (XLVIII).

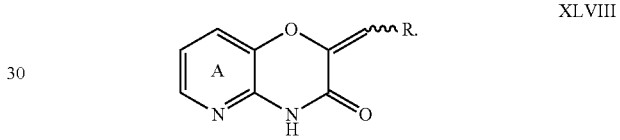

XLVIII

Example 295

Synthesis of 2-[(Pyrrol-2-yl)methylene]-2H-pyrido[3,2-b][1,4]oxazin-3(4H)-one

Sodium methoxide (0.65 g, 0.012 mol) was added in one portion to a mixture of 2H-pyrido[3,2-b][1,4]oxazin-3(4H)-one (1.50 g, 0.01 mol) and pyrrole-2-carboxaldehyde (1.58 g, 0.016 mol) in dry DMF (10 ml). The reaction mixture was refluxed for 48 h, then cooled to room temperature, poured into crushed ice and left overnight at 4° C. The precipitated solid was filtered off, washed with water and dried. The dark solid was boiled with ethanol (150 ml) and filtered hot to remove impurities. The filtrate was evaporated to dryness under reduced pressure, and the residue was purified by silica gel chromatographed using (95:5) toluene:ethyl acetate as the mobile phase.

Example 297

Synthesis of 2-(Phenylmethylene)-2H-pyrido[3,2-b][1,4]oxazin-3(4H)-one

Benzaldehyde (1.59 g, 0.016 mol) was added to a mixture of 2H-pyrido[3,2-b][1,4]oxazin-3(4H)-one (1.50 g, 0.01 mol), acetic anhydride (4 ml) and triethylamine (2 ml). The reaction mixture was refluxed for 72 h, then cooled to room temperature. The precipitated solid was collected by filtration, washed with acetonitrile and purified by silica gel chromatography using (8:2) toluene:ethyl acetate.

Compound 296 was synthesized using the method described in Example 295 except that indole-3-carboxaldehyde was substituted for pyrrole-2-carboxaldehyde.

TABLE 75

The following vinylidene pyridoxazinones (XLVIII) were synthesized.

| Example | R | Chromatographic Solvent | % Yield | Method |
|---|---|---|---|---|
| 295 (E)-isomer | pyrrol-2-yl | (95:5) toluene:ethyl acetate | 2 | see Example 295 |
| 295 (Z)-isomer | pyrrol-2-yl | (95:5) toluene:ethyl acetate | 15 | see Example 295 |
| 296 | indol-3-yl | NA | 20 | see Example 295 |
| 297 | phenyl | (8:2) toluene:ethyl acetate | 12 | see Example 297 |

TABLE 76

Physical data for compounds synthesized having structural formula XLVIII.

| | | Elemental analysis | | | | |
|---|---|---|---|---|---|---|
| | | Carbon | | Hydrogen | | Nitrogen |
| Example | Mp. (° C.) | calculated | found | calculated | found | calculated | found |
| 295 (E)-isomer | 254–5 | 63.43 | 63.55 | 3.99 | 4.12 | 18.49 | 18.20 |
| 295 (Z)-isomer | 306–9 | 63.43 | 63.65 | 3.99 | 4.23 | 18.49 | 18.23 |
| 296 | 320–8 | 69.30 | 68.97 | 3.99 | 4.35 | 15.15 | 15.04 |
| 297 | 223–5 | 70.58 | 70.52 | 4.23 | 4.41 | 11.76 | 11.55 |

XXXIX. Synthesis of Starting Materials.

A. 1-substituted pyrrole-2-carboxaldehydes

Example 298

Synthesis of 1-(2-hydroxyethyl)-2-pyrrolcarboxaldehyde

A solution of 2-pyrrolcarboxaldehyde (1.90 g, 0.02 m) in dry DMF (35 ml) was added dropwise, under nitrogen atmosphere, to a stirred suspension of 60% sodium hydride (oil dispersion) (0.96 g, 0.022 ml) in dry DMF (40 ml), keeping the temperature at 0° C. After addition was completed, stirring was continued at the same temperature for 30 min. Then a solution of 2-bromo ethylacetate (3.63 g, 0.022 m) in dry DMF (10 ml) was added dropwise and the temperature was allowed to rise to room temperature. The reaction mixture was stirred at this temperature fro 48 h. Then water (150 ml) was added and the mixture extracted with dichloromethane. The organic phase was dried over anhydrous magnesium sulfate and the solvent removed under reduced pressure to give 1 (2-acetoxyethyl)-2-pyrrol carboxaldehyde as an oil. Sodium-hydroxide (1.50 g) in water (37 ml) was added to a solution of this oil in methanol (50 ml) and the mixture was heated at 60° C. for ½ hour. Solvent was removed and water (50 ml) was added. The mixture was extracted with ethyl acetate. The organic phase was dried and the solvent removed under reduced pressure to afford a red oil which was purified by column chromatography using toluene:ethanol 98:2 to 95:5 as eluent. Yield: 1.89 g (68%) 1-(4-hydroxybutyl)-2-pyrrolcarboxaldehyde was prepared following the same procedure described in example 298.

B. 1-substituted (7-aza)indole-3-carboxaldehydes.

Example 299

Synthesis of 1-benzoyloxyethyloxymethyl-7-azaindole-3-carboxaldehyde

A solution of 7-azaindole-3-carboxaldehyde (2 g, 13.7 mmol) in dry N,N-dimethylformamide (30 ml) was added dropwise, under nitrogen atmosphere, to a stirring suspension of 60% sodium hydride (oil dispersion) (0.6 g, 15 mmol) in dry N,N-dimethylformamide (10 ml) keeping the temperature between 5–10° C. (ice-water bath). After addition was completed, stirring was continued at the same temperature for 30 min. Then a solution of benzoyloxyethyl chloromethyl ether (3.8 g, 15 mmol) in dry N,N-dimethylformamide (40 ml) was added dropwise. After addition was complete, a catalytic amount of sodium iodide was added, and the temperature was allowed to rise to room temperature. The reaction mixture was allowed to stand at room temperature under nitrogen for 6 days, with intermittent stirring. Then water (100 ml) was added, and the mixture extracted with dichloromethane (3×100 ml). The organic phase was washed with water (100 ml), dried over anhydrous magnesium sulfate, filtered and the solvent removed under reduced pressure to give an oil (4.4 g, 99%), which was used without further purification.

Example 300

Synthesis of 1-Hydroxyethyloxymethyl-7-azaindole-3-carboxaldehyde

A solution of sodium hydroxide (1.33 g, 33 mmol) in water (35 ml) was added to a solution of 1-benzoyloxyethyloxymethyl-7-azaindole-3-carboxaldehyde (5.4 g, 16 mmol) in methanol (45 ml). The mixture was heated at 60° C. for 1 h, then the solvent was concentrated to half the original volume. Water was added, and the product was extracted with dichloromethane, dried over magnesium sulfate, filtered then evaporated to dryness. The product was used without further purification. Yield 2.7 g (74%)

Example 310

1-(2,3-epoxypropyl)-indole-3-carboxaldehyde

Potassium hydroxide (0.38 g, 6.9 mmol) was added to a stirred suspension of indole-3-carboxaldehyde (1 g; 6.9 mmol) in ethanol (100 ml). The mixture was stirred at room temperature for 15 min. The solvent was removed and the residue was treated with epichlorhydrin (4 ml) followed by heating at 100° C. for 12 h. The mixture was then allowed to cool, and the precipitated solid removed by filtration. The filtrate was evaporated under reduced pressure, and the residue chromatographed (silica gel, eluent toluene:ethanol 97:3) to yield 0.52 g (38%) of 1-(2,3-epoxypropyl)-indole-3-carboxaldehyde as an oil.

Example 311

1-(2-hydroxy-N,N-dimethyl-3-aminopropyl)indole-3-carboxaldehyde

A mixture of 1-(2,3-epoxypropyl)indole-3-carboxaldehyde (0.5 g, 2.5 mmol), N,N-dimethylamine hydrochloride (4 g, 49 mmol) and anhydrous potassium hydroxide (2.75 g, 49 mmol) was stirred in dry methanol (50 ml) at −30° C. for 8 h., then allowed to slowly warm to room temperature. The mixture was concentrated under reduced pressure to half the original volume, then water was added and the mixture was extracted with dichloromethane. After drying with anhydrous sodium sulfate the solvent was removed under reduced pressure, and the oily residue was chromatographed on a silica gel column (eluent dichloromethane:methanol from (9:1) to (8:2)) to yield the entitled product as a yellow oil 0.49 g (80%).

Example 318

1-[3-Tetrahydrofuranyl]indole-3-carboxaldehyde

Indole-3-carboxaldehyde (0.72 g, 0.005 mol), 3-iodo tetrahydrofuran (0.99 g, 0.005 mol) and anhydrous potassium carbonate (0.69 g, 0.005 mol) in anhydrous N,N-dimethylformamide (7 ml) was stirred at 120° C. for 6 h. The reaction mixture was filtered and the filtrate was evaporated to dryness. The residue was chromatographed on a silica gel column using toluene:ethyl acetate 95:5 as eluent to yield 0.15 g (14%) of the entitled product as an oil.

Aldehydes included in Table 77 were prepared following procedures described for compounds 299, 300, 310, 311 and 318 using the appropriate halogen derivative and the corresponding indole-3-carboxaldehyde or 7-azaindole-3-carboxaldehyde.

TABLE 77

1-Substituted (7-aza)indole-3-carboxaldehydes synthesized.

XLIX

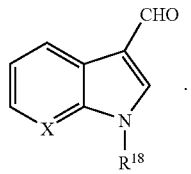

| Example | X | R$^{18}$ |
|---|---|---|
| 299 | N | —CH$_2$—O—CH$_2$—CH$_2$—OCOPh |
| 300 | N | —CH$_2$—O—CH$_2$—CH$_2$—OH |
| 301 | CH | —CH$_2$—O—CH$_2$—CH$_2$—OCOPh |
| 302 | CH | —CH$_2$—O—CH$_2$—CH$_2$—OH |
| 303 | CH | —CH$_2$—CH$_2$—CH$_2$—N(CH$_3$)$_2$ |
| 304 | N | —CH$_2$—CH$_2$—CH$_2$—N(CH$_3$)$_2$ |
| 305 | N | H$_2$CH$_2$C—N(morpholino) |
| 306 | CH | —CH$_2$—CH$_2$—CH$_2$—CH$_2$—OCOCH$_3$ |
| 307 | N | —CH$_2$—CH$_2$—CH$_2$—CH$_2$—OCOCH$_3$ |
| 308 | CH | —CH$_2$—CH$_2$—CH$_2$—CH$_2$—OH |
| 309 | N | —CH$_2$—CH$_2$—CH$_2$—CH$_2$—OH |
| 310 | CH | —CH$_2$—CH(epoxide)—CH$_2$ |
| 311 | CH | —CH$_2$—CH(OH)—CH$_2$—NMe$_2$ |
| 312 | N | —CH$_2$—CO$_2$CH$_2$CH$_3$ |
| 313 | CH | —CH$_2$—CONH$_2$ |
| 314 | CH | —CH$_2$—CH$_2$—CO$_2$CH$_2$CH$_3$ |
| 315 | CN | —CO—N(CH$_2$CH$_3$)$_2$ |
| 316 | N | —CH$_2$—O—CH$_3$ |
| 317 | N | —CH$_2$—CH$_2$—N(CH$_3$)$_2$ |
| 318 | CH | 3-tetrahydrofuranyl |

C. Indole-3-carboxaldehydes.

Example 319

Synthesis of 7-methoxycarbonyl-3-indolcarboxaldehyde

To a stirred mixture of phosphorus oxychloride-dimethylformamide in anhydrous 1,2-dichloroethane (prepared by the slow addition of phosphorus oxychloride (0.43 ml, 4.6 mmol) to anhydrous DMF (0.35 ml, 4.6 mmol) in anhydrous 1,2-dichloroethane (6 ml) cooled below 5° C.) a solution of 7-methoxycarbonylindole (0.69 g, 4 mmol) in anhydrous 1,2-dichloroethane (6 ml) was dropwise below 5° C. The mixture was stirred at room temperature for 2 h and then was heated at 50° C. for 30 minutes. After cooling, the precipitate was filtered off and washed with 1,2-dichloroethane. This precipitate was suspended in aq Na$_2$CO$_3$ 10% (30 ml) and stirred at room temperature for 20 minutes; dichloromethane was added and stirring was continued 10 minutes more. The organic phase was separated and the aqueous phase was extracted with dichloromethane. The combined organic extracts were washed with brine, dried over anhydrous magnesium sulfate and evaporated to yield 0.75 g (93%) of the entitled product. Mp: 153–4° C.

Example 320

Synthesis of 6-[(2-methoxyethyl)aminomethyl]indole-3-carboxaldehyde

To a solution of 6-carboxyindole (1.5 g, 9.3 mmol) in dry N,N-dimethyl formamide (20 ml), 1,1'-carbonyldiimidazole (1.51 g, 9.3 mmol) was added under nitrogen atmosphere, and the mixture heated at 40° C. for 1 h. Then 2-methoxyethylamine (1.39 g, 18.0 mmol) was added and the mixture heated at the same temperature for an additional time of 20 h. The solvent was removed under reduced pressure and the residue treated with water and extracted with dichloromethane. The organic layer was dried over anhydrous sodium sulfate. Filtration and elimination of the solvent under reduced pressure gave an oil which was identified as 6-[N-(2-methoxyethyl)carbamoyl]indole, and used without further purification in the next step.

To a suspension of lithium aluminum hydride (0.93 g, 24.5 mmol) in anhydrous tetrahydrofurane (15 ml), aluminum trichloride (3.5 g, 24.5 mmol) was added portionwise at 0° C. for 30 min and then 6-[N-(2-methoxyethyl)carbamoyl]indole (1 g, 4.5 mmol) was added portionwise at 0° C. for 1 h. After stirring overnight at room temperature, the reaction mixture was quenched with 20% NaOH while cooling in ice water. The precipitate was filtered and washed with dichloromethane and the solvent evaporated after dried over anhydrous sodium sulfate. The residue was chromatographed on silica gel (eluent, dichloromethane:methanol, 9:1) and then the product was precipitated with hexane to give 0.3 g (32%) of 6-[(2-methoxyethyl)aminomethyl]indole.

To a stirred mixture of phosphorous oxychloride-dimethylformamide in anhydrous 1,2-dichloroetane, prepared by the slow addition of phosphorous oxychloride (0.25 ml, 2.7 mmol) to anhydrous DMF (0.19 ml, 2.9 mmol) in 1,2-dichloroethane (5 ml) cooled below 5° C., a solution of 6-[(2-methoxyethyl)-aminomethyl]indole (0.5 g, 2.5 mmol) in anhydrous 1,2-dichloroethane (5 ml) was added dropwise below 5° C. The mixture was stirred at room temperature for 24 h. Then, water and 10% sodium hydroxide were added to pH=9. The mixture was extracted with dichloromethane and the pH of the aqueous layer adjusted to pH=7 with 10% HCl. The mixture was evaporated to dryness under reduced pressure and the residue extracted with methanol. The precipitate was filtered off and the solvent removed. The resulting oily residue containing the required product was used without further purification.

Compound 6-[(3-dimethylaminopropyl)aminomethyl]indole-3-carboxaldehyde was prepared by a procedure similar to the one described for 6-[(2-methoxyethyl)aminomethyl]indole-3-carboxaldehyde.

Example 321

Synthesis of 5-acetaminomethylindole-3-carboxaldehyde

5-Aminomethylindole (5.3 g, 0.036 mol) was mixed with acetic anhydride (13 ml) and kept at room temperature for 3 h. The solvent was removed under reduced pressure and the residue was stirred with toluene. The precipitated solid was collected by filtration to yield 6.1 g (89%) of 5-acetaminomethylindole.

Phosphorus oxychloride (0.38 ml, 0.004 mol) was slowly added at 0° C. under nitrogen atmosphere to anhydrous N,N-dimethylformamide (1.9 ml, 0.025 mol). The mixture was stirred for 15 minutes and a solution of 5-acetaminomethylindole (0.73 g, 0.0039 mol) in anhydrous N,N-dimethylformamide (4 ml) was added dropwise below 2° C. The mixture was stirred at room temperature for 3 h and diluted with an equal volume of water. The solution was neutralized (pH 8) with 1 N aqueous solution of sodium hydroxide. The mixture was evaporated to dryness under reduced pressure and the residue was recrystallized from ethyl acetate to afford 0.5 g (60%) of the entitled product (mp 182–184° C.).

Example 322

Synthesis of 6-(N,N-dimethylaminosulfonyl)indole-3-carboxaldehyde

Phosphorus oxychloride (0.76 ml, 0.008 mol) was slowly added at 0° C. under nitrogen atmosphere to anhydrous N,N-dimethyl formamide (3.8 ml), 0.05 mol). The mixture was stirred for 15 minutes and a solution of 6-(N,N-dimethyl aminosulfonyl)indole (1.74 g, 0.0078 mol) in anhydrous N,N-dimethylformamide (4 ml) was added dropwise below 2° C. The reaction mixture was allowed to stand at room temperature for 20 h and diluted with water (10 ml). The solution was neutralized (pH 8) with 10% aqueous solution of sodium hydroxide. The mixture was cooled and the precipitated solid was collected by filtration and was recrystallized from ethanol to yield 1.05 g (54%) of the entitled product (mp 250–252° C.).

Example 323

8-(Acetoxymethyl)-6,7,8,9-tetrahydro-pyrido[1,2-a]-indole-10-carboxaldehyde

Phosphorus oxychloride (0.76 ml, 0.008 mol) was slowly added at 0° C. under nitrogen atmosphere to anhydrous N,N-dimethylformamide (3.8 ml, 0.05 mol). The mixture was stirred for 15 minutes and a solution of 8-(acetoxymethyl)-6,7,8,9-tetrahydro-pyrido[1,2-a]indole (1.9 g, 0.0078 mol) in anhydrous N,N-dimethyl formamide (19 ml) was added dropwise below 2° C. The mixture was stirred at 0° C. for 2 h, poured into crushed ice and the solution was neutralized (pH 8) with 10% aqueous solution of sodium hydroxide and the mixture was extracted with ethyl acetate, washed with water, 10% aqueous sodium hydrogencarbonate solution and water. The organic solvent was dried over anhydrous magnesium sulfate to yield 1.77 g (84%) of the entitled product (mp 118–120° C.).

D. Imidazole-5-carboxaldehydes.

Example 324

Synthesis of a mixture of 1-(N,N-diethyl-2-aminoethyl)-4(5)-methylimidazole-5(4)-carboxaldehydes A solution of 4(5)-methylimidazole-5(4)-carboxaldehyde (1 g, 9.09 mmol) in dry N,N-dimethylformamide (30 ml) was added dropwise under nitrogen atmosphere to a stirring suspension of 60% sodium hydride (oil dispersion) (0.73 g, 18.16 mmol) in dry N,N-dimethylformamide (10 ml) keeping the temperature between 5–10° C. (ice-water bath). After addition was completed, stirring was continued at the same temperature for 30 min. Then a solution of N,N-diethyl aminoethyl chloride hydrochloride in dry N,N-dimethylformamide (20 ml) was added dropwise. After that a catalytic amount of sodium iodide was added, and the temperature was allowed to rise to room temperature. The reaction mixture was stirred for 2 days. Water (50 ml) was added and the mixture extracted with dichloromethane (3×50 ml). The organic layer was dried over anhydrous magnesium sulfate, filtered and the solvent removed under reduced pressure to give an oil containing a mixture of the entitled compounds (1 g, 52%) which was used without further purification.

Example 325 was prepared following the procedure described for example 324 using the appropriate halogen derivative and 4(5)-methylimididazole-5(4)-carboxaldehyde.

TABLE 78

N-substituted 4(5)-methylimidazole-5(4)-carboxaldehydes synthesized.

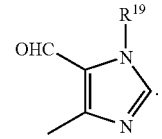

L

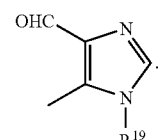

LI

| Example | Structure number | $R^{19}$ |
|---|---|---|
| 324 | L | 1-[$CH_2$—$CH_2$—$N(CH_2$—$CH_3)_2$] |
| 324 | LI | 1-[$CH_2$—$CH_2$—$N(CH_2$—$CH_3)_2$] |

TABLE 78-continued

N-substituted 4(5)-methylimidazole-5(4)-carboxaldehydes synthesized.

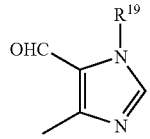

| Example | Structure number | R<sup>19</sup> |
|---|---|---|
| 325 | L | 1-(CH$_2$—CH$_2$—N(morpholine)) |
| 325 | LI | 1-(CH$_2$—CH$_2$—N(morpholine)) |

Example 326

Synthesis of 4(5)-hydroxymethylimidazole-5(4)-carboxaldehyde

4(5)-Diethoxymethyl-5(4)-methoxycarbonylimidazole (0.75 g, 0.0033 mol) was added portionwise with ice cooling under nitrogen atmosphere to a stirred suspension of lithium aluminum hydride (0.33 g, 0.0088 mol) in anhydrous tetrahydrofurane (40 ml). The mixture was stirred at room temperature for 3 hr and quenched by cautious addition of saturated aqueous of sodium sulfate. The reaction mixture was filtered and the filtrate was evaporated under reduced pressure, to yield 0.46 g (65%) of 4(5)-diethoxymethyl-5(4)-hydroxymethylimidazole, which was used without further purification in the next step 4(5)-Diethoxymethyl-5(4)-hydroxymethylimidazole (0.23 g, 0.0011 mol) was stirred with acetic acid/water (8 ml/2 ml) at room temperature for 2 hr. The reaction mixture was evaporated to dryness to yield 0.13 g (95%) of the entitled product, mp 160–162° C.

E. Pyrazole-4-carboxaldehydes.

Aldehydes included in Table 79 were prepared following the procedure described for example 324 using the appropriate halogen derivative and 3-methylpyrazole-4-carboxaldehyde.

TABLE 79

N-substituted 3-methylpyrazole-4-carboxaldehydes synthesized.

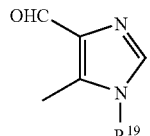

| Example | Structure number | R<sup>20</sup> |
|---|---|---|
| 327 | LII | 1-[CH$_2$—CH$_2$—N(CH$_2$—CH$_3$)$_2$] |
| 327 | LIII | 1-[CH$_2$—CH$_2$—N(CH$_2$—CH$_3$)$_2$] |
| 328 | LII | 1-(CH$_2$—CH$_2$—N(morpholine)) |
| 328 | LIII | 1-(CH$_2$—CH$_2$—N(morpholine)) |
| 329 | LII | 1-(CH$_2$—CO$_2$CH$_2$CH$_3$) |
| 329 | LIII | 1-(CH$_2$—CO$_2$CH$_2$CH$_3$) |

F. Indole-7-carboxaldehydes and Indole-4-carboxaldehydes.

Example 330

Synthesis of 3-dimethylaminomethyl-7-indolcarboxaldehyde

A mixture of 7-indolcarboxaldehyde (0.25 g, 1.7 mmol) and Eschenmoser's salt (0.35 g, 1.9 mmol) in dry acetonitrile (10 ml) was heated under reflux for 2½h. After cooling, solvent was removed under reduced pressure and water was added to the residue. The cooled mixture (ice bath) was made alkaline with 10% sodium hydroxide and then extracted with dichloromethane. The combined organic extracts were washed with brine, dried over anhydrous magnesium sulfate and evaporated to afford 0.25 g (74%) of the entitled product.

Example 331

Synthesis of 3-morpholinomethyl-4-indolcarboxaldehyde

Morpholine (0.24 ml, 2.7 mmol) and formaldehyde (37% aq; 0.21 ml, 2.7 mmol) were added to glacial acetic acid (3 ml) at 0° C. After stirring for 15 minutes 4-indolcarboxaldehyde (0.27 g, 1.9 mmol) was added. The mixture was stirred 5 minutes at 0° C. and then 3½h at room temperature, prior to the addition of water (6 ml) and washing with ether. The aqueous layer was made alkaline with 2N NaOH and then extracted with dichloromethane. The combined organic extracts were washed with brine, dried over anhydrous magnesium sulfate and evaporated to afford 0.46 g of the entitled product as an oil which was used without further purification.

Aldehydes included in Table 80 were prepared following the procedures described for compounds 330 and 331.

TABLE 80

Indole-7-carboxaldehydes synthesized.

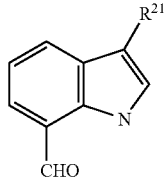

| Example | $R^{21}$ | Mp(° C.) | Yield % |
|---|---|---|---|
| 330 | dimethylaminomethyl | 205–7 | 74 |
| 332 | morpholinomethyl | 148–50 | 86 |
| 333 | piperidinomethyl | 84–7 | 100 |
| 334 | (4-methylpiperazin-1-yl)methyl | NA(oil) | 93 |
| 335 | [4-(2-hydroxyethyl)piperazin-1-yl]methyl | 87–90 | 93 |

G. Example 136

Synthesis of
6-Cyano-2H-1,4-Benzoxazin-3(4H)-one

Chloroacetyl chloride (3.12 ml, 38 mmol) was added dropwise to a solution of 2-amino-4-cyanophenol (4.96 g, 37 mmol), triethylamine (10.98 ml, 78 mmol) and 4-(dimethylamino)pyridine (0.09 g, 0.74 mmol) in dry dichloromethane (40 ml) maintained at 0° C. The solution refluxed for 24 h. The reaction mixture was cooled, and the organic layer was washed with phosphoric acid (0.5 M), saturated sodium bicarbonate, water and brine, then dried with anhydrous magnesium sulfate. The organic layer was filtered, then evaporated to dryness. The residue was recrystalized from ethanol to afford 3.9 g (60%) of the titled compound. (mp 243–245° C.).

H. Synthesis of 2H-1,4-Benzothiazin-3-ones.

Example 337

Synthesis of 1-Oxo-2H-1,4-Benzothiazin-3(4H)-one

A solution of 3-chloroperbenzoic acid (1.35 g, 6.6 mmol) in dry dichloromethane (40 ml) was added dropwise to an ice cooled solution of 2H-1,4-benzothiazin-3(4H)-one (1.10 g, 6.6 mmol) in dry dichloromethane (100 ml) with stirring. The reaction mixture was allowed to reach room temperature, then stirred overnight. The product was collected by filtration and washed with dichloromethane. Yield 0.54 g (45%) mp 184–6° C.

Example 338

Synthesis of 7-(N,N-Dimethyl-3-aminopropyloxy)-2H-1,4-benzothiazin-3(4H)-one

N,N-dimethyl-3-aminopropanol (0.27 g, 5.2 mmol) was added to a mixture of 7-hydroxy-2H-1,4-benzothiazin-3 (4H)-one (0.95 g, 5.2 mmol) and triphenylphosphine (1.37 g, 5.2 mmol) in dry tetrahydrofurane (30 ml) under nitrogen atmosphere, followed by diethyl azodicarboxylate (1 g, 5.7 mmol). The mixture was stirred at room temperature for 48 h, concentrated in vacuo, and the product was purified by silica gel chromatography using dichloromethane:methanol gradient of (9:1) to (7:3) as the mobile phase. Yield 1.1 g (75%) mp 120–121° C.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A compound represented by the following structural formula:

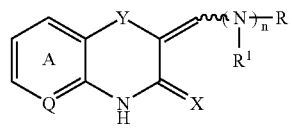

or physiologically acceptable salts thereof, wherein:
ring A is optionally substituted with substituents as defined below;
Q is —N═ or —CR²═;
X is S, O or NOR³;
Y is —S—, —SO— or —SO₂R
R is selected from the group consisting of indole, pyrrole, 7-azaindole, imidazole and indazole optionally substituted with substituents as defined below;
R¹ is hydrogen, an optionally substituted straight chained or branched $C_1$–$C_{18}$ hydrocarbon or cyclic $C_3$–$C_{18}$ hydrocarbon which are completed saturated or which contain one or more units of unsaturation or straight chained or branched $C_1$–$C_{18}$ hydrocarbon or cyclic $C_3$–$C_{18}$ hydrocarbon which are completed saturated or which contain one or more units of unsaturation substituted with substituents as defined below, or optionally substituted benzyl, cinnamyl, naphthyl, 1,2,3,4-tetrahydronaphthyl, pyridinyl, thiophenyl, furanyl, pyrrolyl, imidazolyl, pyrazolyl, triazolyl, pyrimidinyl, pyrazinyl, pyridazinyl, oxazolyl, thiazolyl, isoxazolyl, isothiazolyl, tetrazolyl, oxadiazolyl, thiazolyl, benzimidazolyl, indolyl, tetrahydroindolyl, azaindolyl, indazolyl, quinolinyl, imidazopyridinyl, purinyl, pyrrolyl[2,3-d]pyrimidinyl, pyrazolo[3,4-d]pyrimidinyl and their N-oxides, or a pyridinyl, thiophenyl, furanyl, pyrrolyl, imidazolyl, pyrazolyl, triazolyl, pyrimidinyl, pyrazinyl, pyridazniyl, oxazolyl, thiazolyl, isoxazolyl, isothiazolyl, tetrazolyl, oxadiazolyl or thiadiazolyl substituent linked to a compound by an straight chained or branched or cyclic hydrocarbon group which are completely saturated or unsaturated group having from one to six carbon atoms;
R² is —H or a substituent as defined below;
R³ is —H or —C(O)R⁴;
R⁴ is a straight chained or branched $C_1$–$C_{18}$ hydrocarbon or cyclic $C_3$–$C_{18}$ hydrocarbon which are completed saturated or which contain one or more units of unsaturation, unsubstituted or substituted with substituents as defined below or a group of benzyl, cinnamyl, naphthyl, 1,2,3,4-tetrahydronaphthyl, pyridinyl, thiophenyl, furanyl, pyrrolyl, imidazolyl, pyrazolyl, triazolyl, pyrimidinyl, pyrazinyl, pyridazinyl, oxazolyl, thiazolyl, ioxazolyl, isothiazolyl, tetrazolyl, oxadiazolyl, thiazolyl, benzimidazolyl, indolyl, tetrahydroindolyl, azaindolyl, indazolyl, quinolinyl, imidazopyridinyl, purinyl, pyrrolyl [2,3-d]pyrimidinyl, pyrazolo[3,4-d]pyrimidinyl and their N-oxides substituted with substituents as defined below;

n is 0; and wherein $R^1$ is hydrogen, unsubstituted or substituted straight chained or branched $C_1$–$C_{18}$ hydrocarbon or cyclic $C_3$–$C_{18}$ hydrocarbon which are completed saturated or which contain one or more units of unsaturation substituted with substituents as defined below;

when X is O and n is 0, $R^1$ is hydrogen straight chained or branched $C_1$–$C_{18}$ hydrocarbon or cyclic $C_3$–$C_{18}$ hydrocarbon which are completed saturated or which contain one or more units of unsaturation substituted with substituents as defined below; and when X is O and n is 1, $R^1$ is H straight chained or branched $C_1$–$C_{18}$ hydrocarbon or cyclic $C_3$–$C_{18}$ hydrocarbon which are completed saturated or which contain one or more units of unsaturation;

wherein substituents are selected from the group consisting of halogens, trihalomethyl, cyano, hydroxy, nitro, $NR^5R^6$, carbamoyl, carboxy, carboxamidoxime, —$SO_2NR^5R^6$, —$NHSO_2R^5$, $R^7$—O—$R^8$— or $R^7$—O—$R^8$—O—$R^9$—, $R^{11}$—, $R^{11}$O—, $R^{11}OC(O)$—, $R^{11}NHC(O)$—, $R^{11}C(O)$—, $R^{11}C(O)O$—, $R^{11}S$—, $R^{11}S(O)$—, $R^{11}S(O)_2$—, $R^5R^6NC(O)$—, $R^{11}HNC(O)NH$—, $R^{12}(CH_2)_m$—, $R^{12}(CH_2)_mC(O)NH$—, $R^{12}(CH_2)_mNH$—, [$R^{12}(CH_2)_m]_2CH$—O—$(CH_2)_m$—, $R^{12}(CH_2)_mOC(O)$—, $R^{12}(CH_2)_mNHC(O)$—, $R^{12}(CH_2)_mCH(R^{12})(CH_2)_m$—, $(CH_2)_mC(O)O$—, $R^{12}(CH_2)_mNHC(O)O$—, $R^{12}(CH_2)_m,OC(O)NH$—, $R^{12}(CH_2)_mOC(O)O$—, $R^{12}(CH_2)_mNHC(O)(CH_2)_m$—, $R^{12}(CH_2)_mOC(O)(CH_2)_m$—, $R^{12}(CH_2)_mCR^5CR^6)_m(CH_2)_mN(R^5)(CH_2)_m$—, $R^{12}C(O)(CH_2)_m$—, $R^{12}(CH_2)_m(CR^5R^6)_m(CH_2)_mN(R^5)C(O)(CH_2)_m$—, $R^{12}(CH_2)_m(CR^5R^6)_m(CH_2)_mN(R^5)(CH_2)_mC(O)$—, [$R^{12}(CH_2)_m]_2NC(O)(CH_2)_mC(O)$—, $R^{12}(CH_2)_m$—, $R^{12}(CH_2)_m(CR^5R^6)_m(CH_2)_mN(R^5)SO_2$—, and $R^{12}(CH_2)_m(CR^5R^6)_m(CH_2)_mO(CH_2)_m$—;

wherein $R^5$ and $R^6$ are each, independently, hydrogen, a lower alkyl, benzyl, pyridinyl-, thiophenyl-, furanyl-, pyrroly-l, imidazolyl-, pyrazolyl-, triazolyl-, pyrimidinyl-, pyrazinyl-, pyridazinyl-, oxazolyl-, thiazolyl-, isoxazolyl-, isothiazolyl-, tetrazolyl-, oxadiazolyl-, thiadiazolyl-, benzimidazolyl-, indolylmethyl or pyridinyl, thiophenyl, furanyl, pyrrolyl, imidazolyl, pyrazolyl, triazolyl, pyrimidinyl, pyrazinyl, pyridazniyl, oxazolyl, thiazolyl, isoxazolyl, isothiazolyl, tetrazolyl, oxadiazolyl or thiadiazolyl group optionally substituted with a halogen, cyano or hydroxy group;

$R^7$ is hydrogen, $R^{10}C(O)$—, or a lower alkyl or pyridinyl, thiophenyl, furanyl, pyrrolyl, imidazolyl, pyrazolyl, triazolyl, pyrimidinyl, pyrazinyl, pyridazniyl, oxazolyl, thiazolyl, isoxazolyl, isothiazolyl, tetrazolyl, oxadiazolyl or thiadiazolyl group which is optionally substituted with one or more halogens, cyano, hydroxy or —$NR^5R^6$;

$R^8$ and $R^9$ are each, independently, —C(O)— or a lower alkyl or pyridinyl, thiophenyl, furanyl, pyrrolyl, imidazolyl, pyrazolyl, triazolyl, pyrimidinyl, pyrazinyl, pyridazniyl, oxazolyl, thiazolyl, isoxazolyl, isothiazolyl, tetrazolyl, oxadiazolyl or thiadiazolyl group which is optionally substituted with one or more halogens, cyano, hydroxy or —$NR^5N^6$; and $R^{10}$ is a lower alkyl or an pyridinyl, thiophenyl, furanyl, pyrrolyl, imidazolyl, pyrazolyl, triazolyl, pyrimidinyl, pyrazinyl, pyridazniyl, oxazolyl, thiazolyl, isoxazolyl, isothiazolyl, tetrazolyl, oxadiazolyl or thiadiazolyl group;

$R^{11}$ is hydrogen, a lower alkyl group, pyridinyl, thiophenyl, furanyl, pyrrolyl, imidazolyl, pyrazolyl, triazolyl, pyrimidinyl, pyrazinyl, pyridazniyl, oxazolyl, thiazolyl, isoxazolyl, isothiazolyl, tetrazolyl, oxadiazolyl or thiadiazolyl group or an aromatic group having five to six atoms substituent that is linked to a compound by straight chained or branched group having from one to six carbon atoms which are completely saturated or which contain one or more units of unsaturation, where these groups are optionally substituted with one or more halogens, cyano, hydroxy or —$NR^5R^6$;

$R^{12}$ is halogen, carboxy, carbamoyl, lower alkyloxycarbonyl, lower alkenyl, hydroxy, a lower alkyloxy, lower alcanoyloxy, —$NR^5R^6$ or is selected from the group consisting of morpholinyl, piperazinyl, piperidinyl, pyrrolidinyl, homopiperazinyl, pyridinyl, triazolyl, tetrazolyl, imidazolyl and hydropyranyl optionally substituted with an hydroxy, lower alklyl, lower alkyloxy, lower hydroxyalkyl, lower aminoalkyl, lower alkyloxyalkyl, a saturated or unsaturated heterocyclic ring, cycloalkyl or —$NR^5R^6$ group;

m is independently an integer from 0 to 4.

2. A compound of claim 1, wherein Q is $CH_2$; Y is S; and R is selected from the group consisting of substituted or unsubstituted pyrrole, imidazole, indole, 7-azaindole and indazole.

3. A compound of claim 2 wherein R is optionally substituted with one or more moieties selected from the group consisting of halogens, trihalomethyl, cyano, hydroxy, nitro, —$NR^5R^6$, carbamoyl, carboxy, carboxamidoxime, $SO_2NR^5R^6$, —$SO_2NR^5R^6$, —$NHSO_2R^5$, $R^7$—O—$R^8$—, $R^7$—O—$R^8$—O—$R^9$—, $R^{11}$—, $R^{11}$O—, $R^{11}OC(O)$—, $R^{11}N(R^5)C(O)$—, $R^{11}C(O)$—, $R^{11}C(O)O$—, $R^{11}S$—, $R^{11}S(O)$—, $R^{11}S(O)_2$—, $(R^5R^6)NC(O)$—, $R^{11}(R^5)NC(O)N(R^5)$—, $R^{11}C(O)N(R^5)$—, $R^{12}(CH_2)_m$—, $R^{12}(CH_2)_mC(O)N(R^5)$—, $R^{12}(CH_2)_mO$—, $R^{12}(CH_2)_mN(R^5)$—, [$R^{12}(CH_2)_m]_2CH$—O—$(CH_2)_m$—, $R^{12}(CH_2)_mOC(O)$—, $R^{12}(CH_2)_mN(R^5)C(O)$—, $R^{12}(CH_2)_mCH(R^{12})(CH_2)_m$—, $R^{12}(CH_2)_mC(O)O$—, $R^{12}(CH_2)_mN(R^5)C(O)O$—, $R^{12}(CH_2)_mOC(O)N(R^5)$—, $R^{12}(CH_2)_mOC(O)O$—, $R^{12}(CH_2)_mN(R^5)C(O)(CH_2)_m$—, $R^{12}(CH_2)_mOC(O)(CH_2)_m$—, $R^{12}(CH_2)_m(CR^5R^6)_m(CH_2)_mN(R^5)(CH_2)_m$—, $R^{12}C(O)(CH_2)_mC(O)$—, $R^{12}C(O)(CH_2)_m$—, $R^{12}(CH_2)_m(CR^5R^6)_m(CH_2)_mN(R^5)C(O)(CH_2)_m$—, $R^{12}(CH_2)_m(CR^5R^6)_m(CH_2)_mN(R^5)(CH_2)_mC(O)$—, [$R^{12}(CH_2)_m]_2NC(O)(CH_2)_m$—, $R^{12}(CH_2)_mC(O)$—, $R^{12}(CH_2)_m(CR^5R^6)_m(CH_2)_mN(R^5)SO_2$—, $R^{12}(CH_2)_m(CR^5R^6)_m(CH_2)_mO(CH_2)_m$—, wherein:

$R^5$ and $R^6$ for each occurrence are each independently selected from the group consisting of hydrogen, a lower alkyl, benzyl, heteroarylmethyl and aryl group optionally substituted with a halogen, cyano or hydroxy group;

$R^7$ for each occurrence is independently selected from the group consisting of hydrogen, $R^{10}C(O)$—, a lower alkyl and an aryl group optionally substituted with one or more halogens, cyano, hydroxy or —$NR^5R^6$;

$R^8$ and $R^9$ for each occurrence are each independently selected from the group consisting of —C(O)—, a lower alkyl or an aryl group optionally substituted with one or more halogens, cyano, hydroxy or —NR$^5$R$^6$;

R$^{10}$ for each occurrence is independently selected from a group consisting of a lower alkyl and an aryl group optionally substituted with one or more halogens, cyano, hydroxy or —NR$^5$R$^6$;

R$^{11}$ for each occurrence is independently hydrogen or selected from an optionally substituted group consisting of a lower alkyl group, a saturated or unsaturated heterocyclic ring, an aryl group and an aralkyl group, where said groups are optionally substituted with one or more halogens, cyano, hydroxy or —NR$^5$R$^6$;

R$^{12}$ for each occurrence is independently selected from the group consisting of halogen, carboxy, carbamoyl, lower alkyloxycarbonyl, lower alkenyl, hydroxy, a lower alkyloxy, a lower alcanoyloxy, and —NR$^5$R$^6$; or is selected from an optionally substituted group consisting of morpholine, piperazine, piperidine, pyrrolidine, homopiperazine, pyridine, triazole, tetrazole, imidazole and tetrahydropyrane, where said groups are optionally substituted with one or more hydroxy, lower alkyl, lower alkyloxy, lower hydroxyalkyl, lower aminoalkyl, lower alkyloxyalkyl, a saturated or unsaturated heterocyclic ring, cycloalkyl or —NR$^5$R$^6$ group; and m is independently an integer from 0 to 4.

4. A compound of claim 3, wherein X is O and n is 0.
5. A compound of claim 3, wherein X is S.
6. A compound of claim 3, wherein X is NOR$_3$.
7. A compound of claim 4 wherein R is selected from the group consisting of:
pyrrol-2-yl,
5-methylpyrrol-2-yl,
3,5-dimethylpyrrol-2-yl,
4,5-dimethylpyrrol-2-yl,
4-ethyl-3,5-dimethylpyrrol-2-yl,
4-ethoxycarbonyl-3,5-dimethylpyrrol-2-yl,
1-methylpyrrol-2-yl,
1-(4-hydroxybutyl)pyrrol-2-yl,
1-(2-hydroxyethyl)pyrrol-2-yl,
1-(3-dimethylaminopropyl)pyrrol-2-yl,
4-bromopyrrol-2-yl,
1-[N-(2-morpholinoethyl)carbamoylmethyl]pyrrol-2-yl,
1-(ethoxycarbonylmethyl)pyrrol-2-yl,
1-(carboxymethyl)pyrrol-2-yl,
1-[N-(3-dimethylaminopropyl)carbamoylmethyl]pyrrol-2-yl,
1-[(4-methylpiperazin-1-yl)carbonylmethyl]pyrrol-2-yl,
indol-3-yl,
1-(4-hydroxybutyl)indol-3-yl,
5-methoxyindol-3-yl,
1-(2-hydroxyethyloxymethyl)indol-3-yl,
1-(3-dimethylaminopropyl)indol-3-yl,
6-methoxycarbonylindol-3-yl,
2-methylindol-3-yl,
1-methylindol-3-yl,
1-isopropylindol-3-yl,
1-(2-hydroxy-3-dimethylaminopropyl)indol-3-yl,
5-hydroxyindol-3-yl,
6-carboxyindol-3-yl,
5-amino-2-methylindol-3-yl,
6-(2-dimethylaminoethyloxycarbonyl)indol-3-yl,
6-(2-morpholinoethyloxycarbonyl)indol-3-yl,
6-(3-dimethylaminopropylcarbamoyl)indol-3-yl,
1-(carbamoylmethyl)indol-3-yl,
1-(ethoxycarbonylmethyl)indol-3-yl,
4-methoxycarbonylindol-3-yl,
1-(2-ethoxycarbonylethyl)indol-3-yl,
7-methoxycarbonylindol-3-yl,
2-ethoxycarbonylindol-3-yl,
1-cyclopentylindol-3-yl,
1-(3-tetrahydrofuranyl)indol-3-yl,
6-(N,N-dimethylaminosulfonyl)indol-3-yl,
5-(acetylaminomethyl)indol-3-yl,
1-(diethylcarbamoyl)indol-3-yl,
5-hydroxy-1-methylindol-3-yl,
6-methoxyindol-3-yl,
6-hydroxyindol-3-yl,
6-[2-(pyrrolidin-1-yl)ethyloxycarbonyl]indol-3-yl,
6-(2-dimethylaminoethyloxycarbonyl)-1-methylindol-3-yl,
6-(3-dimethylaminopropyloxycarbonyl)indol-3-yl,
6-carboxy-1-(2-hydroxyethyl)indol-3-yl,
6-{N-[2-(pyrrolidin-1-yl)ethyl]carbamoyl}indol-3-yl,
6-[N-(2-morpholinoethyl) carbamoyl]indol-3-yl,
6-[N-(2-dimethylaminoethyl)carbamoyl]indol-3-yl,
6-{N-[3-(4-methylpiperazin-1-yl)propyl]carbamoyl}indol-3-yl,
6-{N-[2-(piperidin-1-yl)ethyl]carbamoyl}indol-3-yl,
6-[N-(2-dimethylaminopropyl)carbamoyl]indol-3-yl,
6-{[N-(2-dimethylaminoethyl)-N-methyl]carbamoyl}indol-3-yl,
6-[(4-methylpiperazin-1-yl)carbonyl]indol-3-yl,
5-[2-(piperidin-1-yl)ethyloxy]indol-3-yl,
5-(3-dimethylaminopropyloxy)indol-3-yl,
5-(2-morpholinoethyloxy)indol-3-yl,
5-(3-dimethylaminopropyloxy)-1-(isopropyloxycarbonyl)indol-3-yl,
5-(3-dimethylaminopropyloxy)-1-methylindol-3-yl,
5-(2-morpholinoethyloxy)-1-methylindol-3-yl,
5-[2-(pyrrolidin-1-yl)ethyloxy]indol-3-yl,
5-(2-dimethylaminoethyloxy)indol-3-yl,
6-(3-dimethylaminopropyloxy)indol-3-yl,
6-(2-morpholinoethyloxy)indol-3-yl,
6-[2-(piperidin-1-yl)ethyloxy]indol-3-yl,
6-[2-(pyrrolidin-1-yl)ethyloxy]indol-3-yl,
6-(2-dimethylaminoethyloxy)indol-3-yl,
6-[(2-dimethylamino-2-methyl)propyloxy]indol-3-yl,
6-[2-(1-methylpyrrolidin-2-yl)ethyloxy]indol-3-yl,
6-[2-(1-methylpiperidin-3-yl)methyloxy]indol-3-yl,
7-(dimethylaminomethyl)-6-hydroxyindol-3-yl,
7-(dimethylaminomethyl)-6-(2-morpholinoethyloxy)indol-3-yl,
2-methyl-5-(N'-ethylureido)indol-3-yl,
2-methyl-5-(p-toluensulfonylamino)indol-3-yl,
6-[(3-dimethylaminopropyl)aminomethyl]indol-3-yl,
6-[(2-methoxyethyl)aminomethyl]indol-3-yl,
1-(carboxymethyl)indol-3-yl,
1-[N-(2-morpholinoethyl)carbamoylmethyl]indol-3-yl,
1-[N-(2-methoxyethyl)carbamoylmethyl]indol-3-yl,
1-[N-(3-dimethylaminopropyl)carbamoylmethyl]indol-3-yl,
1-{N-(2-(2-pyridyl)ethyl) carbamoylmethyl]indol-3-yl,
1-{N-[2-(pyrrolidin-1-yl)ethyl]carbamoylmethyl}indol-3-yl,
7-[N-(3-dimethylaminopropyl)carbamoyl]indol-3-yl,
1-[(4-methylpiperazin-1-yl)carbonylmethyl]indol-3-yl,
1-[N,N-bis(2-N',N'-diethylaminoethyl)carbamoylmethyl]indol-3-yl,
1-[(4-piperidinopiperidin-1-yl)carbonylmethyl]indol-3-yl,
1-{[N-(2-N',N'-diethylaminoethyl)-N-methyl]carbamoylmethyl}indol-3-yl,
7-carboxyindol-3-yl,
7-[(4-methylpiperazin-1-yl)carbonyl]indol-3-yl, 7-{[4-(2-hydroxyethyl)piperazin-1-yl]carbonyl}indol-3-yl,
7-azaindol-3-yl,
1-(4-hydroxybutyl)-7-azaindol-3-yl,
1-(2-hydroxyethyloxymethyl)-7-azaindol-3-yl,
1-(3-dimethylaminopropyl)-7-azaindol-3-yl,
1-(2-morpholinoethyl)-7-azaindol-3-yl,
1-(4-acetoxybutyl)-7-azaindol-3-yl,
1-(2-hydroxyethyl)-7-azaindol-3-yl,
1-methyl-7-azaindol-3-yl,
1-methoxymethyl-7-azaindol-3-yl,
1-(2-dimethylaminomethyl)-7-azaindol-3-yl,
1-(ethoxycarbonylmethyl)-7-azaindol-3-yl,
1-[N-(2-morpholinoethyl)carbamoylmethyl]-7-azaindol-3-yl,
1-carboxymethyl-7-azaindol-3-yl,
1-{N-[3-(4-methylpiperazin-1-yl)propyl]carbamoylmethyl}-7-azaindol-3-yl,
1-[(4-methylpiperazin-1-yl)carbamoylmethyl]-7-azaindol-3-yl,
1-{[N-(2-N',N'-diethylaminoethyl)-N-methyl]carbamoylmethyl}-7-azaindol-3-yl,
1-{[N-(1-ethylpyrrolidin-2-yl)methyl]carbamoylmethyl}-7-azaindol-3-yl,
1-[(4-methylhomopiperazin-1-yl)carbonylmethyl]-7-azaindol-3-yl,
1-[(4-ethylpiperazin-1-yl)carbonylmethyl]-7-azaindol-3-yl,
1-[(4-piperidinopiperidin-1-yl)carbonylmethyl]-7-azaindol-3-yl,
1-[N,N-bis(2-N',N'-diethylaminoethyl)carbamoylmethyl]-7-azaindol-3-yl,
imidazol-2-yl,
4-trifluoromethylimidazol-2-yl,
4-cyanoimidazol-2-yl,
1-methyl-1H-benzo[d]imidazol-2yl,
imidazol-5-yl,
4(5)-methylimidazol-5(4)-yl,
2-methylimidazol-5-yl,
2-ethyl-4(5)-methylimidazol-5(4)-yl,
3-(2-diethylaminoethyl)-4-methylimidazol-5-yl,
1-(2-diethylaminoethyl)-4-methylimidazol-5-yl,
1-(2-morpholinoethyl)-4-methylimidazol-5-yl,
3-(2-morpholinoethyl)-4-methylimidazol-5-yl,
1-methyl-2-methylthioimidazol-5-yl,
4(5)-methoxycarbonylimidazol-5(4)-yl,
4(5)-hydroxymethylimidazol-5(4)-yl,
indol-2-yl,
pyrrol-3-yl,
indazol-3-yl,
3-(morpholinomethyl)indol-4-yl,
indol-7-yl,
3-(dimethylaminomethyl)indol-7-yl,
3-(morpholinomethyl)indol-7-yl,
3-(piperidinomethyl)indol-7-yl,
3-[(4-methylpiperazin-1-yl)methyl]indol-7-yl,
3,5-dimethyl-4-dimethylaminomethylpyrrol-2-yl,
4-carboxyimidazol-2-yl,
7-{N-[3-(imidazol-1-yl)propyl]carbamoyl}indol-3-yl,
7-{N-[3-(4-methylpiperazin-1-yl)propyl]carbamoyl}indol-3-yl,
7-[N-(2-dimethylaminopropyl)carbamoyl]indol-3-yl,
7-{N-[2-(pyrrolidin-1-yl)ethyl]carbamoyl}indol-3-yl,
7-[(4-ethylpiperazin-1-yl)carbonyl]indol-3-yl,
7-[(4-methylhomopiperazin-1-yl)carbonyl]indol-3-yl,
3-{[4-(2-hydroxyethyl)piperazin-1-yl]methyl}indol-7-yl,
3-[(4-hydroxypiperidin-1-yl)methyl]indol-7-yl,
1-[(piperazin-1-yl)carbonylmethyl]-7-azaindol-3-yl,
1-[(piperazin-1-yl)carbonylmethyl]indol-3-yl,
3-(2-dimethlaminoacetyl)indol-(7)-yl,
6-[(2-morpholinoethyl)aminomethyl]indol-3-yl,
6-}[2-pyrrolidin-1-yl)ethyl]aminomethyl]}indol-3-yl,
6-[(3-methoxycarbonylpropyl)oxy]indol-3-yl,
6{[(3-(4-methylpiperazin-1-yl)carbonyl]propyloxy}indol-3-yl,
6-{3-[N-(2-dimethylaminoethyl)-N-methyl]carbamoyl]propyloxy}indol-3-yl,
6-[(2-hydroxyethyl)oxymethyloxy]indol-3-yl,
6-{3-[(4-piperidinopiperidin-1-yl)carbonyl]propyloxy}indol-3-yl,
6-{3-{[4-(2-hydroxyethyl)piperazin-1-yl]carbonyl}propyloxy}indol-3-yl,
6-[(4-methylpiperazin-1-yl)methyl]indol-3-yl,
6-{[N-(2-dimethylaminoethyl)-N-methyl]aminomethyl}indol-3-yl,
7-(dimethylaminomethyl)-6-(2-methoxyethyloxy)indol-3-yl,
7-(dimethylaminomethyl)-6-(3-methoxycarbonylpropyloxy)indol-3-yl,
7-(dimethylaminomethyl)-6-{[3-(4-methylpiperazin-1-yl)carbonyl]propyloxy}indol-3-yl,
7-(dimethylaminomethyl)-6-[(2-hydroxyethyl)oxymethyloxy]indol-3-yl,
6-(2-methoxyethyloxy)-7-[(pyrrolidin-1-yl)methyl]indol-3-yl,
6-{[3-(4-methylpiperazin-1-yl)carbonyl]propyloxy}-7-[(pyrrolidin-1-yl)methyl]indol-3-yl,
6-[(2-hydroxyethyl)oxymethyloxy]-7-[(pyrrolidin-1-yl)methyl]indol-3-yl,
7-[[(pyrrolidin-1-yl)methyl]-6-{[2-(pyrrolidin-1-yl)ethyl]oxy}indol-3-yl,
6-[2-(pyrrolidin-1-yl)ethyloxy]-7-azaindol-3-yl,
6-(2-piperidinoethyloxy)-7-azaindol-3-yl,
6-[(2-dimethylamino-2-methyl)propyloxy]-7-azaindol-3-yl,
6[(2-hydroxyethyl)aminomethylcarbonyl]indol-3-yl,
6-{[2-(pyrrolidin-1-yl)ethyl]aminomethylcarbonyl}indol-3-yl,
6-[(2-diethylaminoethyl)aminomethylcarbonyl]indol-3-yl,
4-carbamoylimidazol-2-yl,
4(5)-methyl-2-(methylmercapto)imidazol-5(4)-yl,
4(5)-methyl-2-(methylsulfonyl)imidazol-5(4)-yl,
2-amino-4(5)-methylimidazol-5(4)-yl,
4(5)-dimethylaminomethylimidazol-5(4)-yl,
4(5)-methylaminomethylimidazol-5(4)-yl,
4(5)-diethylaminomethylimidazol-5(4)-yl,
6-(N-methylaminosulfonyl)indol-3-yl,
6-[N-(3-dimethylaminopropyl)sulfonyl]indol-3-yl,
6-{N-[2-(pyrrolidin-1-yl)ethyl]aminosulfonyl}indol-3-yl,
6-{N-[2-piperidinoethyl]aminosulfonyl}indol-3-yl,
6-{N-[2-morpholinoethyl]aminosulfonyl}indol-3-yl,
6-{N-[2-(piperidinomethyl]aminosulfonyl}indol-3-yl,
6-{N-[3-(4-methylpiperazin-1-yl)propyl]aminosulfonyl}indol-3-yl,
7-N-(2-morpholinoethyl)carbamoyl]indol-3-yl,
7-[N-(2-piperidinoethyl)carbamoyl]indol-3-yl,
7-{[N-(2-N',N'-diethylaminoethyl)-N-methyl]carbamoyl}indol-3-yl,
7-[N-(2-methoxyethyl)carbamoyl]indol-3-yl,
7-[(4-piperidinopiperidin-1-yl)carbonyl]indol-3-yl,
7-[(piperazin-1-yl)carbonyl]indol-3-yl,
7-{N-[(2,2,N',N'-tetramethyl)propyl]carbamoyl}indol-3-yl, 7-{N-[(1-ethylpyrrolidin-2-yl)methyl]carbamoyl}indol-3-yl,
7-{N-[2-(2-pyridyl)ethyl]carbamoyl}indol-3-yl,
6-{N-[2-(2-pyridyl)ethyl]carbamoyl}indol-3-yl,
6-[(4-piperidinopiperidin-1-yl)carbonyl]indol-3-yl,
6-[(piperazin-1-yl)carbonyl]indol-3-yl,
6-{N-[(2,2,N',N'-tetramethyl)propyl]carbamoyl}indol-3-yl,
6-{N-[(1-ethylpyrrolidin-2-yl)methyl]carbamoyl}indol-3-yl,
6-[(4-methylhomopiperazin-1-yl)carbonyl]indol-3-yl,
6-[(4-butylpiperazin-1-yl)carbonyl]indol-3-yl,
6-[(4-ethylpiperazin-1-yl)carbonyl]indol-3-yl,
6-{[4-(2-(pyrrolidin-1-yl)ethyl)piperidin-1-yl]carbonyl}indol-3-yl,
6-{[N-(3-dimethylamino)prop-2-yl]carbamoyl}indol-3-yl,
6-{N-[3-(imidazol-1-yl)propyl]carbamoyl}indol-3-yl,
6-{[4-(2-hydroxyethyl)piperazin-1-yl]carbonyl}indol-3-yl,
3-[(4-ethylpiperazin-1-yl)methyl]indol-7-yl,
3-[(pyrrolidin-1-yl)methyl]indol-7-yl,
3-[(4-methylhomopiperazin-1-yl)methyl]indol-7-yl,
3-(diethylaminomethyl)indol-7-yl,
3-{[N-(2-N'N'-dimethylaminoethyl)-N-methyl]aminomethyl}indol-7-yl,
3-[(4-piperidinopiperidin-1-yl)methyl]indol-7-yl,
3-(2-piperidinoacetyl)indol-7-yl,
3-[2-(pyrrolidin-1-yl)acetyl]indol-7-yl,
3-(2-diethylaminoacetyl)indol-7-yl,
3-[2-(4-methylpiperazin-1-yl)acetyl]indol-7-yl,
3-[2-(4-methylhomopiperazin-1-yl)acetyl]indol-7-yl,
3-(2-morpholinoacetyl)indol-7-yl,
3-{2-[(2-methoxyethyl)amino]acetyl}indol-7-yl,
3-{2-[(2-piperidinoethyl)amino]acetyl}indol-7-yl,
3-{2-{[3-(imidazol-1-yl)propyl]amino}acetyl}indol-7-yl,
6-[3-(carboxypropyl)oxy]indol-3-yl,
6-{3-[(4-methylhomopiperazin-1-yl)carbonyl]propyloxy}indol-3-yl,
6-[(2-homopiperidin-1-yl)ethyloxy]indol-3-yl,
6-[(2-diethylamino-1-methyl)ethyloxy]indol-3-yl,
6-{2-[(tetrahydropyran-2-yl)oxy]ethyloxy}indol-3-yl,
6-[(2-hydroxyethyl)oxy]indol-3-yl,
6-[2-(isopropyloxyl)ethyloxy]indol-3-yl,
6-[2-(methoxyethyl)oxy]indol-3-yl,
6-[(3-methoxypropyl)oxy]indol-3-yl,
6-[(3-methoxybutyl)oxy]indol-3-yl,
6-{[(N,N-diethylcarbamoyl)methyl]oxy}indol-3-yl,
7-[2-(piperidin-1-yl)ethyloxy]indol-3-yl,
7-[(2-homopiperidin-1-yl)ethyloxy]indol-3-yl,
7-[(2-diethylamino-1-methyl)ethyloxy]indol-3-yl,
7-{2-[(tetrahydropyran-2-yl)oxy]ethyloxy}indol-3-yl,
7-[(2-hydroxyethyl)oxy]indol-3-yl,
7-[2-(isopropyloxyl)ethyloxy]indol-3-yl,
7-[2-(methoxyethyl)oxy]indol-3-yl,
7-[(3-methoxypropyl)oxy]indol-3-yl,
7-[(3-methoxybutyl)oxy]indol-3-yl,
7-{[(N,N-diethylcarbamoyl)methyl]oxy}indol-3-yl,
7-(dimethylaminomethyl)-6-[(2-piperidin-1-yl)ethyloxy]indol-3-yl,
7-(dimethylaminomethyl)-6-[(2-homopiperidin-1-yl)ethyloxy]indol-3-yl,
7-(dimethylaminomethyl)-6-{2-[(tetrahydropyran-2-yl)oxy]ethyloxy}indol-3-yl,
7-(dimethylaminomethyl)-6-[(2-hydroxyethyl)oxy]indol-3-yl,
7-(dimethylaminomethyl)-6-[2-(isopropyloxyl)ethyloxy]indol-3-yl,
7-(dimethylaminomethyl)-6-[2-(methoxyethyl)oxy]indol-3-yl,
7-(dimethylaminomethyl)-6-[(3-methoxypropyl)oxy]indol-3-yl,
7-(dimethylaminomethyl)-6-[(3-methoxybutyl)oxy]indol-3-yl,
7-[(pyrrolidin-1-yl)methyl)]-6-[(2-piperidin-1-yl)ethyloxy]indol-3-yl,
7-[(pyrrolidin-1-yl)methyl)]-6-[(2-homopiperidin-1-yl)ethyloxy]indol-3-yl,
7-[(pyrrolidin-1-yl)methyl)]-6-{2-[(tetrahydropyran-2-yl)oxy]ethyloxy}indol-3-yl,
7-[(pyrrolidin-1-yl)methyl)]-6-[(2-hydroxyethyl)oxy]indol-3-yl,
7-[(pyrrolidin-1-yl)methyl)]-6-[2-(isopropyloxyl)ethyloxy]indol-3-yl,
7-[(pyrrolidin-1-yl)methyl)]-6-[2-(methoxyethyl)oxy]indol-3-yl,
7-[(pyrrolidin-1-yl)methyl)]-6-[(3-methoxypropyl)oxy]indol-3-yl,
7-[(pyrrolidin-1-yl)methyl)]-6-[(3-methoxybutyl)oxy]indol-3-yl,
6-[(2-homopiperidin-1-yl)ethyloxy]-7-azaindol-3-yl,
6-[(2-diethylamino-1-methyl)ethyloxy]-7-azaindol-3-yl,
6-{2-[(tetrahydropyran-2-yl)oxy]ethyloxy}-7-azaindol-3-yl,
6-[(2-hydroxyethyl)oxy]-7-azaindol-3-yl,
6-[2-(isopropyloxyl)ethyloxy]-7-azaindol-3-yl,
6-[2-(methoxyethyl)oxy]-7-azaindol-3-yl,
6-[(3-methoxypropyl)oxy]-7-azaindol-3-yl,
6-[(3-methoxybutyl)oxy]-7-azaindol-3-yl,
6-{[(N,N-diethylcarbamoyl)methyl]oxy}-7-azaindol-3-yl,
6-{4-(2-hydroxyethyl)piperazin-1-yl]methyl}indol-3-yl,
6-[(4-methylhomopiperazin-1-yl)]methylindol-3-yl,
6-[(4-piperidinopiperidin-1-yl)methyl]indol-3-yl,
6-{[3-(isopropyloxy)propyl]aminomethyl}indol-3-yl,
6-{[3,3-bis(ethyloxy)propyl]aminomethyl}indol-3-yl,
6-[(2,2-dimethyl-1,3-dioxolane-4-methane)aminomethyl]indol-3-yl,
6-{3-[(2-methoxyethyl)oxypropyl]aminomethyl}indol-3-yl,
6-{[3-(ethyloxy)propyl]aminomethyl}indol-3-yl,
6-[3-(butyloxy)propyl]aminomethyl]indol-3-yl,
6-[(3-methoxypropyl)aminomethyl]indol-3-yl,
6-(chloromethylcarbonyl)indol-3-yl,
6-[2-(isopropyloxyethyl)aminomethylcarbonyl]indol-3-yl,
6-{[(2-piperidin-1-yl)ethyl]aminomethylcarbonyl}indol-3-yl,
6-{[(2-homopiperidin-1-yl)ethyl]aminomethylcarbonyl}indol-3-yl,
6-{4-(2-hydroxyethyl)piperazin-1-yl]methylcarbonyl}indol-3-yl,
6-{[(4-methylhomopiperazin-1-yl)]methyl}carbonylindol-3-yl,
6-[(4-piperidinopiperidin-1-yl)methylcarbonyl]indol-3-yl,
6-{[3-(isopropyloxy)propyl]aminomethylcarbonyl}indol-3-yl, 6-{[3,3-bis(ethyloxy)propyl]aminomethylcarbonyl}indol-3-yl,
6-[(2,2-dimethyl-1,3-dioxolane-4-methane)aminomethylcarbonyl]indol-3-yl,
6-{3-[(2-methoxyethyl)oxypropyl]aminomethylcarbonyl}indol-3-yl,
6-{[3-(ethyloxy)propyl]aminomethylcarbonyl}indol-3-yl,
6-[3-(butyloxy)propyl]aminomethylcarbonyl]indol-3-yl, or
6-[(3-methoxypropyl)aminomethylcarbonyl]indol-3-yl.

8. A pharmaceutical composition comprising a compound of claim 1 or a physiologically acceptable salt thereof and a pharmaceutically acceptable diluent or carrier.

9. The compound which is 2-(1-(4-acetoxybutyl)-7-aza-indol-3-yl)methylene-2H-1,4-benzothiazin-3(4H)-one, or a physiologically acceptable salt thereof.

10. A pharmaceutical composition comprising the compound of claim 9, or a physiological salt thereof, and a pharmaceutically acceptable diluent or carrier.

* * * * *

UNITED STATES PATENT AND TRADEMARK OFFICE
CERTIFICATE OF CORRECTION

PATENT NO. : 7,049,312 B1  
APPLICATION NO. : 09/585925  
DATED : May 23, 2006  
INVENTOR(S) : Paul Rafferty et al.

It is certified that error appears in the above-identified patent and that said Letters Patent is hereby corrected as shown below:

Column 118, line 30 – remove "R"

Column 118, line 53 – change "pyridazniyl" to --pyridazinyl--

Column 119, line 2 – change "ioxazolyl" to --isoxazolyl--

Column 119, line 34 – change "$(CH_2)_mC(O)O$-" to --$R^{12}(CH_2)_mOC(O)$- --

Column 119, line 41 – change "$R^{12}(CH_2)_m$" to --$R^{12}(CH_2)_mC(O)$- --

Column 119, line 52 – change "pyridazniyl" to --pyridazinyl--

Column 119, line 58 – change "pyridazniyl" to --pyridazinyl--

Column 119, line 66 – change "pyridazniyl" to --pyridazinyl--

Column 120, line 5 – change "pyridazniyl" to --pyridazinyl--

Column 120, line 10 – change "pyridazniyl" to --pyridazinyl--

Column 120, line 13 – insert --or an aromatic-- before "substituent"

Column 120, line 13 – insert --having five or six atoms-- before "that"

Column 120, lines 38 – delete "-$SO_2NR^5R^6$,"

Signed and Sealed this

Twenty-first Day of November, 2006

JON W. DUDAS  
*Director of the United States Patent and Trademark Office*